US011253523B2

(12) United States Patent
Herbig et al.

(10) Patent No.: US 11,253,523 B2
(45) Date of Patent: *Feb. 22, 2022

(54) TOFACITINIB ORAL SUSTAINED RELEASE DOSAGE FORMS

(71) Applicant: PFIZER INC., New York, NY (US)

(72) Inventors: Scott Max Herbig, East Lyme, CT (US); Sriram Krishnaswami, East Lyme, CT (US); Joseph Kushner, IV, Bradford, RI (US); Manisha Lamba, Waterford, CT (US); Thomas C. Stock, Chester Springs, PA (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/817,689

(22) Filed: Mar. 13, 2020

(65) Prior Publication Data

US 2020/0206232 A1     Jul. 2, 2020

Related U.S. Application Data

(63) Continuation of application No. 15/915,750, filed on Mar. 8, 2018, now Pat. No. 10,639,309, which is a continuation of application No. 14/211,659, filed on Mar. 14, 2014, now Pat. No. 9,937,181.

(60) Provisional application No. 61/802,479, filed on Mar. 16, 2013, provisional application No. 61/864,059, filed on Aug. 9, 2013, provisional application No. 61/934,428, filed on Jan. 31, 2014.

(51) Int. Cl.
| | |
|---|---|
| *A61K 31/519* | (2006.01) |
| *A61K 45/06* | (2006.01) |
| *A61K 9/00* | (2006.01) |
| *A61K 9/20* | (2006.01) |
| *A61K 9/28* | (2006.01) |
| *A61K 9/48* | (2006.01) |
| *A61K 31/40* | (2006.01) |

(52) U.S. Cl.
CPC .......... *A61K 31/519* (2013.01); *A61K 9/0004* (2013.01); *A61K 9/2018* (2013.01); *A61K 9/2054* (2013.01); *A61K 9/2086* (2013.01); *A61K 9/2866* (2013.01); *A61K 9/4891* (2013.01); *A61K 31/40* (2013.01); *A61K 45/06* (2013.01)

(58) Field of Classification Search
None
See application file for complete search history.

(56) References Cited

U.S. PATENT DOCUMENTS

| | | |
|---|---|---|
| 3,247,066 A | 4/1966 | Milosovich |
| 3,845,770 A | 11/1974 | Theeuwes et al. |
| 3,952,741 A | 4/1976 | Baker |
| 4,519,801 A | 5/1985 | Edgren |
| 5,358,502 A | 10/1994 | Herbig et al. |
| 5,612,059 A | 3/1997 | Cardinal et al. |
| 5,681,584 A | 10/1997 | Savastano |
| 5,698,220 A | 12/1997 | Cardinal et al. |
| 5,736,159 A | 4/1998 | Chen et al. |
| 5,945,125 A | 8/1999 | Kim |
| 6,531,151 B1 | 3/2003 | Besse |
| 6,534,090 B2 | 3/2003 | Puthli et al. |
| 6,706,283 B1 | 3/2004 | Appel et al. |
| 2002/0044965 A1 | 4/2002 | Curatolo et al. |
| 2003/0175346 A1 | 9/2003 | Billotte et al. |
| 2005/0181062 A1 | 8/2005 | Appel et al. |
| 2005/0186285 A1 | 8/2005 | Ray et al. |
| 2006/0165798 A1 | 7/2006 | Edgren et al. |
| 2006/0223787 A1 | 10/2006 | Devane et al. |
| 2007/0031496 A1 | 2/2007 | Edgrem et al. |
| 2007/0190129 A1 | 8/2007 | Ahmed et al. |
| 2007/0248671 A1 | 10/2007 | Johnson et al. |
| 2008/0199527 A1 | 8/2008 | Curatolo et al. |
| 2010/0291026 A1 | 11/2010 | Rao et al. |
| 2013/0344149 A1 | 12/2013 | Stefan et al. |

FOREIGN PATENT DOCUMENTS

| | | |
|---|---|---|
| CN | 1874761 A | 12/2006 |
| EP | 0357369 | 3/1990 |
| WO | 98/33489 A1 | 8/1998 |
| WO | 9901121 | 1/1999 |
| WO | 0142246 | 6/2001 |
| WO | 02096909 | 12/2002 |
| WO | 2003/041656 A2 | 5/2003 |
| WO | 03048126 | 6/2003 |
| WO | 03048162 | 6/2003 |
| WO | 2005/020929 A2 | 3/2005 |
| WO | 2005053653 | 6/2005 |
| WO | 2007057762 | 5/2007 |
| WO | 2008005020 A1 | 1/2008 |
| WO | 2011039686 | 4/2011 |
| WO | 2012100948 | 8/2012 |
| WO | 2012100949 | 8/2012 |

(Continued)

OTHER PUBLICATIONS

Dew et al. "An Oral Preparation to Release Drugs in the Human Colon", Br. J. Clinical Pharmac., 14: 405-408 (1982).
Herbig et al., "Asymmetric-membrane tablet coatings for osmotic drug delivery", Journal of Controlled Release, 35:127-135 (1995).
Khosla et al., "The effect of tablet size on the gastric emptying of non-disintegrating tablets", International Journal of Pharmaceutics, 62:R9-R11 (1990).
Meyer et al., "Anti-inflammatory activity and neutrophil reductions mediated by the JAK1/JAK3 inhibitor, CP-690,550, in rat adjuvant-induced arthritis", Journal of Inflammation, 7:41 (2010).

(Continued)

*Primary Examiner* — Patricia Duffy
*Assistant Examiner* — Garen Gotfredson
(74) *Attorney, Agent, or Firm* — Christian M. Smolizza

(57) ABSTRACT

The present invention relates to oral sustained release formulations of tofacitinib and pharmaceutical acceptable salts thereof. The formulations described herein have desirable pharmacokinetic characteristics.

98 Claims, No Drawings

(56) References Cited

FOREIGN PATENT DOCUMENTS

| WO | 2014/147526 A1 | 9/2014 |
|---|---|---|
| WO | 2014/174073 | 10/2014 |

OTHER PUBLICATIONS

Ashraf-Khorassani et al., "Purification of Pharmaceutical Excipients with Supercritical Fluid Extraction", Pharmaceutical Development and Technology, 10:507-516 (2005).

Cole et al., "Enteric coated HPMC capsules designed to achieve intestinal targeting", International Journal of Pharmaceutics, 231:83-95 (2002).

Roy et al., "Multiparticulate formulation approach to pulsatile drug delivery: Current perspectives", Journal of Controlled Release, 134: 74-80 (2009).

Pfizer Inc., A Phase 1 Study to Evaluate the Pharmacokinetics (PK), Safety, and Bioavailability of a Modified-Release (MR) Formulation of Tofacitinib in Health Volunteers, Clinical Trial Record A3921132, (2012).

"Tasocitinib Oral Tablet Composition", IP.Com Journal, IP.Com Inc., West Henrietta, NY, US, 4 (2011).

G. M. Eisenberg, "Colorimetric determination of hydrogen peroxide" in Ind. Eng. Chem. (Anal. Ed.), 15, 327-328, (1943).

Remington: The Science and Practice of Pharmacy, 21st Edition, Chapter 47; pp. 950-951 (2006).

P.G. Welling, "Pharmacokinetics Processes and Mathematics", ACS Monograph 185, 145-149 (1986).

C.M. Andersson et al., "Advances in the Development of Pharmaceutical Antioxidants", Advances in Drug Research, 28, 65-180 (1996).

K. Waterman et al., "Impurities in Drug Products", Handbook of Isolation and Characterization of Impurities in Pharmaceuticals, 75-85 (2003).

"Tofacitinib", Drug R D, 4, 271-284 (2010).

West, CP-690550, a JAK3 inhibitor as an immunosuppressant for the treatment of rheumatoid arthritis, transplant rejection, psoriasis and other immune-mediated disorders, 491-504 (2009).

Burmester et al., "Tofacitinib (CP-690,550) in combination with methotrexate in patients with active rheumatoid arthritis with an inadequate response to tumour necrosis factor inhibitors: a randomised phase 3 trial", Lancet, 381, 451-460 (2013).

Cavagna et al., "Atheroslerosis and rheumatoid arthritis: more than a simple association", Mediators of Inflammation, 2012, Article ID 147354, 1-8 (2012).

Brown et al., "Treating Patients With Documents Atherosclerosis to National Cholesterol Education Program-Recommended Low-Density-Lipoprotein Cholesterol Goals With Atorvastatin, Fluvastin, Lovastatin and Simvastatin", Journal of the American College of Cardiology, 32(3), 665-672 (1998).

Pfizer Inc., "A Phase 1 Study to Evaluate the Pharmacokinetics and Safety of Three Modified Release and One Immediate Release Formulations of Tofacitinib (CP-690,550) in Healthy Volunteers", Clinical Trial Record NCT01499004.

Pfizer Inc., "Pharmacokinetics and Safety Study of Two CP-690,550 Controlled Release Formulation Following Single Dose in Healthy Volunteers", Clinical Trial Record NCT01185184.

Marucci et al., "Coated formulations: New insights into the release mechanism and changes in the film properties with a novel release cell", Journal of Controlled Release, 136: 206-212 (2009).

Santus, et al., "Osmotic drug delivery: a review of the patent literature", Journal of Controlled Release, 35: 1-21 (1995).

Thombre et al., "Osmotic drug delivery using swellable-core technology", Journal of Controlled Release, 94: 75-89 (2004).

Verma, et al., "Osmotically Controlled Oral Drug Delivery", Drug Development and Industrial Pharmacy, 26(7), 695-708 (2000).

Verma et al., "Formulation aspects in the development of osmotically controlled oral drug delivery systems", Journal of Controlled Release, 79: 7-27 (2002).

Zentner et al., "Osmotic Flow Through Controlled Porosity Films: An Approach to Delivery of Water Soluble Compounds", Journal of Controlled Release, 2: 217-229 (1985).

Limmadi et al., International Journal of Pharma Sciences, 3(4), 258-269 (2013).

Academy of Pharmaceutical Sciences. Pharmaceutical Society of Great Britain. Handbook of Pharmaceutical Excipients, 141-143, 1986.

U.S. Department of Health and Human Services, Food and Drug Administration. Guidance for Industry. Providing Clinical Evidence of Effectiveness for Human Drug and Biological Products. US Department of Health and Human Services, Clinical 6, May 1998.

Declaration of Joseph Kushner IV under 37 CFR 1.132, submitted on Feb. 2, 2017 in U.S. Appl. No. 14/211,659.

U.S. Appl. No. 14/211,659, filed Mar. 14, 2014.

U.S. Appl. No. 15/915,750, filed Mar. 8, 2018.

Maeshima et al., "The JAK Inhibitor Tofacitinib Regulates Synovitis Throught Inhibition of Interferon-y and Interleukin-17 Production by Human CD4+ T Cells", Arthritis & Rheumatism, 64(6), 1790-1798, 2012.

New Technologies and New Dosage Forms of Drugs, Chapter 8, Preparation technologies of sustained release coating and pellets, Section 4, Osmotic pump-type controlled-release preparation, editor in chief: LU Bin, 2nd edition, Beijing: People's Medical Publishing House, May 2005, pp. 436-445.

Notice of Opposition filed by "Aera A/S", against EP 2 968 155 B1, dated Nov. 30, 2021.

FDA label for Xeljanz (tofacitinib), Center For Drug Evaluation and Research, Application No. 203214Orig1s000, Labeling, 2012.

FDA Medical Review for tofacitinib, Center for Drug Evaluation and Research, Application No. 203214Orig1s000, Medical Review(s), 2012.

Lamba, et al., "Extended-Release Once-Daily Formulation of Tofacitinib: Evaluation of Pharmacokinetics Compared With Immediate-Release Tofacitinib and Impact of Food", The Journal of Clinical Pharmacology, 2016, 1362-1371, 56 (11).

Waterman, et al., "Extrudable core system: Development of a single-layer osmotic controlled-release tablet" Journal of Controlled Release, 2009, 201-206, 134.

Notice of Opposition filed by "Dr. Elisabeth Greiner", against EP 2 968 155 B1, dated Dec. 2, 2021.

Flanagan et al., "Discovery of CP-690,550: A Potent and Selective Janus Kinase (JAK) Inhibitor for the Treatment of Autoimmune Diseases and Organ Transplant Rejection", Journal of Medicinal Chemistry, 2010, 8468-8484, 53.

Xeljanz—Highlights of Prescribing Information of Nov. 2012.

Van Gurp, et al., "Phase 1 Dose-Escalation Study of CP-690550 in Stable Renal Allograft Recipients: Preliminary Findings of Safety, Tolerability, Effects of Lymphocyte Subsets and Pharmacokinetics", American Journal of Transplantation, 2008, 1711-1718, 8.

Ahuja, et al., "Osmotic-Controlled Release Oral Delivery System: An Advanced Oral Delivery Form", The Pharma Innovation Journal, 2012, 116-124, 1(7).

Submission of the Proprietor dated Nov. 13, 2018.

Notice of Opposition filed by "Lederer & Keller Patentanwaite Partnerschaft", against EP 2 968 155 B1, dated Dec. 3, 2021.

Bannwarth, et al., "A pharmacokinetic and clinical assessment of tofacitinib for the treatment of rheumatoid arthritis", Expert Opinion on Drug Metabolism & Toxicology, 2013, 753-761, 9(6).

Aulton, "The Science of Dosage Form Design", Pharmaceutics, 2002, 302-304.

Gupta, et al., "Osmotically Controlled Drug Delivery System with Associated Drugs", J. Pharm Pharmaceut Sci, 2010, 571-588, 13(3).

Coleman et al., "Dosing Frequency and Medication Adherence in Chronic Disease", Journal of Managed Care Pharmacy, 2012, 527-539, 18(7).

Chen et al., Challenges and Opportunities in Establishing Scientific and Regulatory Standards for Assuring Therapeutic Equivalence of Modified Release Products: Workshop Summary Report. The AAPS Journal, 2010, 371-377, 12(3).

Notice of Opposition filed by "STADA Arzneimittel AG", against EP 2 968 155 B1, dated Dec. 3, 2021.

(56) References Cited

OTHER PUBLICATIONS

Pfizer Inc., "A Phase 1 Study To Evaluate The Pharmacokinetics (PK), Safety, And Bioavailability Of A Modified-Release (MR) Formulation Of Tofacitinib In Healthy Volunteers", Clinical Trial Record NCT01731327.

Guex, A.C., "Sustained-release Anti-inflammatory Drugs", pharma-kritik, 1990, 9-12, 12(3).

Siew, Adeline, "Controlling Drug Release Through Osmotic Systems", Pharmaceutical Technology, 2013, 37(7).

Keraliya, et al., "Osmotic Drug Delivery System as a Part of Modified Release Dosage Form", International Scholarly Research Network, 2012, 9 pages, Article ID 528079.

Notice of Opposition filed by "Generics [UK] Limited", against EP2 968 155 B1, dated Dec. 3, 2021.

Remington: Essentials of Pharmaceutics, 2013, Chapter 5, 51-61.

EMEA "Note for Guidance on Modified Release Oral and Transdermal Dosage Forms: Section II (Pharmacokinetic and Clinical Evaluation)", 1999, 12 pages.

Notice of Opposition filed by "Teva", against EP 2 968 155 B1, dated Dec. 3, 2021.

Clinical Pharmacology and Biopharmaceutics Review(s), Center For Drug Evaluation and Research, Application No. 203214Orig1s000, 2012.

EMEA "Points to Consider on the Clinical Requirements of Modified Release Products Submitted as a Line Extension of an Existing Marketing Authorisation", 2003, 3 pages.

FDA Guidance for Industry: "SUPAC-MR: Modified Release Solid Oral Dosage Forms", 1997, 52 pages.

Patel, et al., "A Review On Osmotic Drug Delivery System", International Research Journal of Pharmacy, 2012, 38-94, 3(4).

FDA Guidance for Industry: "Providing Clinical Evidence of Effectiveness for Human Drug and Biological Products", 1998, 23 pages.

Peer, "Variability and Impact on Design of Bioequivalence Studies", Basic & Clinical Pharmacology & Toxicology, 2009, 106, 146-153.

Hsu et al., "Long-term management of patients taking immunosuppressive drugs", Australian Prescriber, 2009, 68-71, 32(3).

Expert Report of Dr. Richard Bergstrom. Executed Oct. 9, 2020, 160 pages.

Declaration by Mr. Kushner. Executed Nov. 9, 2018, 9 pages.

TOFACITINIB ORAL SUSTAINED RELEASE DOSAGE FORMS

CROSS REFERENCE TO RELATED APPLICATION

This application is a continuation of U.S. patent application Ser. No. 15/915,750, filed Mar. 8, 2018, now allowed, which is a continuation of U.S. patent application Ser. No. 14/211,659, filed Mar. 14, 2014, now U.S. Pat. No. 9,937,181, which claims the benefit of priority to U.S. Provisional Patent Application No. 61/802,479, filed Mar. 16, 2013, U.S. Provisional Patent Application No. 61/864,059, filed Aug. 9, 2013, and U.S. Provisional Patent Application No. 61/934,428, filed Jan. 31, 2014, each of which is incorporated by reference herein in its entirety.

FIELD OF THE INVENTION

The present invention relates to oral sustained release compositions of 3-((3R,4R)-4-methyl-3-[methyl-(7H-pyrrolo[2,3-d]pyrimidin-4-yl)-amino]-piperidin-1-yl)-3-oxo-propionitrile (hereinafter tofacitinib), which is useful as an inhibitor of protein kinases, such as the enzyme Janus Kinase (JAK) and as such are useful therapy as immunosuppressive agents for organ transplants, xeno transplantation, lupus, multiple sclerosis, rheumatoid arthritis, psoriasis, psoriatic arthritis, Type I diabetes and complications from diabetes, cancer, asthma, atopic dermatitis, autoimmune thyroid disorders, ulcerative colitis, ankylosing spondylitis, juvenile idiopathic arthritis Crohn's disease, Alzheimer's disease, Leukemia, and other indications where immunosuppression would be desirable. The invention provides sustained release formulations comprising tofacitinib or pharmaceutically acceptable salts thereof. The formulations described herein have desirable pharmacokinetic characteristics. Examples include AUC, $C_{max}$, dose-adjusted AUC, dose-adjusted $C_{max}$, and fed/fasted AUC and $C_{max}$ ratios.

BACKGROUND OF THE INVENTION

Tofacitinib, 3-((3R,4R)-4-methyl-3-[methyl-(7H-pyrrolo[2,3-d]pyrimidin-4-yl)-amino]-piperidin-1-yl)-3-oxopropionitrile, has the chemical formula $C_{16}H_{20}N_6O$ and the following structural formula

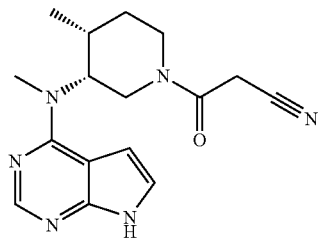 [SMILES: C[C@@H]1CCN(C(=O)CC#N)C[C@@H]1N(C)c1ncnc2[nH]ccc12]

The term "tofacitinib" should be understood, unless otherwise indicated herein, to include any pharmaceutically acceptable form and salts of the compound. Tofacitinib may be present in a crystalline or amorphous form. Tofacitinib, salts of tofacitinib, methods for synthesizing tofacitinib, certain polymorphs of tofacitinib, and certain uses of tofacitinib are disclosed in WO01/42246, WO02/096909, and WO03/048162.

Tofacitinib is generally known to be useful as an inhibitor of protein kinases, such as the enzyme Janus Kinase (JAK) and as such are useful therapy as immunosuppressive agents for organ transplants, xeno transplantation, lupus, multiple sclerosis, rheumatoid arthritis, psoriasis, psoriatic arthritis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable.

Tofacitinib is being developed as an immediate release tablet form with doses ranging from 5 mg to 10 mg administered BID (two times a day). Tofacitinib, as the citrate salt of tofacitinib, is approved in the US under the brand XELJANZ™. Pharmaceutical dosage forms of tofacitinib are known and described in WO01/42246, WO02/096909, and WO03/048162. In addition, WO2012/100949 purports to describe a modified release formulation of tofacitinib. While WO2012/100949 mentions that tofacitinib might be formulated in a modified release formulation, desirable pharmacokinetic characteristics have not been disclosed.

While the commercial immediate release tablet dosage form provides efficacious blood levels of tofacitinib to subjects (dictated by the average blood plasma concentration of tofacitinib, $C_{ave}$, over a 24 hour period), it may be possible to reduce the number of dosings to once daily (QD) with a sustained-release dosage form of tofacitinib while maintaining consistent therapeutic effect, thus enhancing convenience and potentially improving compliance.

Sustained-release dosage forms are typically designed to provide the longest possible duration of release, to minimize: 1) the fluctuations in blood plasma concentration during the dosing interval (i.e. the ratio of the maximum blood plasma concentration, $C_{max,ss}$, to the minimum blood plasma concentration, $C_{min,ss}$, during the dosing interval), and 2) the amount of drug required to achieve the desired therapeutic effect, for the purpose of improving the safety and tolerability profile. For example, WO2012/100949 purports to describe a modified release formulation of tofacitinib having the advantage that tofacitinib is gradually released over a relatively long period at a uniform concentration, which results in little blood level fluctuation in the patient.

However, it was surprisingly found that the bioavailability of tofacitinib is reduced as the duration of release is prolonged, thereby requiring increased amounts of tofacitinib to be administered in the sustained release dosage form to provide efficacious blood levels to subjects.

In addition, the pharmacokinetic profile of the BID immediate release tablets contains periods during a 24 hour time period beneath the IC50 for the JAK1/3 heterodimer signaling ("Drug Holiday"), due to the combination of total drug absorbed and the ratio of the maximum blood plasma concentration, $C_{max,ss}$, to the minimum blood plasma concentration, $C_{min,ss}$, during the dosing interval. Tofacitinib is a selective inhibitor of the Janus kinase (JAK) family of kinases with a high degree of selectivity against other kinases in the human genome. In kinase assays, tofacitinib inhibits JAK1, JAK2, JAK3, and to a lesser extent tyrosine kinase (TyK2). In cellular settings, where JAK kinases signal in pairs, tofacitinib preferentially inhibits cytokines that signal through JAK3 and/or JAK1 including interleukin (IL)-2, -4, -6, -7, -9, -15, -21, and type I and II interferons. These cytokines are pro-inflammatory and integral to lymphocyte function. Inhibition of their signaling may thus result in modulation of multiple aspects of the immune response. Over inhibition of signaling through JAK3 and/or JAK1 could compromise the body's immune system.

It was surprisingly found that the drug holiday period of tofacitinib relative to the IC50 for JAK1/3 signaling during a 24 time period is increased as the release duration from a sustained release dosage form is prolonged. As such, sustained release dosage forms, as described in the prior art, containing tofacitinib would not provide drug holiday periods comparable to the PK profile of the BID immediate release tablets, due to the reduced blood plasma concentrations of tofacitinib exhibited by sustained release dosage forms, as described by the prior art. Accordingly, it was surprisingly found that to provide the optimal PK profile (i.e. optimal exposure and optimal $C_{max,ss}/C_{min,ss}$ ratio while avoiding elevated levels of the maximum blood plasma concentration) for once-daily administration of tofacitinib, dosage forms with shorter durations of sustained release are preferred. It was also surprisingly found that to minimize the total dose of tofacitinib administered to subjects while providing efficacious blood levels in subjects, dosage forms with shorter durations of sustained release are preferred.

SUMMARY OF THE INVENTION

The present invention relates to oral sustained release compositions of tofacitinib for the treatment of anti-inflammatory and auto-immune diseases, and especially Rheumatoid Arthritis (RA). Sustained release of tofacitinib may be accomplished by any means known in the pharmaceutical arts, including but not limited to the use of osmotic dosage forms, matrix dosage forms, multiparticulate dosage forms, gastric retentive dosage forms, and pulsatile dosage forms.

The present invention provides a once daily pharmaceutical dosage form comprising tofacitinib, or a pharmaceutically acceptable salt thereof, and a pharmaceutically acceptable carrier, wherein said dosage form is a sustained release dosage form, and when administered to a subject has a mean area under the plasma concentration versus time curve following administration from about 27 ng-hr/mL per mg of tofacitinib dosed to about 42 ng-hr/mL per mg of tofacitinib dosed and a ratio of geometric mean plasma $C_{max}$ to $C_{min}$ from about 10 to about 100, preferably the ratio of geometric mean plasma $C_{max}$ to $C_{min}$ from about 20 to about 40 and more preferably from about 20 to about 30. The pharmaceutical dosage form may comprise from about 10 mg to about 12 mg of tofacitinib, preferably 11 mg of tofacitinib. In another embodiment, the pharmaceutical dosage form may comprise from about 20 to about 24 mg of tofacitinib, preferably 22 mg of tofacitinib. The pharmaceutical dosage form of the invention also provides the subject a single, continuous time above about 17 ng/ml from about 6 to about 15 hours and a single, continuous time below about 17 ng/ml from about 9 to about 18 hours over a 24 hour dosing interval. In another embodiment of the invention, the subject has a single, continuous time above about 17 ng/ml from about 6 to about 9 hours. In another embodiment of the invention, the subject has a single, continuous time below about 17 ng/ml from about 15 to about 18 hours. In another embodiment of the invention, the subject has a single, continuous time above about 17 ng/ml from about 11 to about 15 hours. In another embodiment of the invention, the subject has a single, continuous time below about 17 ng/ml from about 9 to about 13 hours.

In another embodiment, the pharmaceutical dosage form of the present invention may provide a subject having a mean maximum plasma concentration ($C_{max}$) from about 3 ng/mL per mg to about 6 ng/mL per mg of tofacitinib dosed.

The present invention also provides a once daily pharmaceutical dosage form comprising tofacitinib, or a pharmaceutically acceptable salt thereof, and a pharmaceutically acceptable carrier, wherein said dosage form is a sustained release dosage form, and when administered to a subject has a mean area under the plasma concentration versus time curve following administration from about 17 ng-hr/mL per mg of tofacitinib dosed to about 42 ng-hr/mL per mg of tofacitinib dosed and a ratio of geometric mean plasma $C_{max}$ to $C_{min}$ from about 10 to about 100, preferably the ratio of geometric mean plasma $C_{max}$ to $C_{min}$ from about 20 to 40 and more preferably about 20 to 30. The pharmaceutical dosage form may comprise from about 10 mg to about 12 mg of tofacitinib, preferably 11 mg of tofacitinib. In another embodiment, the pharmaceutical dosage form may comprise from about 20 to about 24 mg of tofacitinib, preferably 22 mg of tofacitinib. The pharmaceutical dosage form of the invention also provides the subject a single, continuous time above about 17 ng/ml from about 6 to about 15 hours and a single, continuous time below about 17 ng/ml from about 9 to about 18 hours over a 24 hour dosing interval. In another embodiment of the invention, the subject has a single, continuous time above about 17 ng/ml from about 6 to about 9 hours. In another embodiment of the invention, the subject has a single, continuous time below about 17 ng/ml from about 15 to about 18 hours. In another embodiment of the invention, the subject has a single, continuous time above about 17 ng/ml from about 11 to about 15 hours. In another embodiment of the invention, the subject has a single, continuous time below about 17 ng/ml from about 9 to about 13 hours. In another embodiment, the pharmaceutical dosage form of the present invention may provide a subject having a mean maximum plasma concentration ($C_{max}$) from about 3 ng/mL per mg to about 6 ng/mL per mg of tofacitinib dosed.

The present invention additionally provides a once daily pharmaceutical dosage form comprising tofacitinib, or a pharmaceutically acceptable salt thereof, and a pharmaceutically acceptable carrier, wherein said dosage form is a sustained release dosage form, and when administered orally to a subject has a mean steady-state minimum plasma concentration ($C_{min}$) less than about 0.3 ng/mL per mg of tofacitinib dosed.

In another embodiment, the present invention provides a once daily pharmaceutical dosage form comprising tofacitinib, or a pharmaceutically acceptable salt thereof, and a pharmaceutically acceptable carrier, wherein said dosage form is a sustained release dosage form, and when administered orally to a subject has a mean fed/fasted ratio of the area under the plasma concentration versus time curve of about 0.7 to about 1.4 and a mean fed/fasted ratio of the maximum plasma concentration ($C_{max}$) of about 0.7 to about 1.4, preferably about 0.8 to about 1.25.

In another embodiment, the present invention provides a pharmaceutical dosage form comprising tofacitinib, or a pharmaceutically acceptable salt thereof, and a pharmaceutically acceptable carrier, wherein said dosage form is a sustained release dosage form, and when added to a test medium comprising 900 mL of 0.05M pH 6.8 potassium phosphate buffer at 37° C. in a standard USP rotating paddle apparatus and the paddles are rotated at 50 rpm, dissolves not more than 30% of the drug in 1 hour, and not less than 35% and not more than 75% of the drug in 2.5 hours and not less than 75% of the tofacitinib in 5 hours; preferably not more than 25% of the drug in 1 hour, and not less than 40% and not more than 70% of the drug in 2.5 hours.

In another embodiment, the present invention provides a pharmaceutical dosage form comprising tofacitinib, or a pharmaceutically acceptable salt thereof, and a pharmaceutically acceptable carrier, wherein the dosage form is a sustained release dosage form and when administered orally to a subject provides an AUC in the range of 80% to 125% of the AUC of an amount of tofacitinib administered as an immediate release formulation BID and wherein the sustained release dosage form provides a ratio of geometric mean plasma $C_{max}$ to $C_{min}$ from about 10 to about 100, preferably the AUC may be in the range of 90% to 110% and the ratio of geometric mean plasma concentration $C_{max}$ to $C_{min}$ may be from about 20 to about 40 and more preferably from about 20 to about 30.

In another embodiment, the pharmaceutical dosage form of the present invention may also provide a mean plasma $C_{max}$ in the range of 70% to 125% of the mean plasma $C_{max}$ of tofacitinib administered as an immediate release formulation BID at steady state when administered orally to a subject. In another embodiment, the pharmaceutical dosage form of the present invention provides a drug holiday in the range of 80% to 110% of the drug holiday of tofacitinib administered as an immediate release formulation BID over a 24 hour period when administered orally to a subject. The pharmaceutical dosage form of the present invention may comprise from about 10 mg to about 12 mg of tofacitinib and the equivalent amount of tofacitinib administered as an immediate release formulation BID is 5 mg, preferably the pharmaceutical dosage form comprises 11 mg of tofacitinib. The pharmaceutical dosage form of the present invention may comprise from about 20 mg to about 24 mg of tofacitinib and the equivalent amount of tofacitinib administered as the immediate release formulation BID is 10 mg, preferably the pharmaceutical dosage form may comprise 22 mg of tofacitinib. In an another embodiment, the pharmaceutical dosage form of the present invention provides the drug holiday from about 15 to about 18 hours over the 24 hour period. In an another embodiment, the pharmaceutical dosage form of the present invention provides the drug holiday from about 9 to about 13 hours over the 24 hour period.

The present invention also provides for pharmaceutical compositions to achieve these sustained delivery formulations. In one embodiment, the sustained release pharmaceutical dosage form of the present invention comprising a core containing tofacitinib, or a pharmaceutically acceptable salt thereof, and a semi-permeable membrane coating wherein said coating comprises substantially of a water-insoluble polymer. The sustained release dosage form of the present invention may deliver tofacitinib primarily by osmotic pressure. In another embodiment of the present invention, the sustained release dosage form of the present invention may comprise a delivery system selected from the group consisting of an extrudable core system, swellable core system, or asymmetric membrane technology.

In another embodiment, the water insoluble polymer comprises a cellulose derivative, preferably cellulose acetate. In another embodiment of the present invention, the coating further comprising a water soluble polymer having an average molecular weight between 2000 and 100,000 daltons. In another embodiment of the present invention the water soluble polymer is selected from the group consisting of water soluble cellulose derivatives, acacia, dextrin, guar gum, maltodextrin, sodium alginate, starch, polyacrylates, and polyvinyl alcohols. In another embodiment of the present invention, the water soluble cellulose derivatives comprises hydroxypropylcellulose, hydroxypropylmethylcellulose or hydroxyethylcellulose.

In another embodiment of the present invention, the core comprises a sugar, preferably sorbitol.

In another embodiment the sustained release pharmaceutical dosage form of the present invention, comprising tofacitinib, or a pharmaceutically acceptable salt thereof, and a pharmaceutically acceptable carrier wherein said tofacitinib is embedded in a matrix which releases tofacitinib by diffusion. In one embodiment, a portion of the outside surface of the matrix is covered with an impermeable coating and the remainder of the outside surface is uncovered.

In another embodiment of the present invention, the dosage form is in the form of a tablet and the uncovered surface is in the form of an opening through the impermeable coating.

In another embodiment of the present invention, the dosage form is in the form of a tablet and the uncovered surface is in the form of a passageway which penetrates through the entire tablet.

In another embodiment of the present invention, the dosage form is in the form of a tablet and the uncovered surface is in the form of one or more slits through said impermeable coating or in the form of one or more strips removed therefrom.

In another embodiment of the present invention, the matrix of the dosage form remains substantially intact during the period of tofacitinib release.

In another embodiment of the present invention, the pharmaceutically acceptable carrier comprising the matrix material is selected from the group consisting of waxes, long chain alcohols, fatty acid esters, glycolized fatty acid esters, phosphoglycerides, polyoxyethylene alkyl ethers, long chain carboxylic acids, sugar alcohols, and mixtures thereof.

In another embodiment of the present invention, the outside surface of said matrix is covered with an enteric coating. The matrix may be formed as a melt-congealed core.

In another embodiment of the present invention, the matrix of the dosage form comprises hydroxypropyl methylcellulose.

In another embodiment of the present invention, tofacitinib is embedded in a matrix which releases tofacitinib by eroding.

In another embodiment of the present invention, the matrix of the dosage form comprises hydroxypropyl methylcellulose.

In another embodiment of the present invention, the matrix of the dosage form comprises poly (ethylene oxide).

In another embodiment of the present invention, the matrix of the dosage form comprises polyacrylic acid.

In another embodiment of the present invention, a reservoir of tofacitinib is encased in a membrane which limits the release rate of tofacitinib by diffusion.

In another embodiment the sustained release pharmaceutical dosage form of the present invention provides a dosage form in the form of a tablet coated with a membrane.

In another embodiment the sustained release pharmaceutical dosage form of the present invention provides a dosage form in the form of a multiparticulate comprising particles, which particles are independently coated with a membrane which limits the release rate of tofacitinib by diffusion.

The present invention also provides a method of treating immunological disorders in a subject comprising administering to the subject in need thereof the sustained release pharmaceutical dosage form of the present invention in an amount effective in treating such disorders. The immunological disorder is selected from the group consisting of organ transplants, xeno transplantation, lupus, multiple sclerosis, rheumatoid arthritis, psoriasis, Type I diabetes and complications from diabetes, cancer, asthma, atopic dermatitis, autoimmune thyroid disorders, ulcerative colitis, ankylosing spondylitis, juvenile idiopathic arthritis Crohn's disease, psoriatic arthritis, Alzheimer's disease, and Leukemia, preferably, the immunological disorder is selected from the group consisting of organ transplant, rheumatoid arthritis, psoriasis, psoriatic arthritis, ulcerative colitis, ankylosing spondylitis, juvenile idiopathic arthritis and Crohn's disease. In another embodiment of the present invention the method further comprising one or more additional agents which modulate a mammalian immune system or with anti-inflammatory agents. The additional agent may be selected from the group consisting of a nonbiologic DMARD, methotrexate, glucocorticoid, glucocorticoid receptor agonist, leflunomide, non-steroidal anti-inflammatory drugs, 6-mercaptopurine, azathioprine, sulfasalazine, and 5-aminosalicylate drugsm, preferably the additional agent is selected from the group consisting of a nonbiologic DMARD and a glucocorticoid receptor agonist, more preferably the additional agent is methotrexate.

The present invention also provides a method of treating atherosclerosis in a subject comprising administering to the subject in need thereof the sustained release pharmaceutical of the present invention in an amount effective in treating atherosclerosis. In another embodiment of the present invention, the method further comprises administering a HMG-CoA reductase inhibitor, preferably the HMG-CoA reductase inhibitor is atorvastatin or a pharmaceutically acceptable salt thereof.

The term "tofacitinib" should be understood, unless otherwise indicated herein, to include any pharmaceutically acceptable form and salts of the compound. Tofacitinib may be present in crystalline or amorphous form. The present invention relates to a sustained release dosage form of tofacitinib to enable once a day administration to provide specific pharmacokinetic properties for the purpose of: 1) minimizing the amount of tofacitinib in the sustained release dosage form required to achieve efficacious blood levels in subjects, 2) optimizing the extent of tofacitinib binding to the JAK 1/3 heterodimers (as measured by 1050, which occurs in humans at drug plasma concentrations of about 17 ng/ml or 56 nM as reported in Meyer D M, Jesson M I, Xiong L, et al. Anti-inflammatory activity and neutrophil reduction mediated by the JAK1/JAK3 inhibitor, CP-690,550, in rat adjuvant-induced arthritis J. of Inflammation 2010; 7:41, which is incorporated herein by reference), which regulates the immune response, to provide the desired level of efficacy (based on the mean $C_{ave}$) over a 24-hour dosing interval. The sustained release dosage form of the present invention is one that provides the above desired pharmacokinetic properties, and in particular the once daily dosage properties recited above. Preferably the sustained release dosage form of the invention does not significantly alter the pharmacokinetic profile of tofacitinib when administered in the fed state (i.e. exhibits a lack of food effect), as this minimizes deviation from the optimal coverage of JAK 1/3 heterodimers.

By "sustained release" is meant broadly that tofacitinib is released from an oral dosage form at a rate that is slower than immediate release. Oral dosage form is intended to embrace tablets, capsules, multiparticulates or beads. "Sustained release" is intended to embrace an oral composition that consists of either one or a combination of the following:
a) a controlled release component alone;
b) a delayed release and controlled release component;
c) a delayed release and immediate release component By "pharmaceutically acceptable form" is meant any pharmaceutically acceptable form, including, solvates, hydrates, isomorphs, polymorphs, co-crystals, pseudomorphs, neutral forms, acid addition salt forms, and prodrugs. The pharmaceutically acceptable acid addition salts of tofacitinib are prepared in a conventional manner by treating a solution or suspension of the free base with about one or two chemical equivalents of a pharmaceutically acceptable acid. Conventional concentration and recrystallization techniques are employed in isolating the salts. Illustrative of suitable acids are acetic, lactic, succinic, maleic, tartaric, citric, gluconic, ascorbic, mesylic, tosylic, benzoic, cinnamic, fumaric, sulfuric, phosphoric, hydrochloric, hydrobromic, hydroiodic, sulfamic, sulfonic such as methanesulfonic, benzenesulfonic, and related acids. Some preferred forms of tofacitinib include the free base and tofacitinib citrate.

The terms "subject", "patient" and "individual" are used interchangeably herein to refer to a vertebrate, preferably a mammal, more preferably a human.

The "solid oral dosage form" of the present invention is a pharmaceutically-acceptable solid oral dosage form, meaning that the dosage form is safe for administration to humans and all excipients in the dosage form are pharmaceutically-acceptable, in other words safe for human ingestion.

The term "fasted" as used herein is defined as follows: the dosing state which is defined following an overnight fast (wherein 0 caloric intake has occurred) of at least 10 hours. Subjects may administer the dosage form with 240 mL of water. No food should be allowed for at least 4 hours post-dose. Water may be allowed as desired except for one hour before and after drug administration.

The term "fed" as used herein is defined as follows: the dosing state which is defined following an overnight fast (wherein 0 caloric intake has occurred) of at least 10 hours, subjects then begin the recommended high fat meal 30 minutes prior to administration of the drug product. Subjects should eat this meal in 30 minutes or less; however the drug product should be administered 30 minutes after the start of the meal. The drug product may be administered with 240 mL of water. No food should be allowed for at least 4 hours post-dose. Water may be allowed as desired except for one hour before and after drug administration. A high fat (approximately 50 percent of the total caloric content of the meal is derived from fat) and high calorie (approximately 800 to 1000 calories) meal should be used as the test meal under the fed condition. This test meal should derive approximately 150, 250, and 500-600 calories from protein, carbohydrate, and fat respectively. An example test meal would be two eggs fried in butter, two strips of bacon, two slices of toast with butter, four ounces of hash brown potatoes and eight ounces of whole milk.

The calculation of the mean area under the serum concentration versus time curve (AUC) is a well-known procedure in the pharmaceutical arts and is described, for example, in Welling, "Pharmacokinetics Processes and Mathematics," ACS Monograph 185 (1986). AUC as used herein includes area under the concentration-time curve from time zero extrapolated to infinite time following single dose or the area under the concentration-time curve from time zero to time of the end of dosing interval following steady state/multiple dose. In addition, the calculations for $C_{max}$, $C_{min,ss}$, $T_{max}$, and elimination half-life (t½), are also known to this of ordinary skill in the art and is described, for example, in Shargel, Wu-Pong, and Yu, Applied Biopharmaceutics and Pharmacokinetics (2005). To determine the mean fed/fasted ratio, the individual ratio of the mean area under the plasma concentration versus time curve of tofacitinib (e.g. $AUC_{0-inf}$) in the fed state to the mean area under the plasma concentration versus time curve of tofacitinib (e.g. $AUC_{0-inf}$) in the fasted state is first calculated, and then the corresponding individual ratios are averaged together. In this way, it is the average of each corresponding individual's ratio which is determined.

"Dissolution Test 1" refers to the following test of dosage forms of tofacitinib. The dissolution test is conducted in a standard USP rotating paddle apparatus as disclosed in United States Pharmacopoeia (USP) Dissolution Test Chapter 711, Apparatus 2. Paddles are rotated at 50 rpm and the dosage form is added to 900 mL of 0.05M pH 6.8 potassium phosphate buffer at 37° C. At appropriate times following test initiation (e.g., insertion of the dosage form into the apparatus), filtered aliquots (typically 1.5 mL) from the test medium are analyzed for tofacitinib by high performance liquid chromatography (HPLC). Dissolution results are reported as the percent of the total dose of tofacitinib tested dissolved versus time.

DETAILED DESCRIPTION OF THE INVENTION

The present invention relates to oral sustained release compositions of tofacitinib for the treatment of anti-inflammatory and auto-immune diseases, and especially Rheumatoid Arthritis (RA). Sustained release of tofacitinib may be accomplished by any means known in the pharmaceutical arts, including but not limited to the use of osmotic dosage forms, matrix dosage forms, multiparticulate dosage forms, gastric retentive dosage forms, and pulsatile dosage forms.

Sustained Release—Matrix Systems (Tablets)

In one embodiment, tofacitinib is incorporated into an erodible or non-erodible polymeric matrix tablet. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous use environment, the erodible polymeric matrix imbibes water and forms an aqueous-swollen gel or "matrix" that entraps the tofacitinib. The aqueous-swollen matrix gradually erodes, swells, disintegrates, disperses or dissolves in the environment of use, thereby controlling the release of tofacitinib to the environment of use. Examples of such dosage forms are well known in the art. See, for example, Remington: The Science and Practice of Pharmacy, 20th Edition, 2000.

A key ingredient of the water-swollen matrix is the water-swellable, erodible, or soluble polymer, which may generally be described as an osmopolymer, hydrogel or water-swellable polymer. Such polymers may be linear, branched, or crosslinked. They may be homopolymers or copolymers. Exemplary polymers include naturally occurring polysaccharides such as chitin, chitosan, dextran and pullulan; gum agar, gum arabic, gum karaya, locust bean gum, gum tragacanth, carrageenans, gum ghatti, guar gum, xanthan gum and scleroglucan; starches such as dextrin and maltodextrin; hydrophilic colloids such as pectin; alginates such as ammonium alginate, sodium, potassium or calcium alginate, propylene glycol alginate; gelatin; collagen; and cellulosics. By "cellulosics" is meant a cellulose polymer that has been modified by reaction of at least a portion of the hydroxyl groups on the saccharide repeat units with a compound to form an ester-linked or an ether-linked substituent. For example, the cellulosic ethyl cellulose has an ether linked ethyl substituent attached to the saccharide repeat unit, while the cellulosic cellulose acetate has an ester linked acetate substituent.

Cellulosics for the erodible matrix comprise aqueous-soluble and aqueous-erodible cellulosics such as ethyl cellulose (EC), methylethyl cellulose (MEC), carboxymethyl cellulose (CMC), carboxymethyl ethylcellulose (CMEC), hydroxyethyl cellulose (HEC), hydroxypropyl cellulose (HPC), cellulose acetate phthalate (CAP), cellulose acetate trimellitate (CAT), hydroxypropyl methyl cellulose (HPMC), hydroxypropyl methyl cellulose phthalate (HPMCP), hydroxypropyl methyl cellulose acetate succinate (HPMCAS), hydroxypropyl methyl cellulose acetate trimellitate (HPMCAT), and ethylhydroxy ethylcellulose (EHEC).

A particularly preferred class of such cellulosics comprises various grades of low viscosity (MW less than or equal to 50,000 daltons) and high viscosity (MW greater than 50,000 daltons) HPMC. Commercially available low viscosity HPMC polymers include the Dow METHOCEL™ series E3, E5, E15LV, E50LV and K100LV, while high viscosity HPMC polymers include E4MCR, E10MCR, K4M, K15M and K100M; especially preferred in this group are the METHOCEL™ K series. Other commercially available types of HPMC include the Shin Etsu METOLOSE™ 90SH series. In one embodiment, the HPMC has a low viscosity, meaning that the viscosity of a 2% (w/v) solution of the HPMC in water is less than about 120 cp. A preferred HPMC is one in which the viscosity of a 2% (w/v) solution of the HPMC in water ranges from 80 to 120 cp (such as METHOCEL™ K100LV).

Other materials useful as the erodible matrix material include, but are not limited to, pullulan, polyvinyl pyrrolidone, polyvinyl alcohol, polyvinyl acetate, glycerol fatty acid esters, polyacrylamide, polyacrylic acid, copolymers of ethacrylic acid or methacrylic acid (EUDRAGIT®, Rohm America, Inc., Piscataway, N.J.) and other acrylic acid derivatives such as homopolymers and copolymers of butylmethacrylate, methylmethacrylate, ethylmethacrylate, ethylacrylate, (2-dimethylaminoethyl)methacrylate, and (trimethylaminoethyl) methacrylate chloride.

The erodible matrix polymer may also contain additives and excipients known in the pharmaceutical arts, including osmopolymers, osmagens, solubility-enhancing or—retarding agents and excipients that promote stability or processing of the dosage form.

In a non-erodible matrix system, tofacitinib is distributed in an inert matrix. The drug is released by diffusion through the inert matrix. Examples of materials suitable for the inert matrix include insoluble plastics, such as copolymers of ethylene and vinyl acetate, methyl acrylate-methyl methacrylate copolymers, polyvinyl chloride, and polyethylene; hydrophilic polymers, such as ethyl cellulose, cellulose acetate, and crosslinked polyvinylpyrrolidone (also known as crospovidone); and fatty compounds, such as carnauba wax, microcrystalline wax, and triglycerides. Such dosage forms are described further in Remington: The Science and Practice of Pharmacy, 20th edition (2000).

Sustained Release—Matrix Systems (Multiparticulates)

In another embodiment, a matrix multiparticulate, comprises a plurality of tofacitinib-containing particles, each particle comprising a mixture of tofacitinib with one or more excipients selected to form a matrix capable of limiting the dissolution rate of the tofacitinib into an aqueous medium. The matrix materials useful for this embodiment are generally water-insoluble materials such as waxes, cellulose, or other water-insoluble polymers. If needed, the matrix materials may optionally be formulated with water-soluble materials which can be used as binders or as permeability-modifying agents. Matrix materials useful for the manufacture of these dosage forms include microcrystalline cellulose such as Avicel (registered trademark of FMC Corp., Philadelphia, Pa.), including grades of microcrystalline cellulose to which binders such as hydroxypropyl methyl cellulose have been added, waxes such as paraffin, modified vegetable oils, carnauba wax, hydrogenated castor oil, beeswax, and the like, as well as synthetic polymers such as poly(vinyl chloride), poly(vinyl acetate), copolymers of vinyl acetate and ethylene, polystyrene, and the like. Water soluble binders or release modifying agents which can optionally be formulated into the matrix include water-soluble polymers such as hydroxypropyl cellulose (HPC), hydroxypropyl methyl cellulose (HPMC), methyl cellulose, poly (N-vinyl-2-pyrrolidinone) (PVP), poly(ethylene oxide) (PEO), poly(vinyl alcohol) (PVA), xanthan gum, carrageenan, and other such natural and synthetic materials. In addition, materials which function as release-modifying agents include water-soluble materials such as sugars or salts. Preferred water-soluble materials include lactose, sucrose, glucose, and mannitol, as well as HPC, HPMC, and PVP.

A process for manufacturing matrix multiparticulates is the extrusion/spheronization process. For this process, the tofacitinib is wet-massed with a binder, extruded through a perforated plate or die, and placed on a rotating disk. The extrudate ideally breaks into pieces which are rounded into spheres, spheroids, or rounded rods on the rotating plate. Another process and composition for this method involves using water to wet-mass a blend comprising about 20 to 75% of micro-crystalline cellulose blended with, correspondingly, about 80 to 25% tofacitinib.

Another process for manufacturing matrix multiparticulates is the preparation of wax granules. In this process, a desired amount of tofacitinib is stirred with liquid wax to form a homogeneous mixture, cooled and then forced through a screen to form granules. Preferred matrix materials are waxy substances. Some preferred waxy substances are hydrogenated castor oil and carnauba wax and stearyl alcohol.

A further process for manufacturing matrix multiparticulates involves using an organic solvent to aid mixing of the tofacitinib with the matrix material. This technique can be used when it is desired to utilize a matrix material with an unsuitably high melting point that, if the material were employed in a molten state, would cause decomposition of the drug or of the matrix material, or would result in an unacceptable melt viscosity, thereby preventing mixing of tofacitinib with the matrix material. Tofacitinib and matrix material may be combined with a modest amount of solvent to form a paste, and then forced through a screen to form granules from which the solvent is then removed. Alternatively, tofacitinib and matrix material may be combined with enough solvent to completely dissolve the matrix material and the resulting solution (which may contain solid drug particles) spray dried to form the particulate dosage form. This technique is preferred when the matrix material is a high molecular weight synthetic polymer such as a cellulose ether or cellulose ester. Solvents typically employed for the process include acetone, ethanol, isopropanol, ethyl acetate, and mixtures of two or more.

In one embodiment, the matrix multiparticulates are formed by the melt spray congeal process. The melt-congeal core comprises a matrix material. The matrix material serves two functions. First, the matrix material allows formation of relatively smooth, round cores that are amenable to coating. Second, the matrix material binds the optional excipients and/or drugs that may be incorporated into the core. The matrix material has the following physical properties: a sufficiently low viscosity in the molten state to form multiparticulates, as detailed below; and rapidly congeals to a solid when cooled below its melting point. For those multiparticulates incorporating drug in the core, the matrix preferably has a melting point below that of the melting point or decomposition point of the drug, and does not substantially dissolve the drug.

The melt-congeal cores consist essentially of a continuous phase of matrix material and optionally other excipients, with optional drug particles and optional swelling agent particles encapsulated within. Because of this, a sufficient amount of matrix material must be present to form smooth cores that are large enough to coat. In the case of cores containing solid particles, such as drug or swelling agent, the core must contain a sufficient amount of matrix material to encapsulate the drug and swelling agent to form relatively smooth and spherical cores, which are more easily coated by conventional spray-coating processes than irregularly-shaped ones. The matrix material may be present in the core from at least about 30 wt percent, at least about 50 wt percent, at least about 70 wt percent, at least about 80 wt percent, at least about 90 wt percent, and up to 100 wt percent based on the mass of the uncoated core.

In order to form small, smooth round cores, the matrix material must be capable of being melted and then atomized. The matrix material or mixture of materials is solid at 25 degrees C. However, the matrix material melts, or is capable of melting with the addition of an optional processing aid, at a temperature of less than 200 degrees centigrade so as to be suitable for melt-congeal processing described below. Preferably, the matrix material has a melting point between 50 degrees C. and 150° C. Although the term "melt" generally refers to the transition of a crystalline material from its crystalline to its liquid state, which occurs at its melting point, and the term "molten" generally refers to such a crystalline material in its fluid state, as used herein, the terms are used more broadly. In the case of "melt," the term is used to refer to the heating of any material or mixture of materials sufficiently that it becomes fluid in the sense that it may be pumped or atomized in a manner similar to a crystalline material in the fluid state. Likewise "molten" refers to any material or mixture of materials that is in such a fluid state.

The matrix material is selected from the group consisting of waxes, long chain alcohols ($C_{12}$ or greater), fatty acid esters, glycolized fatty acid esters, phosphoglycerides, polyoxyethylene alkyl ethers, long chain carboxylic acids ($C_{12}$ or greater), sugar alcohols, and mixtures thereof. Exemplary matrix materials include highly purified forms of waxes, such as Carnauba wax, white and yellow beeswax, ceresin wax, microcrystalline wax, and paraffin wax; long-chain alcohols, such as stearyl alcohol, cetyl alcohol and polyethylene glycol; fatty acid esters (also known as fats or glycerides), such as isopropyl palmitate, isopropyl myristate, glyceryl monooleate, glyceryl monostearate, glyceryl palmitostearate, mixtures of mono-, di-, and trialkyl glycerides, including mixtures of glyceryl mono-, di-, and tribehenate, glyceryl tristearate, glyceryl tripalmitate and hydrogenated vegetable oils, including hydrogenated cottonseed oil; glycolized fatty acid esters, such as polyethylene glycol stearate and polyethylene glycol distearate; polyoxyethylene alkyl ethers; polyethoxylated castor oil derivatives; long-chain carboxylic acids such as stearic acid; and sugar alcohols such as mannitol and erythritol. The matrix material may comprise mixtures of materials, such as mixtures of any of the foregoing.

The core may also contain a variety of other excipients, present in the core in an amount of from 0 to 40 wt percent, based upon the mass of the uncoated core. One preferred excipient is a dissolution enhancer, which may be used to increase the rate of water uptake by the core and consequent expansion of the swelling agent. The dissolution enhancer is a different material than the matrix material. The dissolution enhancer may be in a separate phase or a single phase with the matrix material. Preferably, at least a portion of the dissolution enhancer is phase-separated from the matrix material. As water enters the core, the dissolution-enhancer dissolves, leaving channels which allow water to more rapidly enter the core. In general, dissolution enhancers are amphiphilic compounds and are generally more hydrophilic than the matrix materials. Examples of dissolution enhancers include: surfactants such as poloxamers, docusate salts, polyoxyethylene castor oil derivatives, polysorbates, sodium lauryl sulfate, and sorbitan monoesters; sugars, such as glucose, xylitol, sorbitol and maltitol; salts, such as sodium chloride, potassium chloride, lithium chloride, calcium chloride, magnesium chloride, sodium sulfate, potassium sulfate, sodium carbonate, magnesium sulfate and potassium phosphate; and amino acids, such as alanine and glycine; and mixtures thereof. One surfactant-type dissolution-enhancer is a poloxambetar (commercially available as the LUTROL or PLURONIC series from BASF Corp.).

The core may also contain other optional excipients, such as agents that inhibit or delay the release of drug from the multiparticulates. Such dissolution-inhibiting agents are generally hydrophobic and include dialkylphthalates such as dibutyl phthalate, and hydrocarbon waxes, such as microcrystalline wax and paraffin wax. Another useful class of excipients comprises materials that may be used to adjust the viscosity of the molten feed used to form the cores. Such viscosity-adjusting excipients will generally make up 0 to 25 wt percent of the core. The viscosity of the molten feed is a key variable in obtaining cores with a narrow particle size distribution. For example, when a spinning-disk atomizer is employed, it is preferred that the viscosity of the molten mixture be at least about 1 cp and less than about 10,000 cp, preferably at least 50 cp and less than about 1000 cp. If the molten mixture has a viscosity outside these ranges, a viscosity-adjusting agent can be added to obtain a molten mixture within the viscosity range. Examples of viscosity-reducing excipients include stearyl alcohol, cetyl alcohol, low molecular weight polyethylene glycol (i.e., less than about 1000 daltons), isopropyl alcohol, and water. Examples of viscosity-increasing excipients include microcrystalline wax, paraffin wax, synthetic wax, high molecular weight polyethylene glycols (i.e., greater than about 5000 daltons), ethyl cellulose, hydroxypropyl cellulose, hydroxypropyl methyl cellulose, methyl cellulose, silicon dioxide, microcrystalline cellulose, magnesium silicate, sugars, and salts.

For those embodiments containing a drug in the core, other excipients may be added to adjust the release characteristics of the drug from the cores. For example, an acid or base may be included in the composition to modify the rate at which drug is released in an aqueous use environment. Examples of acids or bases that can be included in the composition include citric acid, adipic acid, malic acid, fumaric acid, succinic acid, tartaric acid, di- and tribasic sodium phosphate, di- and tribasic calcium phosphate, mono-, di-, and triethanolamine, sodium bicarbonate and sodium citrate dihydrate. Such excipients may make up 0 to 25 wt percent of the core, based on the total mass of the core.

Still other excipients may be added to improve processing, such as excipients to reduce the static charge on the cores or to reduce the melting temperature of the matrix material. Examples of such anti-static agents include talc and silicon dioxide. Flavorants, colorants, and other excipients may also be added in their usual amounts for their usual purposes. Such excipients may make up 0 to 25 wt percent of the core, based on the total mass of the core.

The multiparticulates are made via a melt-congeal process comprising the steps: (a) forming a molten mixture comprising the drug, the glyceride (or other waxes), and any release modifying agents; (b) delivering the molten mixture of step (a) to an atomizing means to form droplets from the molten mixture; and (c) congealing the droplets from step (b) to form multiparticulates.

The processing conditions are chosen to maintain the crystallinity of the drug. The temperature of the molten mixture is kept below the melting point of the drug. Preferably, at least 70 wt percent of the drug remains crystalline within the molten feed, more preferably, at least 80 wt percent and most preferably at least 90 wt percent.

The term "molten mixture" as used herein refers to a mixture of drug, glyceride (or other waxes), and any release modifying agents required heated sufficiently that the mixture becomes sufficiently fluid that the mixture may be formed into droplets or atomized. Atomization of the molten mixture may be carried out using any of the atomization methods described below. Generally, the mixture is molten in the sense that it will flow when subjected to one or more forces such as pressure, shear, and centrifugal force, such as that exerted by a centrifugal or spinning-disk atomizer. Thus, the drug/glyceride/release-modifying agent mixture may be considered "molten" when any portion of the drug/glyceride/release-modifying agent mixture becomes sufficiently fluid that the mixture, as a whole, may be atomized. Generally, a mixture is sufficiently fluid for atomization when the viscosity of the molten mixture is less than about 20,000 cp. Often, the mixture becomes molten when the mixture is heated above the melting point of the glyceride/release-modifying agent mixture, in cases where the glyceride/release-modifying agent mixture is sufficiently crystalline to have a relatively sharp melting point; or, when the glyceride/release-modifying agent mixture is amorphous, above the softening point of the glyceride/release-modifying agent mixture. The molten mixture is therefore often a suspension of solid particles in a fluid matrix. In one preferred embodiment, the molten mixture comprises a mixture of substantially crystalline drug particles suspended in a glyceride/release-modifying agent mixture that is substantially fluid. In such cases, a portion of the drug may be dissolved in the glyceride/release-modifying agent mixture and a portion of the glyceride/release-modifying agent mixture may remain solid.

Virtually any process may be used to form the molten mixture. One method involves heating the glyceride/release-modifying agent mixture in a tank until it is fluid and then adding the drug to the molten glyceride/release-modifying agent mixture. Generally, the glyceride/release-modifying agent mixture is heated to a temperature of about 10 degrees C. or more above the temperature at which it becomes fluid. When one or more of the glyceride/release-modifying agent components is crystalline, this is generally about 10 degrees C. or more above the melting point of the lowest melting point material of the mixture. The process is carried out so that at least a portion of the feed remains fluid until atomized. Once the glyceride/release-modifying agent mixture has become fluid, the drug may be added to the fluid carrier or "melt." Although the term "melt" generally refers specifically to the transition of a crystalline material from its crystalline to its liquid state, which occurs at its melting point, and the term "molten" generally refers to such a crystalline material in its fluid state, as used herein, the terms are used more broadly, referring in the case of "melt" to the heating of any material or mixture of materials sufficiently that it becomes fluid in the sense that it may be pumped or atomized in a manner similar to a crystalline material in the fluid state. Likewise "molten" refers to any material or mixture of materials that is in such a fluid state. Alternatively, the drug, the glyceride (or other wax), and the release-modifying agent may be added to the tank and the mixture heated until the mixture has become fluid.

Once the glyceride/release-modifying agent mixture has become fluid and the drug has been added, the molten mixture is mixed to ensure the drug is uniformly distributed therein. Mixing is generally done using mechanical means, such as overhead mixers, magnetically driven mixers and stir bars, planetary mixers, and homogenizers. Optionally, the contents of the tank can be pumped out of the tank and through an in-line, static mixer or extruder and then returned to the tank. The amount of shear used to mix the molten feed should be sufficiently high to ensure uniform distribution of the drug in the molten carrier. The amount of shear is kept low enough so the form of the drug does not change, i.e., so as to cause an increase in the amount of amorphous drug or a change in the crystalline form of the drug. It is also preferred that the shear not be so high as to reduce the particle size of the drug crystals. The molten mixture can be mixed from a few minutes to several hours, the mixing time being dependent on the viscosity of the feed and the solubility of drug and any optional excipients in the carrier.

An alternative method of preparing the molten mixture is to use two tanks, melting either the glyceride (or other waxes) or the release-modifying agent in one tank and the other component in another tank. The drug is added to one of these tanks and mixed as described above. The two melts are then pumped through an in-line static mixer or extruder to produce a single molten mixture that is directed to the atomization process described below.

Another method that can be used to prepare the molten mixture is to use a continuously stirred tank system. In this system, the drug, glyceride (or other waxes), and release-modifying agent are continuously added to a heated tank equipped with means for continuous stirring, while the molten feed is continuously removed from the tank. The contents of the tank are heated such that the temperature of the contents is about 10 degrees C. or more above the melting point of the carrier. The drug, glyceride (or other waxes), and release-modifying agent are added in such proportions that the molten mixture removed from the tank has the desired composition. The drug is typically added in solid form and may be pre-heated prior to addition to the tank. The glyceride (or other waxes), and release-modifying agent may also be preheated or even pre-melted prior to addition to the continuously stirred tank system.

In another method for forming the molten mixture is by an extruder. By "extruder" is meant a device or collection of devices that creates a molten extrudate by heat and/or shear forces and/or produces a uniformly mixed extrudate from a solid and/or liquid (e.g., molten) feed. Such devices include, but are not limited to single-screw extruders; twin-screw extruders, including co-rotating, counter-rotating, intermeshing, and non-intermeshing extruders; multiple screw extruders; ram extruders, consisting of a heated cylinder and a piston for extruding the molten feed; gear-pump extruders, consisting of a heated gear pump, generally counter-rotating, that simultaneously heats and pumps the molten feed; and conveyer extruders. Conveyer extruders comprise a conveyer means for transporting solid and/or powdered feeds, such, such as a screw conveyer or pneumatic conveyer, and a pump.

At least a portion of the conveyer means is heated to a sufficiently high temperature to produce the molten mixture. The molten mixture may optionally be directed to an accumulation tank, before being directed to a pump, which directs the molten mixture to an atomizer. Optionally, an in-line mixer may be used before or after the pump to ensure the molten mixture is substantially homogeneous. In each of these extruders the molten mixture is mixed to form a uniformly mixed extrudate. Such mixing may be accomplished by various mechanical and processing means, including mixing elements, kneading elements, and shear mixing by backflow. Thus, in such devices, the composition is fed to the extruder, which produces a molten mixture that can be directed to the atomizer.

In one embodiment, the composition is fed to the extruder in the form of a solid powder. The powdered feed can be prepared using methods well known in the art for obtaining powdered mixtures with high content uniformity. Generally, it is desirable that the particle sizes of the drug, glyceride (or other waxes), and release-modifying agent be similar to obtain a substantially uniform blend. However, this is not essential to the successful practice of the invention.

An example of a process for preparing a substantially uniform blend is as follows. First, the glyceride (or other waxes) and release-modifying agent are milled so that their particle sizes are about the same as that of the drug; next, the drug, glyceride (or other waxes), and release-modifying agent are blended in a V-blender for 20 minutes; the resulting blend is then de-lumped to remove large particles; the resulting blend is finally blended for an additional 4 minutes. In some cases it is difficult to mill the glyceride (or other waxes), and release-modifying agent to the desired particle size since many of these materials tend to be waxy substances and the heat generated during the milling process can gum up the milling equipment. In such cases, small particles of the glyceride (or other waxes), and release-modifying agent can be formed using a melt- or spray-congeal process, as described below. The resulting congealed particles of glyceride (or other waxes), and release-modifying agent can then be blended with the drug to produce the feed for the extruder.

Another method for producing the feed to the extruder is to melt the glyceride (or other waxes) and release-modifying agent in a tank, mix in the drug as described above for the tank system, and then cool the molten mixture, producing a solidified mixture of drug and carrier. This solidified mixture can then be milled to a uniform particle size and fed to the extruder.

A two-feed extruder system can also be used to produce the molten mixture. In this system the drug, glyceride (or other waxes) and release-modifying agent, all in powdered form, are fed to the extruder through the same or different feed ports. In this way, the need for blending the components is eliminated.

Alternatively, the glyceride (or other waxes) and release-modifying agent in powder form may be fed to the extruder at one point, allowing the extruder to melt the glyceride (or other waxes) and release-modifying agent. The drug is then added to the molten glyceride (or other waxes) and release-modifying agent through a second feed delivery port part way along the length of the extruder, thus minimizing the contact time of the drug with the molten glyceride (or other waxes) and release-modifying agent. The closer the second feed delivery port is to the extruder exit, the lower is the residence time of drug in the extruder. Multiple-feed extruders can be used when optional excipients are included in the multiparticulate.

In another method, the composition is in the form of large solid particles or a solid mass, rather than a powder, when fed to the extruder. For example, a solidified mixture can be prepared as described above and then molded to fit into the cylinder of a ram extruder and used directly without milling.

In another method, the glyceride (or other waxes) and release-modifying agent can be first melted in, for example, a tank, and fed to the extruder in molten form. The drug, typically in powdered form, may then be introduced to the extruder through the same or a different delivery port used to feed the glyceride (or other waxes) and release-modifying agent into the extruder. This system has the advantage of separating the melting step for the glyceride (or other waxes) and release-modifying agent from the mixing step, minimizing contact of the drug with the molten glyceride (or other waxes) and release-modifying agent.

In each of the above methods, the extruder should be designed such that it produces a molten mixture with the drug crystals uniformly distributed in the glyceride/release-modifying agent mixture. Generally, the temperature of the extrudate should be about 10 degrees C. or more above the temperature at which the drug and carrier mixture becomes fluid. The various zones in the extruder should be heated to appropriate temperatures to obtain the desired extrudate temperature as well as the desired degree of mixing or shear, using procedures well known in the art. As discussed above for mechanical mixing, a minimum shear should be used to produce a uniform molten mixture, such that the crystalline form of the drug is unchanged and that dissolution or formation of amorphous drug is minimized.

The feed is preferably molten prior to congealing for at least 5 seconds, more preferably at least 10 seconds, and most preferably at least 15 seconds, so as to ensure adequate homogeneity of the drug/glyceride/release-modifying agent melt. It is also preferred that the molten mixture remain molten for no more than about 20 minutes to limit exposure of the drug to the molten mixture. As described above, depending on the reactivity of the chosen glyceride/release-modifying agent mixture, it may be preferable to further reduce the time that the mixture is molten to well below 20 minutes in order to limit drug degradation to an acceptable level. In such cases, such mixtures may be maintained in the molten state for less than 15 minutes, and in some cases, even less than 10 minutes. When an extruder is used to produce the molten feed, the times above refer to the mean time from when material is introduced to the extruder to when the molten mixture is congealed. Such mean times can be determined by procedures well known in the art. In one exemplary method, a small amount of dye or other similar compound is added to the feed while the extruder is operating under nominal conditions. Congealed multiparticulates are then collected over time and analyzed for the dye, from which the mean time is determined.

Once the molten mixture has been formed, it is delivered to an atomizer that breaks the molten feed into small droplets. Virtually any method can be used to deliver the molten mixture to the atomizer, including the use of pumps and various types of pneumatic devices (e.g., pressurized vessels, piston pots). When an extruder is used to form the molten mixture, the extruder itself can be used to deliver the molten mixture to the atomizer. Typically, the molten mixture is maintained at an elevated temperature while delivering the mixture to the atomizer to prevent solidification of the mixture and to keep the molten mixture flowing.

Generally, atomization occurs in one of several ways, including (1) by "pressure" or single-fluid nozzles; (2) by two-fluid nozzles; (3) by centrifugal or spinning-disk atomizers, (4) by ultrasonic nozzles; and (5) by mechanical vibrating nozzles. Detailed descriptions of atomization processes can be found in Lefebvre, Atomization and Sprays (1989) or in Perry's Chemical Engineers' Handbook (7th Ed. 1997). Preferably, a centrifugal or spinning-disk atomizer is used, such as the FX1 100-mm rotary atomizer manufactured by Niro A/S (Soeborg, Denmark).

Once the molten mixture has been atomized, the droplets are congealed, typically by contact with a gas or liquid at a temperature below the solidification temperature of the droplets. Typically, it is desirable that the droplets are congealed in less than about 60 seconds, preferably in less than about 10 seconds, more preferably in less than about 1 second. Often, congealing at ambient temperature results in sufficiently rapid solidification of the droplets. However, the congealing step often occurs in an enclosed space to simplify collection of the multiparticulates. In such cases, the temperature of the congealing media (either gas or liquid) will increase over time as the droplets are introduced into the enclosed space, potentially effecting the formation of the multiparticulates or the chemical stability of the drug. Thus, a cooling gas or liquid is often circulated through the enclosed space to maintain a constant congealing temperature. When it is desirable to minimize the time the drug is exposed to high temperatures, e.g., to prevent degradation, the cooling gas or liquid can be cooled to below ambient temperature to promote rapid congealing, thus minimizing formation of degradants.

Following formation of the multiparticulates, it may be desired to post-treat the multiparticulates to improve drug crystallinity and/or the stability of the multiparticulate.

The multiparticulates may also be mixed or blended with one or more pharmaceutically acceptable materials to form a suitable dosage form. Suitable dosage forms include tablets, capsules, sachets, oral powders for constitution, and the like.

Following formation of the melt spray congeal multiparticulates, the multiparticulates may optionally be coated with an additional exterior coating. The exterior coating may be any conventional coating, such as a protective film coating, a coating to provide delayed or sustained release of the drug, or to provide tastemasking.

In one embodiment, the coating is an enteric coating to provide delayed release of the drug. By "enteric coating" is meant an acid resistant coating that remains intact and does not dissolve at pH of less than about 4. The enteric coating surrounds the multiparticulate so that the solid amorphous dispersion layer does not dissolve or erode in the stomach. The enteric coating may include an enteric coating polymer. Enteric coating polymers are generally polyacids having a $pK_a$ of about 3 to 5. Examples of enteric coating polymers include: cellulose derivatives, such as cellulose acetate phthalate, cellulose acetate trimellitate, hydroxypropyl methyl cellulose acetate succinate, cellulose acetate succinate, carboxy methyl ethyl cellulose, methylcellulose phthalate, and ethylhydroxy cellulose phthalate; vinyl polymers, such as polyvinyl acetate phthalate, vinyl acetate-maleic anhydride copolymer; polyacrylates; and polymethacrylates such as methyl acrylate-methacrylic acid copolymer, methacrylate-methacrylic acid-octyl acrylate copolymer; and styrene-maleic mono-ester copolymer. These may be used either alone or in combination, or together with other polymers than those mentioned above.

One class of enteric coating materials are the pharmaceutically acceptable methacrylic acid copolymer which are copolymers, anionic in character, based on methacrylic acid and methyl methacrylate. Some of these polymers are known and sold as enteric polymers, for example having a solubility in aqueous media at pH 5.5 and above, such as the commercially available EUDRAGIT enteric polymers, such as Eudragit L 30, a polymer synthesized from dimethylaminoethyl methacrylate and Eudragit S and Eudragit FS.

The exterior coatings may include conventional plasticizers, including dibutyl phthalate; dibutyl sebacate; diethyl phthalate; dimethyl phthalate; triethyl citrate; benzyl benzoate; butyl and glycol esters of fatty acids; mineral oil; oleic acid; stearic acid; cetyl alcohol; stearyl alcohol; castor oil; corn oil; coconut oil; and camphor oil; and other excipients such as anti-tack agents, glidants, etc. For plasticizers, triethyl citrate, coconut oil and dibutyl sebacate are particularly preferred.

Exterior coatings can be formed using solvent-based and hot-melt coating processes. In solvent-based processes, the coating is made by first forming a solution or suspension comprising the solvent, the coating material and optional coating additives. The coating materials may be completely dissolved in the coating solvent, or only dispersed in the solvent as an emulsion or suspension or a combination of the two. Latex dispersions are an example of an emulsion or suspension that may be useful as in a solvent-based coating process. In one aspect, the solvent is a liquid at room temperature.

Coating may be conducted by conventional techniques, such as by pan coaters, rotary granulators and fluidized bed coaters such as top-spray, tangential-spray or bottom-spray (Wurster coating). A top-spray method can also be used to apply the coating. In this method, coating solution is sprayed down onto the fluidized cores. The solvent evaporates from the coated cores and the coated cores are re-fluidized in the apparatus. Coating continues until the desired coating thickness is achieved. Compositions and methods for making the multiparticulates of this embodiment are detailed in the following US Patent Applications, US 2005-0181062, US 2005-0181062, US 2008-0199527, US 2005-0186285A1 which are herein incorporated as reference in their entirety.

The multiparticulates of the invention generally are of a mean diameter from about 40 to about 3,000 micron, with a preferred range of 50 to 1,000 micron, and most preferably from about 100 to 300 micron. While the multiparticulates can have any shape and texture, it is preferred that they be spherical, with a smooth surface texture. These physical characteristics of the multiparticulates improve their flow properties, permit them to be uniformly coated (if desired). As used herein, the term "about" means+/−10% of the value.

The multiparticulates of the present invention are particularly suitable for controlled release or delayed release or any combination of these two release profiles when introduced to a use environment. As used herein, a "use environment" can be either the in vivo environment of the gastrointestinal (GI) tract or the in vitro dissolution tests described herein. Information about in vivo release rates can be determined from the pharmacokinetic profile using standard deconvolution or Wagner-Nelson treatment of the data which should be readily known to those skilled in the art.

Once the tofacitinib matrix multiparticulates are formed through methods described above, they may be blended with compressible excipients such as lactose, microcrystalline cellulose, dicalcium phosphate, and the like and the blend compressed to form a tablet or capsule. Disintegrants such as sodium starch glycolate or crosslinked poly(vinyl pyrrolidone) are also usefully employed. Tablets or capsules prepared by this method disintegrate when placed in an aqueous medium (such as the GI tract), thereby exposing the multiparticulate matrix which releases tofacitinib there from.

Other conventional formulation excipients may be employed in the controlled release portion of the invention, including those excipients well known in the art, e.g., as described in Remington: The Science and Practice of Pharmacy, 20th edition (2000). Generally, excipients such as surfactants, pH modifiers, fillers, matrix materials, complexing agents, solubilizers, pigments, lubricants, glidants, flavorants, and so forth may be used for customary purposes and in typical amounts without adversely affecting the properties of the compositions.

Example matrix materials, fillers, or diluents include lactose, mannitol, xylitol, dextrose, sucrose, sorbitol, compressible sugar, microcrystalline cellulose, powdered cellulose, starch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers, polyethylene oxide, hydroxypropyl methyl cellulose and mixtures thereof.

Sustained Release—Osmotic Systems

In another embodiment, tofacitinib is incorporated into osmotic delivery devices or "osmotic pumps" as they are known in the art. Osmotic pumps comprise a core containing an osmotically effective composition surrounded by a semipermeable membrane. The term "semipermeable" in this context means that water can readily diffuse through the membrane, but solutes dissolved in water typically cannot readily diffuse through the membrane relative to the rate of water diffusion through the membrane. In use, when placed in an aqueous environment, the device imbibes water due to the osmotic activity of the core composition. Owing to the semipermeable nature of the surrounding membrane, the contents of the device (including tofacitinib and any excipients) cannot pass through the non-porous regions of the membrane and are driven by osmotic pressure to leave the device through an opening or passageway pre-manufactured into the dosage form or, alternatively, formed in situ in the GI tract as by the bursting of intentionally-incorporated weak points in the coating under the influence of osmotic pressure. The osmotically effective composition includes water-soluble species, which generate a colloidal osmotic pressure, and water-swellable polymers. Examples of such dosage forms are well known in the art. See, for example, Remington: The Science and Practice of Pharmacy, $21^{st}$ Edition, 2006 Chapter 47; page 950-1 and herein incorporated as reference.

In one embodiment of the present invention, tofacitinib is incorporated into a bilayer osmotic delivery device such that the tofacitinib-containing composition must include an entraining agent in the form of a water-swellable polymer and a second push layer or water swelling layer which contains water-swellable polymers and/or osmoticallly active agents, but does not contain any active agent. The bilayer tablet or capsule is surrounded by a semi-permeable membrane which contains one or more openings which are manufactured into the dosage form through such techniques as laser drilling. Such water-swellable polymers are often referred to in the pharmaceutical arts as an "osmopolymer"

or a "hydrogel." The entraining agent suspends or entrains the drug so as to aid in the delivery of the drug through the delivery port(s). While not wishing to be bound by any particular theory, it is believed that upon the imbibition of water into the dosage form, the entraining agent has enough viscosity to allow it to suspend or entrain the drug, while at the same time remaining sufficiently fluid to allow the entraining agent to pass through the delivery port(s) along with the drug. The amount of the entraining agent present in the tofacitinib-containing composition may range from about 20 wt % to about 95 wt %. The entraining agent may be a single material or a mixture of materials. Non-crosslinked polyethylene oxide (PEO) may be used as the entraining agent. Other suitable entraining agents include hydroxypropyl cellulose (HPC), hydroxypropylmethyl cellulose (HPMC), methylcellulose (MC), hydroxyethyl cellulose (HEC) and polyvinyl pyrrolidone (PVP), as well as mixtures of these polymers with PEO.

The choice of the molecular weight for the PEO depends in part on whether the PEO makes up the bulk of the non-tofacitinib portion of the tofacitinib-containing composition, or whether significant amounts of other low-molecular weight water-soluble excipients are included; that is, the PEO molecular weight choice depends on the fraction of the tofacitinib-containing composition that is PEO. Should the tofacitinib-containing composition not become fluid rapidly, the dosage form can swell and rupture the coating that surrounds the core, potentially causing failure of the dosage form. Where the excipients of the tofacitinib-containing composition are primarily PEO (e.g., PEO makes up about 60 wt % or more of the non-tofacitinib components of the tofacitinib-containing composition), it is generally preferred that the PEO have an average molecular weight of from about 100,000 to 300,000 daltons. (As used herein, reference to molecular weights of polymers should be taken to mean average molecular weights.)

Alternatively, another embodiment of the present invention uses a higher molecular weight of PEO from about 500,000 to 800,000 daltons at a lower fraction of the non-tofacitinib excipients, a portion of the PEO being replaced with a fluidizing agent. Ordinarily, when PEO makes up about 60 wt % or more of the non-tofacitinib components of the tofacitinib-containing composition, PEO having a molecular weight of 500,000 daltons or more makes the tofacitinib-containing composition too viscous, and can result in a rupture of the coating or at least in a delay of the release of tofacitinib. However, it has been found that such higher molecular weight PEO is preferred when the non-tofacitinib components of the tofacitinib-containing composition comprise less than about 60 wt % PEO and also contain a fluidizing agent. When using a higher molecular weight PEO, the amount of fluidizing agent present in the tofacitinib-containing composition may range from about 5 to about 50 wt %, preferably 10 to 30 wt % of the tofacitinib-containing composition. Preferred fluidizing agents are low molecular weight, water-soluble solutes such as non-reducing sugars and organic acids with aqueous solubilities of 30 mg/mL or greater. Suitable sugars include xylitol, mannitol, sorbitol, and maltitol. Salts useful as a fluidizing agent include sodium chloride, sodium lactate and sodium acetate. Organic acids useful as a fluidizing agent include adipic acid, citric acid, malic acid, fumaric acid, succinic acid and tartaric acid.

The presence of the fluidizing agent, along with a relatively low level of higher molecular weight PEO (e.g., about 500,000 to about 800,000 daltons) allows the tofacitinib-containing composition to rapidly reach a low viscosity upon imbibition of water. In addition, it has been found that such an embodiment is capable of delivering relatively high amounts of tofacitinib.

The tofacitinib-containing composition may also contain other water-swellable polymers. For example, the tofacitinib-containing composition may contain relatively small amounts of water-swellable polymers that greatly expand in the presence of water. Such water-swellable polymers include sodium starch glycolate, sold under the trade name EXPLOTAB, and croscarmelose sodium, sold under the trade name AC-DI-SOL. Such polymers may be present in amounts ranging from 0 wt % to 10 wt % of the tofacitinib-containing composition.

The tofacitinib-containing composition may optionally include osmotically effective solutes, often referred to as "osmogens" or "osmagents." The amount of osmagent present in the tofacitinib-containing composition may range from about 0 wt % to about 50 wt %, preferably 10 wt % to 30 wt % of the tofacitinib-containing composition. Typical classes of suitable osmagents are water-soluble salts, sugars, organic acids, and other low-molecule-weight organic compounds that are capable of imbibing water to thereby establish an osmotic pressure gradient across the barrier of the surrounding coating. Typical useful salts include magnesium sulfate, magnesium chloride, calcium chloride, sodium chloride, lithium chloride, potassium sulfate, sodium carbonate, sodium sulfite, lithium sulfate, potassium chloride, and sodium sulfate. Conventionally, chloride salts such as sodium chloride are utilized as osmagents.

The tofacitinib-containing composition may further include solubility-enhancing agents or solubilizers that promote the aqueous solubility of the drug, present in an amount ranging from about 0 to about 30 wt % of the tofacitinib-containing composition. Solubilizers useful with tofacitinib include organic acids and organic acid salts, partial glycerides, e.g., less than fully esterified derivatives of glycerin, including glycerides, monoglycerides, diglycerides, glyceride derivatives, polyethylene glycol esters, polypropylene glycol esters, polyhydric alcohol esters, polyoxyethylene ethers, sorbitan esters, polyoxyethylene sorbitan esters, and carbonate salts.

A preferred class of solubilizers is organic acids. Since tofacitinib is a base which is solubilized by protonation, and since its solubility in an aqueous environment of pH 5 or higher is reduced, it is believed that addition of an organic acid to the Tofacitinib-containing composition assists in solubilization and hence absorption of tofacitinib. Even a slight decrease in the pH of the aqueous solution at high pH results in dramatic increases in the solubility of tofacitinib. Organic acids can also promote stability during storage prior to introduction to a use environment due to their tendency to maintain tofacitinib in a protonated state.

There are a variety of factors to consider when choosing an appropriate organic acid for use as a solubilizer with tofacitinib in an osmotic dosage form. The acid should not interact adversely with tofacitinib, should have appropriate water solubility, and should provide good manufacturing properties.

Accordingly, it has been found that a preferred subset of organic acids meeting such criteria consists of citric, succinic, fumaric, adipic, malic and tartaric acids. Citric, malic, and tartaric acid have the advantage of high water solubility and high osmotic pressure. Succinic and fumaric acid offer a combination of both moderate solubility and moderate osmotic pressure.

The water-swellable composition may also optionally contain a colorant. The purpose of the colorant is to allow identification of the drug-containing side of the tablet face for purposes of providing the delivery port, such as by laser drilling through the coating. Acceptable colorants include, but are not limited to, Red Lake No. 40, FD C Blue 2 and FD C Yellow 6.

The tofacitinib-containing layer and/or the water-swellable composition layer and/or the functional rate controlling membrane may optionally contain an antioxidant, such as but not limited to BHT, BHA, sodium metabisulfite, propyl galate, glycerin, vitamin E, Citric Acid or ascorbyl palmitate. The antioxidant may be present in an amount ranging from 0 to 10 wt % of the tofacitinib-containing composition layer and/or the water-swellable composition layer and/or the functional rate controlling membrane. For additional examples of antioxidants, see C.-M. Andersson, A. Hallberg, and T. Hoegberg. Advances in the development of pharmaceutical antioxidants. Advances in Drug Research. 28:65-180, 1996.

Water-swellable composition may also include other conventional pharmaceutically useful excipients such as a binder, including HPC, HPMC, HEC, MC, and PVP, a tableting aid, such as microcrystalline cellulose, and a lubricant such as magnesium stearate.

The water-swellable composition is prepared by mixing the water-swellable polymer and the other excipients to form a uniform blend. To obtain a uniform blend, it is desirable to either wet or dry granulate or dry blend ingredients that have similar particle sizes using the types of processes known to those skilled in the art.

Tableting

The core is prepared by first placing a mixture of the tofacitinib-containing composition into a tablet press and then leveling the mixture by gentle compression. The water-swellable composition is then placed on top of the tofacitinib-containing composition and compressed in order to complete formation of the core. Alternatively, the water-swellable composition can be placed into the tablet press first, followed by the tofacitinib-containing composition.

The respective amounts of tofacitinib-containing composition and water-swellable composition are chosen to provide satisfactory tofacitinib release. When it is desired to provide a large tofacitinib dose in a relatively small dosage size, it is desired to maximize the amount of tofacitinib-containing composition and minimize the amount of water-swellable composition, while still obtaining good release performance. In the dosage forms of the present invention, when the water-swellable polymer in the water-swellable composition is only PEO, the tofacitinib-containing composition may comprise from about 50 to about 85 wt % of the core, and preferably from about 60 to about 70 wt %. These values correspond to a weight ratio of the tofacitinib-containing composition to water-swellable composition of 1 to about 5.7. When all or part of the water-swellable polymer in the water-swellable composition comprises sodium starch glycolate or croscarmellose sodium, the tofacitinib-containing composition may comprise from 50 to 90 wt % of the core, and preferably from about 75 to about 85 wt %. Those values correspond to the weight ratio of the tofacitinib-containing composition to water-swellable composition of from 1 to 9. The absolute value of the diameter and height of the tablets of the present invention can vary over a wide range.

The Coating Following formation of the core, the semipermeable coating is applied.

The coating should have high water permeability and a high strength, while at the same time be easily fabricated and applied. High water permeability is required to permit water to enter the core in sufficient volume. High strength is required to ensure the coating does not burst when the core swells as it imbibes water, leading to an uncontrolled delivery of the core contents. Finally, the coating must have high reproducibility and yield.

It is essential that the coating have at least one delivery port in communication with the interior and exterior of the coating for delivery of the tofacitinib-containing composition. Furthermore, the coating must be non-dissolving and non-eroding during release of the tofacitinib-containing composition, generally meaning that it be water-insoluble, such that tofacitinib is substantially entirely delivered through the delivery port(s), in contrast to delivery via permeation through the coating.

Coatings with these characteristics can be obtained using hydrophilic polymers such as plasticized and unplasticized cellulose esters, ethers, and ester-ethers. Particularly suitable polymers include cellulose acetate (CA), cellulose acetate butyrate (CAB), and ethyl cellulose (EC). One set of polymers are cellulose acetates having acetyl contents of 25 to 42%. One typical polymer is CA having an acetyl content of 39.8%, specifically, CA 398-10 (Eastman Fine Chemicals, Kingsport, Tenn.). CA 398-10 is reported to have an average molecular weight of about 40,000 daltons. Another typical CA having an acetyl content of 39.8% is high molecular weight CA having an average molecular weight greater than about 45,000, and specifically, CA 398-30 (Eastman Fine Chemical) which is reported to have an average molecular weight of 50,000 daltons.

Coating is conducted in conventional fashion by first forming a coating solution and then coating by dipping, fluidized bed coating, or by pan coating. To accomplish this, a coating solution is formed comprising the polymer and a solvent. Typical solvents useful with the cellulosic polymers above include acetone, methyl acetate, ethyl acetate, isopropyl acetate, n-butyl acetate, methyl isobutyl ketone, methyl propyl ketone, ethylene glycol monoethyl ether, ethylene glycol monoethyl acetate, methylene dichloride, ethylene dichloride, propylene dichloride, nitroethane, nitropropane, tetrachloroethane, 1,4-dioxane, tetrahydrofuran, diglyme, and mixtures thereof. The coating solution typically contains 2 to 15 wt % of the polymer.

The coating solution may also include pore-formers or non-solvents in any amount as long as the polymer remains soluble at the conditions used to form the coating and as long as the coating remains water permeable and has sufficient strength. Pore-formers and their use in fabricating coatings are described in U.S. Pat. Nos. 5,698,220 and 5,612,059, the pertinent disclosures of which are incorporated herein by reference. The term "pore former," as used herein, refers to a material added to the coating solution that has low or no volatility relative to the solvent such that it remains as part of the coating following the coating process but that is sufficiently water swellable or water soluble such that, in the aqueous use environment it provides a water-filled or water-swollen channel or "pore" to allow the passage of water, thereby enhancing the water permeability of the coating. Suitable pore formers include but are not limited to hydroxypropylcellulose (HPC), polyethylene glycol ("PEG"), PVP, and PEO. To obtain a combination of high water permeability and high strength when PEG or HPC are used as a pore former, the weight ratio of CA:PEG or CA:HPC should range from about 6:4 to about 9:1.

The addition of a non-solvent such as water to the coating solution results in exceptional performance. By "non-solvent" is meant any material added to the coating solution that substantially dissolves in the coating solution and reduces the solubility of the coating polymer or polymers in the solvent. In general, the function of the non-solvent is to impart porosity to the resulting coating. As described below, porous coatings have higher water permeability than an equivalent weight of a coating of the same composition that is not porous and this porosity is indicated by a reduction in the density of the coating (mass/volume). Although not wishing to be bound by any particular mechanism of pore formation, it is generally believed that addition of a non-solvent imparts porosity to the coating during evaporation of solvent by causing the coating solution to undergo liquid and liquid phase separation prior to solidification. The suitability and amount of a particular candidate material can be evaluated for use as a non-solvent by progressively adding the candidate non-solvent to the coating solution until it becomes cloudy. If this does not occur at any addition level up to about 50 wt % of the coating solution, it generally is not appropriate for use as a non-solvent. When clouding is observed, termed the "cloud point," an appropriate level of non-solvent for maximum porosity is the amount just below the cloud point. For acetone solutions comprising 7 wt % CA and 3 wt % PEG, the cloud point is at about 23 wt % water. When lower porosities are desired, the amount of non-solvent can be reduced as low as desired.

Suitable non-solvents are any materials that have appreciable solubility in the solvent and that lower the coating polymer solubility in the solvent. The preferred non-solvent depends on the solvent and the coating polymer chosen. In the case of using a volatile polar coating solvent such as acetone, suitable non-solvents include water, glycerol, alcohols such as methanol or ethanol.

When using CA 398-10, coating solution weight ratios of CA:PEG 3350:water are 2.4:1.6:5, 2.8:1.2:5, 3.2:0.8:5, and 3.6:0.4:5, with the remainder of the solution comprising a solvent such as acetone. Thus, for example, in a solution having a weight ratio of CA:PEG 3350:water of 2.8:1.2:5, CA comprises 2.8 wt % of the solution, PEG 3350 comprises 1.2 wt % of the solution, water comprises 5 wt % of the solution, and acetone comprises the remaining 91 wt %. Likewise, coating solution weight ratios of CA:HPC:water are 1.2:0.8:9.8, 2.4:1.6:19.6, 1.6:0.4:4.9, and 3.2:0.8:9.8, with the remainder of the solution comprising a solvent such as acetone. Thus, for example, in a solution having a weight ratio of CA:HPC:water of 1.2:0.8:10, CA comprises 1.2 wt % of the solution, HPC comprises 0.8 wt % of the solution, water comprises 10 wt % of the solution, and acetone comprises the remaining 88 wt %. Further, coating solution weight ratios of CA:HPC:methanol are 1.8:1.2:19.6, 2.4:1.6:19.6, 1.6:0.4:4.9, and 3.2:0.8:9.8, with the remainder of the solution comprising a solvent such as acetone. Thus, for example, in a solution having a weight ratio of CA:HPC:methanol of 1.8:1.2:19.6, CA comprises 1.8 wt % of the solution, HPC comprises 1.2 wt % of the solution, methanol comprises 19.6 wt % of the solution, and acetone comprises the remaining 77.4 wt %.

When incorporating antioxidants into the coating solution, a third solvent may be required to ensure good dispersion of the antioxidant into the coating. For example, a CA:PEG:water composition of 2.4:1.6:5 that includes 0.05 wt % of antioxidant of the solution requires 5 wt % methanol and 86% acetone.

Coatings formed from these coating solutions are generally porous. By "porous" is meant that the coating in the dry state has a density less than the density of the same material in a nonporous form. By "nonporous form" is meant a coating material formed by using a coating solution containing no non-solvent, or the minimal amount of non-solvent required to produce a homogeneous coating solution. The dry-state density of the coating can be calculated by dividing the coating weight (determined from the weight gain of the tablets before and after coating) by the coating volume (calculated by multiplying the coating thickness, as determined by optical or scanning electron microscopy, by the tablet surface area). The porosity of the coating is one of the factors that leads to the combination of high water permeability and high strength of the coating.

The weight of the coating around the core depends on the composition and porosity of the coating, but generally should be present in an amount ranging from 3 to 30 wt %, based on the weight of the uncoated core. A coating weight of at least about 8 wt %, is typically preferred for sufficient strength for reliable performance, although lower coating weights can be used to achieve desire high water imbibing rates and, subsequently, higher release rates of tofacitinib from the dosage form.

While porous coatings based on CA, PEG or HPC, and water described above translate to excellent results, other pharmaceutically acceptable materials could be used in the coating so long as the coating has the requisite combination of high water permeability, high strength, and ease of fabrication and application. Further, such coatings may be dense, porous, or "asymmetric," having one or more dense layers and one or more porous layers such as those disclosed in U.S. Pat. Nos. 5,612,059 and 5,698,220, the pertinent disclosures of which are incorporated herein by reference.

The coating must also contain at least one delivery port in communication with the interior and exterior of the coating to allow for release of the drug-containing composition to the exterior of the dosage form. The delivery port can range in size from about the size of the drug particles, and thus could be as small as 1 to 100 microns in diameter and may be termed pores, up to about 5000 microns in diameter. The shape of the port may be substantially circular, in the form of a slit, or other convenient shape to ease manufacturing and processing. The port(s) may be formed by post-coating mechanical or thermal means or with a beam of light (e.g., a laser), a beam of particles, or other high-energy source, or may be formed in situ by rupture of a small portion of the coating. Such rupture may be controlled by intentionally incorporating a relatively small weak portion into the coating. Delivery ports may also be formed in situ by erosion of a plug of water-soluble material or by rupture of a thinner portion of the coating over an indentation in the core. Delivery ports may be formed by coating the core such that one or more small regions remain uncoated. In addition, the delivery port can be a large number of holes or pores that may be formed during coating, as in the case of asymmetric membrane coatings, described in more detail herein, and of the type disclosed in U.S. Pat. Nos. 5,612,059 and 5,698,220, the disclosures of which are incorporated by reference. When the delivery pathways are pores there can be a multitude of such pores that range in size from 1 micron to greater than 100 microns. During operation, one or more of such pores may enlarge under the influence of the hydrostatic pressure generated during operation. At least one delivery port should be formed on the side of coating that is adjacent to the tofacitinib-containing composition, so that the tofacitinib-containing composition will be extruded out of the delivery port by the swelling action of the water-swellable composition. It is recognized that some processes for forming delivery ports may also form holes or pores in the coating adjacent to the water-swellable composition.

The coating may optionally include a port in communication with the water-swellable composition. Such a delivery port does not typically alter the tofacitinib release characteristics of the dosage form, but may provide manufacturing advantages. It is believed that the water-swellable compositions, such as those containing PEO with a molecular weight between 3,000,000 and 8,000,000 daltons, are too viscous to appreciably exit the port. In dosage forms wherein the delivery ports are drilled either mechanically or by laser, the tablet must be oriented so that at least one delivery port is formed in the coating adjacent to the tofacitinib-containing composition. A colorant within the water-swellable composition is used to orient the core dosage form during the drilling step in manufacture. By providing a delivery port on both faces of the dosage form, the need to orient the dosage form may be eliminated and the colorant may be removed from the water-swellable composition.

In yet another embodiment, tofacitinib is incorporated into a variation of the above disclosed osmotic delivery device, an asymmetric membrane technology (AMT). These devices have been disclosed in Herbig, et al., J. Controlled Release, 35, 1995, 127-136, and U.S. Pat. Nos. 5,612,059 and 5,698,220 as coatings in osmotic drug delivery systems. These AMT systems provide the general advantages of osmotic controlled release devices (reliable drug delivery independent of position in gastrointestinal tract), yet do not require the added manufacturing step of drilling a hole in the coating, as seen with a number of other osmotic systems. In the formation of these porous coatings, a water-insoluble polymer is combined with a water-soluble, pore-forming material. The mixture is coated onto an osmotic tablet core from a combination of water and solvent. As the coating dries, a phase inversion process occurs whereby a porous, asymmetric membrane is produced. The use of an AMT system for controlled release of a drug with similar physiochemical properties is described in US Patent Application Publication US2007/0248671 and herein incorporated as reference.

While a number of materials have been disclosed for use as pore-formers in the production of asymmetric membranes, the previously disclosed materials all bring chemical or physical stability issues into the system. In particular, many of the prior art materials are liquids, which can potentially migrate out of the coating during storage. Of the ones that are solid, both polymeric materials and inorganic materials have been taught. Inorganic materials can be difficult to use for a number of reasons. In particular, they often have a tendency to crystallize and/or adsorb moisture on storage. The particular polymeric materials that have been taught include polyvinylpyrrolidone (PVP) and polyethylene glycol (PEG) derivatives. Both of these materials have a strong tendency to form peroxides and/or formaldehyde upon storage (see for example Waterman, et al., "Impurities in Drug Products" in Handbook of Isolation and Characterization of Impurities in Pharmaceuticals, S. Ajira and K. M. Alsante, Eds. 2003, pp. 75-85). Many drug substances are reactive with such polymer degradation products, both because of their intrinsic reactivity and their tendency to migrate upon storage. However, this formulation space is relatively narrow. U.S. Pat. No. 4,519,801 discloses a wide list of water-soluble polymeric components useful for coatings in osmotic systems, but fails to teach appropriate selections of water-soluble components for AMT systems. There remains, therefore, a need for new pore-forming materials for AMT systems wherein the pore-forming materials do not generate reactive byproducts, crystallize or migrate from the coating upon storage.

One aspect of the present invention provides a dosage form which comprises (a) a core containing at least one pharmaceutically active ingredient and (b) at least one asymmetric membrane technology coating wherein said coating comprises:

a. one or more substantially water-insoluble polymers, and b. one or more solid, water-soluble polymeric materials that do not contain amounts of hydrogen peroxide or formaldehyde greater than about 0.01 percent w:w after storage at 40 degrees C./75 percent RH for 12 weeks.

One aspect of the present invention also provides a dosage form wherein the dosage form delivers drug primarily by osmotic pressure. In particular embodiments, the present invention provides a dosage form wherein the pharmaceutically active ingredient is tofacitinib or a pharmaceutically acceptable salt thereof. The water-insoluble polymer as used in the present invention preferably comprises a cellulose derivative, more preferably, cellulose acetate. The solid, water-soluble polymeric material as used in the present invention comprises a polymer having a weight average molecular weight between 2000 and 50,000 daltons. In preferable embodiments, the solid, water-soluble polymeric material is selected from the group consisting of water-soluble cellulose derivatives, acacia, dextrin, guar gum, maltodextrin, sodium alginate, starch, polyacrylates, polyvinyl alcohols and zein. In particular embodiments, the water-soluble cellulose derivatives comprise hydroxypropylcellulose, hydroxypropylmethylcellulose and hydroxyethylcellulose. In certain embodiments, the solid, water-soluble, polymeric material has a viscosity for a 5 percent w:w aqueous solution of less than 400 mPa s. In certain other embodiments, the solid, water-soluble, polymeric material has a viscosity for a 5 percent w:w aqueous solution of less than 300 mPa s. In other embodiments, the solid, water-soluble, polymeric material has a softening temperature greater than 55 degrees C.

The dosage form of the present invention may be a tablet or a multiparticulate. In certain embodiments, the core of the present invention contains a sugar. More preferably, the sugar is sorbitol. In certain embodiments, the water-insoluble polymer is cellulose acetate and said solid, water-soluble polymeric material is hydroxypropylcellulose. In certain preferred embodiments, the dosage form of the invention contains tofacitinib, or a pharmaceutically acceptable salt thereof, as the pharmaceutically active ingredient, while the water-insoluble polymer is cellulose acetate and the solid, water-soluble polymeric material is hydroxypropylcellulose.

A process of the present invention encompasses the process wherein the coating is applied from a mixture of acetone and water using a pan coating. The process of the present invention also encompasses the process wherein the asymmetric membrane comprises cellulose acetate and hydroxypropylcellulose which is coated from a mixture of acetone to water between about 9:1 and 6:4, w:w, and more preferably between about 7:3 and about 6:4, w:w, using a pan coater. In particular, the process of the present invention encompasses the process wherein the core comprises tofacitinib, or a pharmaceutically acceptable salt thereof.

In the preparation of the asymmetric membrane coatings of the present invention, the water-insoluble component of the asymmetric membrane coating preferentially is formed from cellulose derivatives. In particular, these derivatives include cellulose esters and ethers, namely the mono-, di- and triacyl esters wherein the acyl group consists of two to four carbon atoms and lower alkyl ethers of cellulose wherein the alkyl group has one to four carbon atoms. The cellulose esters can also be mixed esters, such as cellulose acetate butyrate, or a blend of cellulose esters. The same variations can be found in ethers of cellulose and include blends of cellulose esters and cellulose ethers. Other cellulose derivatives which can be used in making asymmetric membranes of the present invention include cellulose nitrate, acetaldehyde dimethyl cellulose, cellulose acetate ethyl carbamate, cellulose acetate phthalate, cellulose acetate methyl carbamate, cellulose acetate succinate, cellulose acetate dimethaminoacetate, cellulose acetate ethyl carbonate, cellulose acetate dimethaminoacetate, cellulose acetate ethyl carbonate, cellulose acetate chloroacetate, cellulose acetate ethyl oxalate, cellulose acetate methyl sulfonate, cellulose acetate butyl sulfonate, cellulose acetate p-toluene sulfonate, cellulose cyanoacetates, cellulose acetate trimellitate, cellulose methacrylates and hydroxypropylmethylcellulose acetate succinate. A particularly preferred water-insoluble component is cellulose acetate. Particularly preferred cellulose acetates include those having an acetyl content of about 40 percent and a hydroxyl content of about 3.5 percent. Other materials also can be used in the fabrication of asymmetric membrane technology coatings, provided such materials are substantially water-insoluble, film-forming and safe to use in pharmaceutical applications.

In the preparation of the asymmetric membrane coatings of the present invention, the water-soluble polymeric component of the present invention comprises solid, polymeric materials that do not form hydrogen peroxide or formaldehyde upon storage for 12 weeks at 40 degrees C./75 percent relative humidity, in an amount greater than about 0.01 percent w/w (100 parts per million, ppm). In terms of water solubility, the solid polymeric water-soluble material preferentially has a water-solubility of greater than 0.5 mg/mL; more preferably, greater than 2 mg/mL; and still more preferably, greater than 5 mg/mL.

The solid polymeric water-soluble material has a melting or softening temperature above room temperature. Preferentially, the solid material has a melting or softening temperature above 30 degrees C.; more preferentially, above 40 degrees C.; and most preferentially, above 50 degrees C. Melting and softening points can be determined visually using a melting point apparatus, or alternatively, can be measured using differential scanning calorimetry (DSC), as is known in the art. The polymer can be either a homopolymer or a copolymer. Such polymers can be natural polymers, or be derivatives of natural products, or be entirely synthetic. The molecular weight of such materials is preferentially high enough to prevent migration and aid in film-forming, yet low enough to allow coating (as discussed below). The preferred molecular weight range for the present invention is therefore between 2000 and 50,000 daltons (weight average). Preferred polymers suitable as water-soluble components of an asymmetric membrane technology coating for the present invention include substituted, water-soluble cellulose derivatives, acacia, dextrin, guar gum, maltodextrin, sodium alginate, starch, polyacrylates, polyvinyl alcohols and zein. Particularly preferred water-soluble polymers include hydroxyethylcellulose, hydroxypropylcellulose and polyvinylalcohol.

It is difficult to obtain asymmetric membrane coatings if the viscosity of the coating solution is too high, and that one approach to solving this issue is to use more dilute solutions of the polymer. Due to the phase behavior of the coating solution, having both water-soluble and organic-soluble components, there is a limit to how low the concentration of the water-soluble polymer can be and still provide a commercializable process. For this reason, it is preferred that the water-soluble polymers not have too high a viscosity. Viscosities can be determined at 25 degrees C. using a Brookfield LVF viscometer (available from Brookfield Engineering Corp., Middleboro, Mass.) with spindle and speed combinations depending on viscosity levels for 5 percent (w:w) aqueous solutions. Preferred water-soluble polymers have viscosities for 5 percent (w:w) solutions of less than 400 mPa s, more preferably, less than 300 mPa s.

Using the above criteria, especially preferred water-soluble polymers include hydroxypropylcellulose and hydroxyethylcellulose having a viscosity for a 5 percent (w:w) of less than 300 mPa s. Commercially available examples of such polymers include Klucel EF™ and Natrasol LR™, both made by the Aqualon Division of Hercules Corp., Hopewell, Va.

The water-soluble, solid polymeric material's stability to formation of hydrogen peroxide can be measured by storing the polymer in an oven having a temperature and relative humidity (RH) of 40 degrees C. and 75 percent RH, respectively. The polymer should be stored exposed to the oven environment under "open" conditions. The polymer should be stored for at least 12 weeks. Levels of hydrogen peroxide can be administered as described in G. M. Eisenberg, "Colorimetric determination of hydrogen peroxide" in Ind. Eng. Chem. (Anal. Ed.), 1943, 15, 327-328. Under these storage conditions, acceptable polymeric materials for the present invention have hydrogen peroxide levels below 100 parts per million (ppm); more preferably, below 50 ppm; and most preferably, below 10 ppm.

Similarly, the water-soluble polymers stability to formation of formaldehyde can be measured by storing the polymer in an oven at 40 degrees C. and 75 percent RH. Polymer should be stored in a sealed container to avoid loss of volatile formaldehyde. The polymer should be stored for at least 12 weeks. Levels of formaldehyde can be determined as described in M. Ashraf-Khorassani, et al., "Purification of pharmaceutical excipients with supercritical fluid extraction" in Pharm. Dev. Tech. 2005, 10, 1-10. Under these storage conditions, acceptable water-soluble polymeric materials for the present invention have formaldehyde levels below 100 ppm, more preferably, below 50 ppm, and most preferably, below 10 ppm.

It will be appreciated by those skilled in the art that the asymmetric membrane technology coating formulation can contain small amounts of other materials without significantly changing its function or altering the nature of the present invention. Such additives include glidants (e.g., talc and silica) and plasticizers (e.g., triethylcitrate and triacetin), which are typically added, when needed, at levels of less than about 5 percent (w:w) of the coating.

It will be appreciated by those skilled in the art that active pharmaceutical ingredients can also be in the form of pharmaceutically acceptable salts. The cores for the present invention can also employ solubilizing additives. Such additives include pH-buffering additives to maintain the core at a pH wherein the active pharmaceutical ingredient has a sufficiently high solubility to be pumped out of the dosage form in solution. The active pharmaceutical ingredient can be present in the core at levels ranging from about 0.1 percent (w:w) to about 75 percent (w:w).

The core can contain osmotic agents which help to provide the driving force for drug delivery. Such osmotic agents include water-soluble sugars and salts. A particularly preferred osmotic agent is mannitol or sodium chloride.

The core of the AMT system can contain other additives to provide for such benefits as stability, manufacturability and system performance. Stabilizing excipients include pH-modifying ingredients, antioxidants, chelating agents, and other such additives as is known in the art. Excipients that improve manufacturability include agents to help in flow, compression or extrusion. Flow can be helped by such additives as talc, stearates and silica. Flow is also improved by granulation of the drug and excipients, as is known in the art. Such granulations often benefit from the addition of binders such as hydroxypropylcellulose, starch and polyvinylpyrrollidone (povidone). Compression can be improved by the addition of diluents to the formulation. Examples of diluents include lactose, mannitol, microcrystalline cellulose and the like, as is known in the art. For cores produced by extrusion, the melt properties of the excipients can be important. Generally, it is preferable that such excipients have melting temperatures below about 100 degrees C. Examples of appropriate excipients for melt processes include esterified glycerines and stearyl alcohol. For compressed dosage forms, manufacturability can be improved by addition of lubricants. A particularly preferred lubricant is magnesium stearate.

Cores can be produced using standard tablet compression processes, as is known in the art. Such processes involve powders filling dies followed by compression using appropriate punches. Cores can also be produced by an extrusion process. Extrusion processes are especially well-suited to making small cores (multiparticulates). A preferred extrusion process is a melt-spray-congeal process as described in WO2005/053653A1, incorporated by reference. Cores can also be prepared by layering drug onto seed cores. Such seed cores are preferentially made of sugar or microcrystalline cellulose. Drug can be applied onto the cores by spraying, preferentially in a fluid-bed operation, as is known in the art.

In the practice of the subject invention, the cores are coated with the asymmetric membrane by any technique that can provide the asymmetric membrane as a coating over the entire cores. Preferred coating methods include pan coating and fluid-bed coating. In both coating processes, the water-insoluble polymer and water-soluble polymer as well as any other additives are first dissolved or dispersed in an appropriate solvent or solvent combination. In order to achieve a suitably porous membrane, the coating solvent needs to be optimized for performance. Generally, the solvents are chosen such that the more volatile solvent is the better solvent for the water-insoluble polymeric component. The result is that during coating, the water-insoluble polymeric component precipitates from solution. Preferred solvents and solvent ratios can be determined by examining the multi-component solubility behavior of the system. A preferred solvent mixture is acetone and water, with a ratio of between about 9:1 and about 6:4, w:w.

In a preferred embodiment of the present invention, tofacitinib is incorporated into a monolithic osmotic delivery device, known as an extrudable core system, such that the tofacitinib-containing composition must include viscosifying polymers and osmoticallly active agents, and may optionally include solubility enhancing agents and/or antioxidants. The monolithic tablet or capsule is surrounded by a semi-permeable membrane which contains one or more openings which are manufactured into the dosage form through such techniques as laser drilling. The viscosifying polymers suspend or entrain the drug so as to aid in the delivery of the drug through the delivery port(s). While not wishing to be bound by any particular theory, it is believed that upon the imbibition of water into the dosage form, the viscosifying polymer has enough viscosity to allow it to suspend or entrain the drug, while at the same time remaining sufficiently fluid to allow the viscosifying polymer to pass through the delivery port(s) along with the drug. The amount of the viscosifying polymer present in the tofacitinib-containing composition may range from about 2 wt % to about 20 wt %, preferably from about 3 to about 15%, and more preferably from about 4 wt % to about 10 wt %. The viscosifying polymer may be a single material or a mixture of materials. Non-crosslinked polyethylene oxide (PEO) and Hydroxyethyl cellulose (HEC) may be used as the viscosifying polymers. HEC is preferred as the viscosifying polymer. The molecular weight of HEC can be from about 300,000 to about 2,000,000, more preferably between about 700,000 to about 1,500,000).

The tofacitinib-containing composition also includes osmotically effective solutes, often referred to as "osmogens" or "osmagents." The amount of osmagent present in the tofacitinib-containing composition may range from about 15 wt % to about 95 wt %, preferably from about 40 wt % to about 90 wt %, more preferably about 60% to about 85%, and most preferably about 70% to about 85%, of the tofacitinib-containing composition. Typical classes of suitable osmagents are water-soluble salts, sugars, organic acids, and other low-molecule-weight organic compounds that are capable of imbibing water to thereby establish an osmotic pressure gradient across the barrier of the surrounding coating. Typical useful salts include magnesium sulfate, magnesium chloride, calcium chloride, sodium chloride, lithium chloride, potassium sulfate, sodium carbonate, sodium sulfite, lithium sulfate, potassium chloride, and sodium sulfate. Preferred salts include as sodium chloride and potassium chloride. Preferred organic acids include ascorbic acid, 2-benzene carboxylic acid, benzoic acid, fumaric acid, citric acid, maleic acid, serbacic acid, sorbic acid, edipic acid, editic acid, glutamic acid, toluene sulfonic acid, and tartaric acid. Preferred sugars include mannitol, sucrose, sorbitol, xylitol, lactose, dextrose, and trehlaose. A more preferred sugar is sorbitol. The osmagents can be used alone or as a combination of two or more osmagents.

The tofacitinib-containing composition may further include solubility-enhancing agents or solubilizers that promote the aqueous solubility of the drug, present in an amount ranging from about 0 to about 30 wt % of the tofacitinib-containing composition. Solubilizers useful with tofacitinib include organic acids and organic acid salts, partial glycerides, e.g., less than fully esterified derivatives of glycerin, including glycerides, monoglycerides, diglycerides, glyceride derivatives, polyethylene glycol esters, polypropylene glycol esters, polyhydric alcohol esters, polyoxyethylene ethers, sorbitan esters, polyoxyethylene sorbitan esters, and carbonate salts.

A preferred class of solubilizers is organic acids. Since tofacitinib is a base which is solubilized by protonation, and since its solubility in an aqueous environment of pH 5 or higher is reduced, it is believed that addition of an organic acid to the Tofacitinib-containing composition assists in solubilization and hence absorption of tofacitinib. Even a slight decrease in the pH of the aqueous solution at high pH results in dramatic increases in the solubility of tofacitinib. Organic acids can also promote stability during storage prior to introduction to a use environment due to their tendency to maintain tofacitinib in a protonated state.

There are a variety of factors to consider when choosing an appropriate organic acid for use as a solubilizer with tofacitinib in an osmotic dosage form. The acid should not interact adversely with tofacitinib, should have appropriate water solubility, and should provide good manufacturing properties.

Accordingly, it has been found that a preferred subset of organic acids meeting such criteria consists of citric, succinic, fumaric, adipic, malic and tartaric acids. Citric, malic, and tartaric acid have the advantage of high water solubility and high osmotic pressure. Succinic and fumaric acid offer a combination of both moderate solubility and moderate osmotic pressure.

The tofacitinib-containing composition layer and/or the functional rate controlling membrane may optionally contain an antioxidant, such as but not limited to BHT, BHA, sodium metabisulfite, propyl galate, glycerin, vitamin E, Citric Acid or ascorbyl palmitate. The antioxidant may be present in an amount ranging from 0 to 10 wt % of the tofacitinib-containing composition layer and/or the water-swellable composition layer and/or the functional rate controlling membrane. For additional examples of antioxidants, see C.-M. Andersson, A. Hallberg, and T. Hoegberg. Advances in the development of pharmaceutical antioxidants. Advances in Drug Research. 28:65-180, 1996.

The Tofacitinib-containing composition is prepared by mixing the viscosifying polymer and the other excipients to form a uniform blend. To obtain a uniform blend, it is desirable to either wet or dry granulate or dry blend the components using the types of processes known to those skilled in the art.

Tableting

The core is prepared by first placing a mixture of the tofacitinib-containing composition into a tablet press and compressed in order to complete formation of the core. Tablet shapes may include any tablet shape known to those skilled in the art. Preferable tablet shapes include SRC (standard round concave), oval, modified oval, capsule, caplet, and almond. More preferable tablet shapes include oval, modified oval, caplet, and capsule.

The Coating

Following formation of the core, the semi-permeable coating is applied. The coating should have high water permeability and a high strength, while at the same time be easily fabricated and applied. High water permeability is required to permit water to enter the core in sufficient volume. High strength is required to ensure the coating does not burst when the core swells as it imbibes water, leading to an uncontrolled delivery of the core contents. Finally, the coating must have high reproducibility and yield.

It is essential that the coating have at least one delivery port in communication with the interior and exterior of the coating for delivery of the tofacitinib-containing composition. Furthermore, the coating must be non-dissolving and non-eroding during release of the tofacitinib-containing composition, generally meaning that it be water-insoluble, such that tofacitinib is substantially entirely delivered through the delivery port(s), in contrast to delivery via permeation through the coating.

Coatings with these characteristics can be obtained using hydrophilic polymers such as plasticized and unplasticized cellulose esters, ethers, and ester-ethers. Particularly suitable polymers include cellulose acetate (CA), cellulose acetate butyrate (CAB), and ethyl cellulose (EC). One set of polymers are cellulose acetates having acetyl contents of 25 to 42%. One typical polymer is CA having an acetyl content of 39.8%, specifically, CA 398-10 (Eastman Fine Chemicals, Kingsport, Tenn.). CA 398-10 is reported to have an average molecular weight of about 40,000 daltons. Another typical CA having an acetyl content of 39.8% is high molecular weight CA having an average molecular weight greater than about 45,000, and specifically, CA 398-30 (Eastman Fine Chemical) which is reported to have an average molecular weight of 50,000 daltons.

Coating is conducted in conventional fashion by first forming a coating solution and then coating by dipping, fluidized bed coating, or by pan coating. To accomplish this, a coating solution is formed comprising the polymer and a solvent. Typical solvents useful with the cellulosic polymers above include acetone, methyl acetate, ethyl acetate, isopropyl acetate, n-butyl acetate, methyl isobutyl ketone, methyl propyl ketone, ethylene glycol monoethyl ether, ethylene glycol monoethyl acetate, methylene dichloride, ethylene dichloride, propylene dichloride, nitroethane, nitropropane, tetrachloroethane, 1,4-dioxane, tetrahydrofuran, diglyme, and mixtures thereof. The coating solution typically contains 2 to 15 wt % of the polymer.

The coating solution may also include pore-formers or non-solvents in any amount as long as the polymer remains soluble at the conditions used to form the coating and as long as the coating remains water permeable and has sufficient strength. Pore-formers and their use in fabricating coatings are described in U.S. Pat. Nos. 5,698,220 and 5,612,059, the pertinent disclosures of which are incorporated herein by reference. The term "pore former," as used herein, refers to a material added to the coating solution that has low or no volatility relative to the solvent such that it remains as part of the coating following the coating process but that is sufficiently water swellable or water soluble such that, in the aqueous use environment it provides a water-filled or water-swollen channel or "pore" to allow the passage of water, thereby enhancing the water permeability of the coating. Suitable pore formers include but are not limited to hydroxypropylcellulose (HPC), polyethylene glycol ("PEG"), PVP, and PEO. To obtain a combination of high water permeability and high strength when PEG or HPC are used as a pore former, the weight ratio of CA:PEG or CA:HPC should range from about 6:4 to about 9:1. CA:HPC is a preferred coating composition. Preferred CA:HPC weight ratios should range from 6:4 to 7:3. Preferred CA:PEG weight ratios should range from 6:4 to 7:3.

The addition of a non-solvent such as water or methanol to the coating solution results in exceptional performance. By "non-solvent" is meant any material added to the coating solution that substantially dissolves in the coating solution and reduces the solubility of the coating polymer or polymers in the solvent. In general, the function of the non-solvent is to impart porosity to the resulting coating. As described below, porous coatings have higher water permeability than an equivalent weight of a coating of the same composition that is not porous and this porosity is indicated by a reduction in the density of the coating (mass/volume). Although not wishing to be bound by any particular mechanism of pore formation, it is generally believed that addition of a non-solvent imparts porosity to the coating during evaporation of solvent by causing the coating solution to undergo liquid and liquid phase separation prior to solidification. The suitability and amount of a particular candidate material can be evaluated for use as a non-solvent by progressively adding the candidate non-solvent to the coating solution until it becomes cloudy. If this does not occur at any addition level up to about 50 wt % of the coating solution, it generally is not appropriate for use as a non-solvent. When clouding is observed, termed the "cloud point," an appropriate level of non-solvent for maximum porosity is the amount just below the cloud point. For acetone solutions comprising 7 wt % CA and 3 wt % PEG, the cloud point is at about 23 wt % water. When lower porosities are desired, the amount of non-solvent can be reduced as low as desired.

Suitable non-solvents are any materials that have appreciable solubility in the solvent and that lower the coating polymer solubility in the solvent. The preferred non-solvent depends on the solvent and the coating polymer chosen. In the case of using a volatile polar coating solvent such as acetone, suitable non-solvents include water, glycerol, alcohols such as methanol or ethanol.

When using CA 398-10, coating solution weight ratios of CA:PEG 3350: water are 2.4:1.6:5, 2.8:1.2:5, 3.2:0.8:5, and 3.6:0.4:5, with the remainder of the solution comprising a solvent such as acetone. Thus, for example, in a solution having a weight ratio of CA:PEG 3350: water of 2.8:1.2:5, CA comprises 2.8 wt % of the solution, PEG 3350 comprises 1.2 wt % of the solution, water comprises 5 wt % of the solution, and acetone comprises the remaining 91 wt %. Likewise, coating solution weight ratios of CA:HPC:water are 1.2:0.8:9.8, 2.4:1.6:19.6, 1.6:0.4:4.9, and 3.2:0.8:9.8, with the remainder of the solution comprising a solvent such as acetone. Thus, for example, in a solution having a weight ratio of CA:HPC:water of 1.2:0.8:10, CA comprises 1.2 wt % of the solution, HPC comprises 0.8 wt % of the solution, water comprises 10 wt % of the solution, and acetone comprises the remaining 88 wt %. Further, coating solution weight ratios of CA:HPC:methanol are 1.8:1.2:19.6, 2.4:1.6:19.6, 1.6:0.4:4.9, and 3.2:0.8:9.8, with the remainder of the solution comprising a solvent such as acetone. Thus, for example, in a solution having a weight ratio of CA:HPC:methanol of 1.8:1.2:19.6, CA comprises 1.8 wt % of the solution, HPC comprises 1.2 wt % of the solution, methanol comprises 19.6 wt % of the solution, and acetone comprises the remaining 77.4 wt %.

When incorporating antioxidants into the coating solution, a third solvent may be required to ensure good dispersion of the antioxidant into the coating. For example, a CA:PEG:water composition of 2.4:1.6:5 that includes 0.05 wt % of antioxidant of the solution requires 5 wt % methanol and 86% acetone.

Coatings formed from these coating solutions are generally porous. By "porous" is meant that the coating in the dry state has a density less than the density of the same material in a nonporous form. By "nonporous form" is meant a coating material formed by using a coating solution containing no non-solvent, or the minimal amount of non-solvent required to produce a homogeneous coating solution. The dry-state density of the coating can be calculated by dividing the coating weight (determined from the weight gain of the tablets before and after coating) by the coating volume (calculated by multiplying the coating thickness, as determined by optical or scanning electron microscopy, by the tablet surface area). The porosity of the coating is one of the factors that leads to the combination of high water permeability and high strength of the coating.

The weight of the coating around the core depends on the composition and porosity of the coating, but generally should be present in an amount ranging from 3 to 30 wt %, based on the weight of the uncoated core. A coating weight of at least about 5 wt %, is typically preferred for sufficient strength for reliable performance, although lower coating weights can be used to achieve desire high water imbibing rates and, subsequently, higher release rates of tofacitinib from the dosage form. For tofacitinib-containing dosage forms, a coating weight gain of 5-10% is preferred to achieve the desired release performance.

While porous coatings based on CA, PEG or HPC, and water or methanol described above translate to excellent results, other pharmaceutically acceptable materials could be used in the coating so long as the coating has the requisite combination of high water permeability, high strength, and ease of fabrication and application. Further, such coatings may be dense, porous, or "asymmetric," having one or more dense layers and one or more porous layers such as those disclosed in U.S. Pat. Nos. 5,612,059 and 5,698,220, the pertinent disclosures of which are incorporated herein by reference.

The coating must also contain at least one delivery port in communication with the interior and exterior of the coating to allow for release of the tablet core contents to the exterior of the dosage form. The delivery port can range in size from about the size of the drug particles, and thus could be as small as 1 to 100 microns in diameter and may be termed pores, up to about 5000 microns in diameter. The shape of the port may be substantially circular, in the form of a slit, or other convenient shape to ease manufacturing and processing. The port(s) may be formed by post-coating mechanical or thermal means or with a beam of light (e.g., a laser), a beam of particles, or other high-energy source, or may be formed in situ by rupture of a small portion of the coating. Such rupture may be controlled by intentionally incorporating a relatively small weak portion into the coating. Delivery ports may also be formed in situ by erosion of a plug of water-soluble material or by rupture of a thinner portion of the coating over an indentation in the core. Delivery ports may be formed by coating the core such that one or more small regions remain uncoated. In addition, the delivery port can be a large number of holes or pores that may be formed during coating, as in the case of asymmetric membrane coatings, described in more detail herein, and of the type disclosed in U.S. Pat. Nos. 5,612,059 and 5,698,220, the disclosures of which are incorporated by reference. When the delivery pathways are pores there can be a multitude of such pores that range in size from 1 micron to greater than 100 microns. During operation, one or more of such pores may enlarge under the influence of the hydrostatic pressure generated during operation. The location of the delivery port(s) may be located anywhere on the tablet surface. Preferred locations of the delivery port(s) include the face of the tablet and the tablet band. A more preferred location includes approximately the center of the tablet band for round, SRC-shaped tablets and approximately the center of the tablet band along the major axis and/or approximately the center of the tablet band along the minor axis of the tablet band for capsule, caplet, oval, or modified oval shaped tablets. A most preferred location of the delivery port(s) is the approximate center of the tablet band along the major axis of the tablet band for capsule, caplet, oval, or modified oval shaped tablets.

Sustained Release—Reservoir Systems

Another class of tofacitinib sustained-release dosage forms of this invention includes membrane-moderated or reservoir systems. In this class, a reservoir of tofacitinib is surrounded by a rate-limiting membrane. The tofacitinib traverses the membrane by mass transport mechanisms well known in the art, including but not limited to dissolution in the membrane followed by diffusion across the membrane or diffusion through liquid-filled pores within the membrane. These individual reservoir system dosage forms may be large, as in the case of a tablet containing a single large reservoir, or multiparticulate, as in the case of a capsule containing a plurality of reservoir particles, each individually coated with a membrane. The coating can be nonporous, yet permeable to tofacitinib (for example tofacitinib may diffuse directly through the membrane), or it may be porous. As with other embodiments of this invention, the particular mechanism of transport is not believed to be critical.

Sustained release coatings as known in the art may be employed to fabricate the membrane, especially polymer coatings, such as a cellulose ester or ether, an acrylic polymer, or a mixture of polymers. Preferred materials include ethyl cellulose, cellulose acetate and cellulose acetate butyrate. The polymer may be applied as a solution in an organic solvent or as an aqueous dispersion or latex. The coating operation may be conducted in standard equipment such as a fluid bed coater, a Wurster coater, or a rotary bed coater.

If desired, the permeability of the coating may be adjusted by blending of two or more materials. A useful process for tailoring the porosity of the coating comprises adding a pre-determined amount of a finely-divided water-soluble material, such as sugars or salts or water-soluble polymers to a solution or dispersion (e.g., an aqueous latex) of the membrane-forming polymer to be used. When the dosage form is ingested into the aqueous medium of the GI tract, these water soluble membrane additives are leached out of the membrane, leaving pores which facilitate release of the drug. The membrane coating can also be modified by the addition of plasticizers, as known in the art.

A useful variation of the process for applying a membrane coating comprises dissolving the coating polymer in a mixture of solvents chosen such that as the coating dries, a phase inversion takes place in the applied coating solution, resulting in a membrane with a porous structure. Numerous examples of this type of coating system are given in European Patent Specification 0 357 369 B1, published Mar. 7, 1990, herein incorporated by reference.

The morphology of the membrane is not of critical importance so long as the permeability characteristics enumerated herein are met. The membrane can be amorphous or crystalline. It can have any category of morphology produced by any particular process and can be, for example, an interfacially-polymerized membrane (which comprises a thin rate-limiting skin on a porous support), a porous hydrophilic membrane, a porous hydrophobic membrane, a hydrogel membrane, an ionic membrane, and other such materials which are characterized by controlled permeability to tofacitinib.

A useful reservoir system embodiment is a capsule having a shell comprising the material of the rate-limiting membrane, including any of the membrane materials previously discussed, and filled with a tofacitinib drug composition. A particular advantage of this configuration is that the capsule may be prepared independently of the drug composition, thus process conditions that would adversely affect the drug can be used to prepare the capsule. One embodiment is a capsule having a shell made of a porous or a permeable polymer made by a thermal forming process. Another embodiment is a capsule shell in the form of an asymmetric membrane; e.g., a membrane that has a thin skin on one surface and most of whose thickness is constituted of a highly permeable porous material. A process for preparation of asymmetric membrane capsules comprises a solvent exchange phase inversion, wherein a solution of polymer, coated on a capsule-shaped mold, is induced to phase-separate by exchanging the solvent with a-miscible non-solvent. Examples of asymmetric membranes useful in this invention are disclosed in the aforementioned European Patent Specification 0 357 369 B1.

Another embodiment of the class of reservoir systems comprises a multiparticulate wherein each particle is coated with a polymer designed to yield sustained release of tofacitinib. The multiparticulate particles each comprise tofacitinib and one or more excipients as needed for fabrication and performance. The size of individual particles, as previously mentioned, is generally between about 50 micron and about 3 mm, although beads of a size outside this range may also be useful. In general, the beads comprise tofacitinib and one or more binders. As it is generally desirable to produce dosage forms which are small and easy to swallow, beads which contain a high fraction of tofacitinib relative to excipients are preferred. Binders useful in fabrication of these beads include microcrystalline cellulose (e.g., Avicel®, FMC Corp.), hydroxypropyl cellulose (HPC), hydroxypropyl methyl cellulose (HPMC), and related materials or combinations thereof. In general, binders which are useful in granulation and tabletting, such as starch, pregelatinized starch, and poly (N-vinyl-2-pyrrolidinone) (PVP) may also be used to form multiparticulates.

Reservoir system tofacitinib multiparticulates may be prepared using techniques known to those skilled in the art, including, but not limited to, the techniques of extrusion and spheronization, wet granulation, fluid bed granulation, and rotary bed granulation. In addition, the beads may also be prepared by building the tofacitinib composition (drug plus excipients) up on a seed core (such as a non-pareil seed) by a drug-layering technique such as powder coating or by applying the tofacitinib composition by spraying a solution or dispersion of tofacitinib in an appropriate binder solution onto seed cores in a fluidized bed such as a Wurster coater or a rotary processor. An example of a suitable composition and method is to spray a dispersion of a tofacitinib/hydroxypropylcellulose composition in water. Advantageously, tofacitinib can be loaded in the aqueous composition beyond its solubility limit in water.

A method for manufacturing the multiparticulate cores of this embodiment is the extrusion/spheronization process, as previously discussed for matrix multiparticulates. Another process and composition for this method involves using water to wet-mass blend of about 5 to 75% of microcrystalline cellulose with correspondingly about 95 to 25% tofacitinib. In another embodiment, the process involves the use of water to wet-mass blend of about 5-30% microcrystalline cellulose with correspondingly about 5-70% tofacitinib.

A sustained release coating as known in the art, especially polymer coatings, may be employed to fabricate the membrane, as previously discussed for reservoir systems. Suitable and preferred polymer coating materials, equipment, and coating methods also include those previously discussed.

The rate of tofacitinib release from the coated multiparticulates can also be controlled by factors such as the composition and binder content of the drug-containing core, the thickness and permeability of the coating, and the surface-to-volume ratio of the multiparticulates. It will be appreciated by those skilled in the art that increasing the thickness of the coating will decrease the release rate, whereas increasing the permeability of the coating or the surface-to-volume ratio of the multiparticulates will increase the release rate. If desired, the permeability of the coating may be adjusted by blending of two or more materials. A useful series of coatings comprises mixtures of water-insoluble and water-soluble polymers, for example, ethylcellulose and hydroxypropyl methylcellulose, respectively. A useful modification to the coating is the addition of finely-divided water-soluble material, such as sugars or salts. When placed in an aqueous medium, these water soluble membrane additives are leached out of the membrane, leaving pores which facilitate delivery of the drug. The membrane coating may also be modified by the addition of plasticizers, as is known to those skilled in the art. Another useful variation of the membrane coating utilizes a mixture of solvents chosen such that as the coating dries, a phase inversion takes place in the applied coating solution, resulting in a membrane with a porous structure.

Another embodiment is a multiparticulate comprising about 5-50% tofacitinib, the individual particles being coated with an aqueous dispersion of ethyl cellulose, which dries to form a continuous film.

Another embodiment is obtained when the tofacitinib beads are less than about 400 micron in size and are coated with a phase inversion membrane of ethyl cellulose or cellulose acetate.

Another embodiment is obtained when the tofacitinib beads are less than about 400 micron in size and are coated with an aqueous dispersion of ethyl cellulose, which dries to form a continuous film.

Another embodiment is obtained when the tofacitinib beads are less than about 300 micron in size and are coated with an aqueous dispersion of ethyl cellulose, which dries to form a continuous film.

Delayed Release and Controlled Release Components

Another class of dosage forms includes those forms which incorporate a delay before the onset of controlled release of tofacitinib. One embodiment can be illustrated by a tablet comprising a core containing tofacitinib coated with a first coating of a polymeric material of the type useful for controlled release of tofacitinib and a second coating of the type useful for delaying release of drugs when the dosage form is ingested. The first coating is applied over and surrounds the tablet. The second coating is applied over and surrounds the first coating.

The tablet can be prepared by techniques well known in the art and contains a therapeutically useful amount of tofacitinib plus such excipients as are necessary to form the tablet by such techniques.

The first coating may be a controlled release coating as known in the art, especially polymer coatings, to fabricate the membrane, as previously discussed for reservoir systems. Suitable polymer coating materials, equipment, and coating methods also include those previously discussed.

Materials useful for preparing the second coating on the tablet include polymers known in the art as enteric coatings for delayed-release of pharmaceuticals. These most commonly are pH-sensitive materials such as cellulose acetate phthalate, cellulose acetate trimellitate, hydroxypropyl methyl cellulose phthalate, poly(vinyl acetate phthalate), and acrylic copolymers such as Eudragit L-100 (Rohm-Pharma), Eudragit L 30 D-55, Eudragit S 100, Eudragit FS 30D, and related materials, as more fully detailed below under "Delayed Release". The thickness and type of the delayed-release coating is adjusted to give the desired delay property. In general, thicker coatings are more resistant to erosion and, consequently, yield a longer delay as do coatings which are designed to dissolve above pH 7. Preferred coatings typically range from about 10 micron in thickness to about 3 mm in thickness and more preferably 10 um to 500 um.

When ingested, the twice-coated tablet passes through the stomach, where the second coating prevents release of the tofacitinib under the acidic conditions prevalent there. When the tablet passes out of the stomach and into the small intestine, where the pH is higher, the second coating erodes or dissolves according to the physicochemical properties of the chosen material. Upon erosion or dissolution of the second coating, the first coating prevents immediate or rapid release of the tofacitinib and modulates the release so as to prevent the production of high concentrations, thereby minimizing side-effects.

Another embodiment comprises a multiparticulate wherein each particle is dual coated as described above for tablets, first with a polymer designed to yield controlled release of the tofacitinib and then coated with a polymer designed to delay onset of release in the environment of the GI tract when the dosage form is ingested. The beads contain tofacitinib and may contain one or more excipients as needed for fabrication and performance. Multiparticulates which contain a high fraction of tofacitinib relative to binder are desired. The multiparticulate may be of a composition and be fabricated by any of the techniques previously disclosed for multiparticulates used to make reservoir systems (including extrusion and spheronization, wet granulation, fluid bed granulation, and rotary bed granulation, seed building, and so forth).

The controlled release coating may be as known in the art, especially polymer coatings, to fabricate the membrane, as previously discussed for reservoir systems. Suitable polymer coating materials, equipment, and coating methods also include those previously discussed.

The rate of tofacitinib release from the controlled-release-coated multiparticulates (e.g., the multiparticulates before they receive the delayed-release coating) and methods of modifying the coating are also controlled by the factors previously discussed for reservoir system tofacitinib multiparticulates.

The second membrane or coating for dual coated multiparticulates is a delayed-release coating which is applied over the first controlled-release coating, as disclosed above for tablets, and may be formed from the same materials. It should be noted that the use of the so-called "enteric" materials to practice this embodiment differs significantly from their use to produce conventional enteric dosage forms. With conventional enteric forms, the object is to delay release of the drug until the dosage form has passed the stomach and then to deliver the dose shortly after emptying from the stomach. Dosing of tofacitinib directly and completely to the duodenum is undesirable, however, due to local metabolism which is sought to be minimized or avoided by this invention. Therefore, if conventional enteric polymers are to be used to practice this embodiment, it may be necessary to apply them significantly more thickly than in conventional practice, in order to delay drug release until the dosage form reaches the lower GI tract. However, it is preferred to effect a controlled delivery of tofacitinib after the delayed-release coating has dissolved or eroded, therefore the benefits of this embodiment may be realized with a proper combination of delayed-release character with controlled-release character, and the delayed-release part alone may or may not necessarily conform to USP enteric criteria. The thickness of the delayed-release coating is adjusted to give the desired delay property. In general, thicker coatings are more resistant to erosion and, consequently, yield a longer delay.

It should also be noted, that sustained release osmotic systems as defined above, could also be defined in the current delay then controlled release category. Typical osmotic sustained release systems have an initial delay of 0.5-6 hours prior to drug release in a controlled fashion. In this manner, a standard osmotic monolithic or bilayer sustained release system embodies the definition of delay followed by controlled release.

Bursting Osmotic Beads and Cores (Pulsatile Delivery)

In a further embodiment ("bursting osmotic core device"), tofacitinib is incorporated in an osmotic bursting device which comprises a tablet core or bead core containing tofacitinib and, optionally, one or more osmagents. Devices of this type have been generally disclosed in Baker, U.S. Pat. No. 3,952,741, which is incorporated herein by reference. Examples of osmagents are sugars such as glucose, sucrose, mannitol, lactose, and the like; and salts such as sodium chloride, potassium chloride, sodium carbonate, and the like; water-soluble acids such as tartaric acid, fumaric acid, and the like. The tofacitinib-containing tablet core or bead core is coated with a polymer which forms a semipermeable membrane, that is, a membrane which is permeable to water but is substantially impermeable to tofacitinib. Examples of polymers which provide a semipermeable membrane are cellulose acetate, cellulose acetate butyrate, and ethylcellulose, preferably cellulose acetate. The semipermeable coating membrane may alternatively be composed of one or more waxes, such as insect and animal waxes such as beeswax, and vegetable waxes such as carnauba wax and hydrogenated vegetable oils. A melt mixture of a polyethylene glycol, e.g., polyethylene glycol-6000, and a hydrogenated oil, e.g., hydrogenated castor oil, may be used as a coating, as described for isoniazid tablets by Yoshino (Capsugel Symposia Series; Current Status on Targeted Drug Delivery to the Gastrointestinal Tract; 1993; pp. 185-190). Some preferred semipermeable coating materials are cellulose esters and cellulose ethers, polyacrylic acid derivatives such as polyacrylates and polyacrylate esters, and polyvinyl alcohols and polyalkenes such as ethylene vinyl alcohol copolymer. Other semipermeable coating materials are cellulose acetate and cellulose acetate butyrate.

When a coated tablet or bead of the "bursting osmotic core" embodiment of this invention is placed in an aqueous environment of use, water passes through the semipermeable membrane into the core, dissolving a portion of the tofacitinib and osmagent, generating a colloidal osmotic pressure which results in bursting of the semipermeable membrane and release of tofacitinib into the aqueous environment. By choice of bead or tablet core size and geometry, identity and quantity of osmagent, and thickness of the semipermeable membrane, the time lag between placement of the dosage form into the aqueous environment of use and release of the enclosed tofacitinib may be chosen. It will be appreciated by those skilled in the art that increasing the surface-to-volume ratio of the dosage form, and increasing the osmotic activity of the osmagent serve to decrease the time lag, whereas increasing the thickness of the coating will increase the time lag. Osmotic-bursting devices of this invention are those which exhibit substantially no release of tofacitinib from the dosage form until the dosage form has exited the stomach and has resided in the small intestine for about 15 minutes or greater. Some osmotic-bursting devices exhibit substantially no release of tofacitinib from the dosage form until the dosage form has exited the stomach and has resided in the small intestine for about 30 minutes or greater. Other osmotic-bursting devices exhibit substantially no release of tofacitinib from the dosage form until the dosage form has exited the stomach and has resided in the small intestine for about 90 minutes or greater. Still other osmotic-bursting devices exhibit substantially no release of tofacitinib from the dosage form until the dosage form has exited the stomach and has resided in the small intestine for and most preferably 3 hours or greater, thus assuring that minimal tofacitinib is released in the duodenum and upper small intestine. A bursting osmotic core tablet or bead has a tablet or bead core which may contain from about 10-95% tofacitinib, about 0-60% osmagent, as described above, and about 5-20% other pharmaceutical aids such as binders and lubricants. The semipermeable membrane coating on a tablet, such as a cellulose acetate coating, is present at a weight corresponding to from about 2% to about 30%, preferably from about 3% to about 10%, of the weight of the tablet core. The semipermeable membrane coating on a bead, such as a cellulose acetate coating, is present at a weight corresponding to from about 2% to about 80% of the weight of the bead core. In another embodiment, the semipermeable coating on a bead is present at a weight corresponding to from 3% to 30% of the weight of the bead core.

A bursting osmotic core device possesses no mechanism for "sensing" that the device has exited the stomach and entered the duodenum. Thus devices of this type release tofacitinib at a predetermined time after entering an aqueous environment, e.g., after being swallowed. In the fasted state, indigestible non-disintegrating solids, such as the "bursting osmotic core devices" of this invention, are emptied from the stomach during phase III of the Interdigestive Migrating Myoelectric Complex (IMMC), which occurs approximately every 2 hr in the human. Depending on the stage of the IMMC at the time of dosing in the fasted state, a bursting osmotic core device may exit the stomach almost immediately after dosing, or as long as 2 hr after dosing. In the fed state, indigestible non-disintegrating solids, which are <11 mm in diameter, will empty slowly from the stomach with the contents of the meal (Khosla and Davis, Int. J. Pharmaceut. 62 (1990) R9-R11). If the indigestible non-disintegrating solid is greater than about 11 mm in diameter, e.g., about the size of a typical tablet, it will be retained in the stomach for the duration of the digestion of the meal, and will exit into the duodenum during phase III of an IMMC, after the entire meal has been digested and has exited the stomach. The release of tofacitinib can be delayed until about 15 min or more. The release of tofacitinib can be delayed until 30 minutes or more. The release of tofacitinib can be delayed until about 90 minutes or greater. The release of tofacitinib can be delayed until about 3 hours or greater after the dosage form has exited the stomach. A bursting osmotic core device starts to release tofacitinib at about 2.5 hr after entering an aqueous environment, e.g., after ingestion, to more reliably assure that the device releases its tofacitinib distal to the duodenum, when dosed in the fasted state. Another "bursting osmotic core device" will start to release tofacitinib at about 4 hr after entering an aqueous environment. This 4 hr delay permits dosing in the fed state, and allows for an about 3.5 hr retention in the fed stomach, followed by an approximately 30 minute delay after the dosage form has exited from the stomach. In this way, the release of tofacitinib into the most sensitive portion of the gastrointestinal tract, the duodenum, is minimized.

In a further embodiment, a "bursting coated swelling core", a tofacitinib-containing tablet or bead is prepared which also comprises 25-70% of a swellable material, such as a swellable colloid (e.g., gelatin), as described in Milosovich, U.S. Pat. No. 3,247,066, incorporated herein by reference. Swelling core materials are hydrogels, e.g., hydrophilic polymers which take up water and swell, such as polyethylene oxides, polyacrylic acid derivatives such as polymethyl methacrylate, polyacrylamides, polyvinyl alcohol, poly-N-vinyl-2-pyrrolidone, carboxymethylcellulose, starches, and the like. Swelling hydrogels for this embodiment include polyethylene oxides, carboxymethylcellulose and croscarmellose sodium. The colloid/hydrogel-containing tofacitinib-containing core tablet or bead is coated, at least in part, by a semipermeable membrane. Examples of polymers which provide a semipermeable membrane are cellulose acetate and cellulose acetate butyrate, and ethylcellulose. The semipermeable coating membrane may alternatively be composed of one or more waxes, such as insect and animal waxes such as beeswax, and vegetable waxes such as carnauba wax and hydrogenated vegetable oils. A melt mixture of a polyethylene glycol, e.g., polyethylene glycol-6000, and a hydrogenated oil, e.g., hydrogenated castor oil, may be used as a coating, as described for isoniazid tablets by Yoshino (Capsugel Symposia Series; Current Status on Targeted Drug Delivery to the Gastrointestinal Tract; 1993; pp. 185-190). Some semipermeable coating materials are cellulose esters and cellulose ethers, polyacrylic acid derivatives such as polyacrylates and polyacrylate esters, polyvinyl alcohols and polyalkenes such as ethylene vinyl alcohol copolymer, cellulose acetate and cellulose acetate butyrate.

When a coated tablet or bead having a bursting coated swelling core is placed in an aqueous environment of use, water passes through the semipermeable membrane into the core, swelling the core and resulting in bursting of the semipermeable membrane and release of tofacitinib into the aqueous environment. By choice of bead or tablet core size and geometry, identity and quantity of swelling agent, and thickness of the semipermeable membrane, the time lag between placement of the dosage form into the aqueous environment of use and release of the enclosed tofacitinib may be chosen. Preferred bursting coated swelling core devices of this invention are those which exhibit substantially no release of tofacitinib from the dosage form until the dosage form has exited the stomach and has resided in the small intestine for about 15 minutes or greater, preferably about 30 minutes or greater, thus assuring that minimal tofacitinib is released in the duodenum.

A bursting coated swelling core tablet or bead has a tablet or bead core which may contain from about 10-70% tofacitinib; about 15-60% swelling material, e.g., hydrogel; about 0-15% optional osmagent; and about 5-20% other pharmaceutical aids such as binders and lubricants. The semipermeable membrane coating on a tablet, preferably a cellulose acetate coating, is present at a weight corresponding to from about 2% to about 30%, preferably from 3% to 10%, of the weight of the tablet core. The semipermeable membrane coating on a bead, preferably a cellulose acetate coating, is present at a weight corresponding to from about 2% to about 80%, preferably from 3% to 30%, of the weight of the bead core.

A bursting coated swelling core device possesses no mechanism for sensing that the device has exited the stomach and entered the duodenum. Thus devices of this type release their tofacitinib contents at a predetermined time after entering an aqueous environment, e.g., after being swallowed, as previously discussed for bursting osmotic core devices, and the same consideration and preferences apply to making bursting coated swelling core devices. Bursting coated swelling core devices may be combined with immediate release devices to create a dosage form that will release drug both immediately after administration and at one or more additional predetermined times after dosing.

In a further embodiment, a "pH-triggered osmotic bursting device", tofacitinib is incorporated into a device of the type described in allowed commonly assigned U.S. Pat. No. 5,358,502, issued Oct. 25, 1994, incorporated herein by reference. The device comprises tofacitinib and optionally one or more osmagents, surrounded at least in part by a semipermeable membrane. The semipermeable membrane is permeable to water and substantially impermeable to tofacitinib and osmagent. Useful osmagents are the same as those described above for bursting osmotic core devices. Useful semipermeable membrane materials are the same as those described above for bursting osmotic core devices. A pH-trigger means is attached to the semipermeable membrane. The pH-trigger means is activated by a pH above 5.0, and triggers the sudden delivery of the tofacitinib. In this embodiment, the pH-trigger means comprises a membrane or polymer coating which surrounds the semipermeable coating. The pH-trigger coating contains a polymer which is substantially impermeable and insoluble in the pH range of the stomach, but becomes permeable and soluble at about the pH of the duodenum, about pH 6.0.

Exemplary pH-sensitive polymers are polyacrylamides, phthalate derivatives such as acid phthalates of carbohydrates, amylose acetate phthalate, cellulose acetate phthalate, other cellulose ester phthalates, cellulose ether phthalates, hydroxypropylcellulose phthalate, hydroxypropylethylcellulose phthalate, hydroxypropylmethylcellulose phthalate, methylcellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinylacetate phthalate copolymer, styrene and maleic acid copolymers, polyacrylic acid derivatives such as acrylic acid and acrylic ester copolymers, polymethacrylic acid and esters thereof, poly acrylic methacrylic acid copolymers, shellac, and vinyl acetate and crotonic acid copolymers.

Preferred pH-sensitive polymers include shellac; phthalate derivatives, particularly cellulose acetate phthalate, polyvinylacetate phthalate, and hydroxypropylmethylcellulose phthalate; polyacrylic acid derivatives, particularly polymethyl methacrylate blended with acrylic acid and acrylic ester copolymers; and vinyl acetate and crotonic acid copolymers. As described above cellulose acetate phthalate is available as a latex under the tradename Aquateric® (registered trademark of FMC Corp., Philadelphia, Pa.), and acrylic copolymers are available under the tradenames Eudragit-R® and Eudragit-L®. For appropriate application in this embodiment, these polymers should be plasticized utilizing plasticizers described above. The pH-trigger coating may also comprise a mixture of polymers, for example cellulose acetate and cellulose acetate phthalate. Another suitable mixture comprises Eudragit-L® and Eudragit-S®; the ratio of the two, and the coating thickness, defining the sensitivity of the "trigger", e.g., the pH at which the outer pH-trigger coating weakens or dissolves.

A pH-triggered osmotic bursting device generally operates as follows. After oral ingestion, the pH-trigger coating, which surrounds the semipermeable coating, which in turn surrounds the tofacitinib-containing core tablet or bead, remains undissolved and intact in the stomach. In the stomach, water may or may not commence penetration through the pH-trigger coating and the semipermeable coating, thus starting hydration of the core, which contains tofacitinib and optional osmagent. After the device has exited the stomach and has entered the small intestine, the pH-trigger coating rapidly disintegrates and dissolves, and water passes through the semipermeable coating, dissolving tofacitinib and optional osmagent within the core. As the colloidal osmotic pressure across the semipermeable coating exceeds some threshold value, the semipermeable coating fails, and the device bursts, releasing tofacitinib. It is preferred that this bursting and release of tofacitinib occur at about 15 minutes or more, preferably 30 minutes or more, after the pH-triggered osmotic bursting device exits the stomach and enters the duodenum, thus minimizing exposure of the sensitive duodenum to tofacitinib.

For a pH-triggered osmotic bursting device, the lag-time or delay-time is controlled by the choice and amount of osmagent in the core, by the choice of semipermeable coating, and by the thickness of the semipermeable coating. It will be appreciated by those skilled in the art, for example, that a thicker semipermeable coating will result in a longer delay after the device has exited the stomach. A preferred pH-triggered osmotic bursting device is a bead or tablet core of tofacitinib with optional osmagent, coated with a 3-20% by weight cellulose acetate membrane, coated with a 3-20% by weight membrane composed of about 1:1 cellulose acetate/cellulose acetate phthalate. Another preferred pH-triggered osmotic bursting device is a bead or tablet core of tofacitinib with optional osmagent, coated with a 3-20% by weight cellulose acetate membrane, coated with a 3-20% by weight membrane comprising from about 9:1 to about 1:1 Eudragit-L®/Eudragit-S®.

Advantageously, because a pH-triggered osmotic bursting device possesses a mechanism for sensing that the device has exited the stomach, intersubject variability in gastric emptying is not significant.

In a further embodiment, a "pH-triggered bursting coated swelling core", a tablet core or bead containing tofacitinib and a swelling material is coated with a semipermeable coating which is further coated with a pH-sensitive coating. The core composition, including choice of swelling material is as described above for the bursting coated swelling core embodiment. The choice of semipermeable coating material and pH-sensitive coating material are as described above for the "pH-triggered osmotic core" embodiment. This device is described in detail in commonly-assigned copending U.S. patent application Ser. No. 08/023,227, filed Feb. 25, 1993, incorporated herein by reference.

A pH-triggered bursting swelling core embodiment generally operates as follows. After oral ingestion, the pH-trigger coating, which surrounds the semi-permeable coating, which in turn surrounds the tofacitinib-containing core tablet or bead, remains undissolved and intact in the stomach. In the stomach, water may or may not commence penetration through the pH-trigger coating and the semipermeable coating, thus starting hydration of the core, which contains tofacitinib and water-swellable material, preferably a hydrogel. When the pH-triggered bursting swelling core device exits the stomach and enters the small intestine, the pH-trigger coating rapidly disintegrates and dissolves, and water passes through the semipermeable coating, dissolving tofacitinib and swelling the water-swellable material within the core. As the swelling pressure across the semipermeable coating exceeds some threshold value, the semipermeable coating fails, and the device bursts, releasing tofacitinib. This bursting and release of tofacitinib occurs at about 15 minutes or more, around about 30 minutes, after the pH-triggered bursting swelling core device exits the stomach and enters the duodenum, thus minimizing exposure of the sensitive duodenum to tofacitinib.

For the "pH-triggered bursting swelling core" device, the lag-time or delay-time can be controlled by the choice and amount of swelling material in the core, by the choice of semipermeable coating, and by the thickness of the semipermeable coating. It will be appreciated by those skilled in the art, for example, that a thicker semipermeable coating will result in a longer delay after the device has exited the stomach. A pH-triggered bursting swelling core device contains a bead or tablet core of tofacitinib with synthetic hydrogel, preferably carboxymethylcellulose, coated with a 3-20% by weight cellulose acetate membrane, coated with a 3-20% by weight membrane composed of about 1:1 cellulose acetate/cellulose acetate phthalate. Another pH-triggered bursting swelling core device contains a bead or tablet core of tofacitinib with synthetic hydrogel, preferably carboxymethylcellulose, coated with a 3-20% by weight cellulose acetate membrane, coated with a 3-20% by weight membrane composed of from about 9:1 to about 1:1 Eudragit-L®/Eudragit-S®.

Advantageously, because a pH-triggered bursting swelling core device possesses a mechanism for sensing that the device has exited the stomach, intersubject variability in gastric emptying is not significant. pH-triggered bursting swelling core devices may be combined with immediate release devices to create a dosage form that will release drug both immediately after administration and at one or more additional predetermined locations in the GI tract after dosing.

A current review of this bursting technology is Journal of Controlled Release; 134 (2009) 74-80 and herein incorporated as reference in its entirety.

Delayed release embodiments of the invention are solid dosage forms for oral administration comprising tofacitinib and a pharmaceutically acceptable carrier, which release not more than 10% of their incorporated tofacitinib into a mammal's stomach, and which release not more than an additional 10% during the first 15 minutes after entering said mammal's duodenum. The timing of release of tofacitinib in the stomach or duodenum may be tested utilizing a variety of approaches including, but not limited to, x-ray evaluation, nuclear magnetic resonance imaging, gamma scintigraphy, or direct sampling of the gastric and duodenal contents via intubation. These tests, while possible, can be very difficult to carry out in humans. A more convenient test for a delayed release embodiment of the current invention is a two stage in vitro dissolution test.

The invention will be illustrated in the following non-limiting examples.

EXAMPLES

Example 1. Extrudable Core System Osmotic Tablet 22 mg Tablet Core

One-half of the batch quantity of sorbitol, 2663.01 grams (also see Table 1 below), was added to a 28 L bin. The batch quantity of Copovidone, 420.00 grams, was then added to the 28 L bin. The batch quantity of Tofacitinib, 623.98 g, was then added to the 28 L bin. The batch quantity of Hydroxycellulose, 560.00 grams, was then added to the 28 L bin. The remaining one-half of the batch quantity of sorbitol, 2663.01 grams was added to the 28 L bin. All of the components were blended in the bin for 15 minutes at 12+/−1 RPM.

The blend was passed through a Comil rotary mill equipped with a 0.032" screen and a round edge impeller running at approximately 950 RPM. The blend was collected in a second 28 L bin. The bin contents were blended for 10 minutes at 15+/−1 RPM.

Magnesium stearate, 70 g, was passed through an 850-micron mesh screen and was added to the bin and contents were blended for 5.5 minutes at 12+/−1 RPM. Final blend was transferred to the hopper of a Fette rotary tablet press. Tablets were compressed using 0.2620"×0.5240" modified oval tooling, to an average target weight of 400 mg+/−5%, average target thickness of 5.35 mm+/−0.05 mm, and a target hardness of 13 kP. Tablets were passed through a deduster and a metal detector.

TABLE 1

| # | Material | Function | Composition (%) | Grams |
|---|---|---|---|---|
| 1 | Tofacitinib Citrate | Active | 8.914 | 623.98 |
| 2 | Sorbitol | Osmagen | 76.086 | 5326.02 |
| 3 | Hydroxyethylcellulose | Viscosifying Agent | 8.000 | 560.00 |
| 4 | Kollidon VA 64 (copovidone) | Binder | 6.000 | 420.00 |
| 5 | Magnesium Stearate | Lubricant | 1.000 | 70.00 |
|   | Core Tablet Weight | — | 100% | 7000.00 g |

11 mg Tablet Core

One-half of the batch quantity of sorbitol, 2819.01 grams (also see Table 2 below), was added to a 28 L bin. The batch quantity of Copovidone, 420.00 grams, was then added to the 28 L bin. The batch quantity of Tofacitinib, 311.99 g, was then added to the 28 L bin. The batch quantity of Hydroxycellulose, 560.00 grams, was then added to the 28 L bin. The remaining one-half of the batch quantity of sorbitol, 2819.0 grams was added to the 28 L bin. All of the components were blended in the bin for 15 minutes at 12+/−1 RPM.

The blend was passed through a Comil rotary mill equipped with a 0.032" screen and a round edge impeller running at approximately 950 RPM. The blend was collected in a second 28 L bin. The bin contents were blended for 10 minutes at 15+/−1 RPM.

Magnesium stearate, 70 g, was passed through a 850-micron mesh screen and was added to the bin and contents were blended for 5.25 minutes at 12+/−1 RPM. Final blend was transferred to the hopper of a Fette rotary tablet press. Tablets were compressed using 0.2620"×0.5240" modified oval tooling, to an average target weight of 400 mg+1-5%, average target thickness of 5.35 mm+/−0.05 mm, and a target hardness of 15 kP. Tablets were passed through a deduster and a metal detector.

TABLE 2

| # | Material | Function | Composition (%) | Grams |
|---|---|---|---|---|
| 1 | Tofacitinib Citrate | Active | 4.457 | 311.99 |
| 2 | Sorbitol | Osmagen | 80.543 | 5638.01 |
| 3 | Hydroxyethylcellulose | Viscosifying Agent | 8.000 | 560.00 |
| 4 | Kollidon VA 64 (copovidone) | Binder | 6.000 | 420.00 |
| 5 | Magnesium Stearate | Lubricant | 1.000 | 70.00 |
|   | Core Tablet Weight | — | 100% | 7000.00 g |

Tablet Coating and Drilling 4.049-kilogram coating solution was prepared according to the following steps: First, the entire 396.0 grams of water (also see Table 3 below) and 1464.0 grams of acetone were added to a 5-Liter vessel and mixed for 5 minutes. 32.4 grams of hydroxypropyl cellulose were added to the mixture and mixed for 5 minutes. 48.6 grams of cellulose acetate were added to the mixture and mixed for 5 minutes. The remaining 2108 grams of acetone were added to the mixture and mixed for 3 hours. This procedure created a 2% solids (w/w) solution.

TABLE 3

| Composition of duration 1 coated tablet | % in coating | mg/tablet | coat w/w (%) | Batch Quantity (Grams) |
|---|---|---|---|---|
| 1. Tofacitinib Citrate Tablet Core | — | 400 | — | — |
| 2. Cellulose Acetate (Type 398-10) | 1.2% | 14.4 | 3.6 | 48.6 |
| 3. Hydroxypropyl Cellulose (Klucel EF) | 0.8% | 9.6 | 2.4 | 32.4 |
| 4. Acetone | 88.2% | (1058.4) | — | 3572.0 |
| 5. Purified water | 9.8% | (117.6) | — | 396.0 |
| Total Weight | 100% | 424 | 6.0 | 4049.0 |

900 grams of the 400 mg weight oval tablets were coated in a Vector LDCS-5 with a 1.5-Liter semi-perforated pan operating at 20 rpm and an airflow of 30 CFM having an exhaust temperature of 40 deg C. The 2% solids (w/w) solution was applied until the wet weight gain reached a level of 6.2%. The tablets were then removed from coating pan and dried at 40 C for 16 hours.

A single hole (1000 micron) was drilled in the end of the band of the oval tablet. The hole can be drilled either by mechanical means or via laser ablation. A coating of 6% provided the following release in pH 6.8 media, paddles at 50 rpm based on Dissolution test 1 (Table 4):

TABLE 4

| Time (hr) | 11 mg tablet % Drug Dissolved | 22 mg tablet % Drug Dissolved |
|---|---|---|
| 1 | 11 | 15 |
| 2.5 | 55 | 61 |
| 5 | 87 | 92 |

Example 2. 200 mg Extrudable Core System Osmotic Tablets with Acetone:Methanol Coating Solution 11 mg Tablet Core One-half of the batch quantity of sorbitol, 38.014 kilograms (also see Table 5 below), was added to a 300 L bin. The batch quantity of Copovidone, 6.00 kilograms, was then added to the 300 L bin. The batch quantity of Tofacitinib, 8.914 kilograms, was then added to the 300 L bin. The batch quantity of Hydroxycellulose, 8.00 kilograms, was then added to the 300 L bin. The remaining one-half of the batch quantity of sorbitol, 38.014 grams was added to the 300 L bin. All materials were added via a vacuum transfer system and passed through a Comil rotary mill equipped with a 0.032" screen and a round edge impeller running at approximately 1400 RPM. All of the components are blended in the bin for 20 minutes at 12+/−1 RPM.

The blend was passed through a Comil rotary mill equipped with a 0.032" screen and a round edge impeller running at approximately 1400 RPM. The blend was collected in a second 300 L bin. The bin contents were blended for 20 minutes at 12+/−1 RPM.

Magnesium stearate, 1.00 kilograms, was passed through a 850-micron mesh screen and was added to the bin and contents are blended for 5 minutes at 12+/−1 RPM. Tablets were compressed using 0.2080"×0.4160" modified oval tooling on a Manesty Mark IV rotary tablet press, to an average target weight of 200 mg+/−5%, average target thickness of 4.17 mm+/−0.05 mm, and a target hardness of 10 kP. Tablets were passed through a deduster and a metal detector.

TABLE 5

| # | Material | Function | Composition (%) | 100 kg Batch |
|---|---|---|---|---|
| 1 | Tofacitinib Citrate | Active | 8.914 | 8.914 |
| 2 | Sorbitol | Osmagen | 76.086 | 76.086 |
| 3 | Hydroxyethylcellulose | Viscosifying Agent | 8.000 | 8.00 |
| 4 | Copovidone | Binder | 6.000 | 6.00 |
| 5 | Magnesium Stearate | Lubricant | 1.000 | 1.00 |
|   | Core Tablet Weight | — | 100% | 100.00 kg |

22 mg Tablet Core

One-half of the batch quantity of sorbitol, 33.086 kilograms (also see Table 6 below), was added to a 300 L bin. The batch quantity of Colloidal Silicon Dioxide, 1.00 kg, was then added to the 300 L bin. The batch quantity of Copovidone, 6.00 kilograms, was then added to the 300 L bin. The batch quantity of Tofacitinib, 8.914 kilograms, was then added to the 300 L bin. The batch quantity of Hydroxycellulose, 8.00 kilograms, was then added to the 300 L bin. The remaining one-half of the batch quantity of sorbitol, 33.086 grams was added to the 300 L bin. All materials were added via a vacuum transfer system and passed through a Comil rotary mill equipped with a 0.032" screen and a round edge impeller running at approximately 1400 RPM. All the components were blended in the bin for 20 minutes at 12+/−1 RPM.

The blend was passed through a Comil rotary mill equipped with a 0.032" screen and a round edge impeller running at approximately 1400 RPM. The blend was collected in a second 300 L bin. The bin contents were blended for 20 minutes at 12+/−1 RPM.

Magnesium stearate, 1.00 kilograms, was passed through a 850-micron mesh screen and was added to the bin and contents are blended for 5 minutes at 12+/−1 RPM. Tablets were compressed using 0.2080"×0.4160" modified oval tooling on a Manesty Mark IV rotary tablet press, to an average target weight of 200 mg+/−5%, average target thickness of 4.17 mm+/−0.05 mm, and a target hardness of 11 kP. Tablets were passed through a deduster and a metal detector.

TABLE 6

| # | Material | Function | Composition (%) | 100 kg Batch |
|---|---|---|---|---|
| 1 | Tofacitinib Citrate | Active | 17.828 | 17.828 |
| 2 | Sorbitol | Osmagen | 66.172 | 66.172 |
| 3 | Hydroxyethylcellulose | Viscosifying Agent | 8.000 | 8.00 |
| 4 | Copovidone | Binder | 6.000 | 6.00 |
| 5 | Colloidal Silicon Dioxide | Glidant | 1.000 | 1.00 |
| 6 | Magnesium Stearate | Lubricant | 1.000 | 1.00 |
|   | Core Tablet Weight | — | 100% | 100.00 kg |

The 750-kilogram coating solution was prepared according to the following steps (see also Table 7): First, the entire 147.0 kilograms of methanol and 580.5 grams of acetone were added to a 250-gallon vessel. 13.5 kilograms of cellulose acetate were added to the mixture. 9.0 kilogram of hydroxypropyl cellulose were added to the mixture. The contents of the container were mixed for 1 hour. This procedure created a 3% solids (w/w) solution.

TABLE 7

| Composition of coated 200 mgW tablet | % in coating | mg/ tablet | coat w/w (%) | Batch Quantity (kilograms) |
|---|---|---|---|---|
| 1. Tofacitinib Citrate Tablet Core | — | 200 | — | — |
| 2. Cellulose Acetate (Type 398-10) | 1.8% | 7.9 | 4.0 | 13.5 |
| 3. Hydroxypropyl Cellulose (Klucel EF) | 1.2% | 5.3 | 2.6 | 9.0 |
| 4. Methanol | 19.6% | (86.2) | — | 147.0 |
| 5. Acetone | 77.4% | (340.6) | — | 580.5 |
| Total Weight | 100% | 213.2 | 6.6 | 750.0 |

250 kilograms of the 200 mg weight oval tablets were coated in a Vector HC-130 operating at 8 rpm and an airflow of 1000 CFM having an exhaust temperature of 28 deg C. The 3% solids (w/w) solution was applied until the wet weight gain reached a level of 6.8%. The tablets were then removed from the coating pan and dried at 45 C for 24 hours.

A single hole (600 micron) was drilled in the end of the band of the oval tablet. The hole can be drilled either by mechanical means or via laser ablation. A coating of 6.6% provided the following release in pH 6.8 media, paddles at 50 rpm based on Dissolution test 1 (Table 8):

TABLE 8

| Time (hr) | 11 mg tablet % Drug Dissolved | 22 mg tablet % Drug Dissolved |
|---|---|---|
| 1 | 11 | 10 |
| 2.5 | 55 | 55 |
| 5 | 85 | 82 |

Example 3. 200 mg Extrudable Core System Osmotic Tablets Cellulose Acetate and Polyethylene Glycol Coating Membrane 11 mg and 22 mg tofacitinib sustained release tablet cores were prepared as described in Example 2.

The 1200-gram coating solution was prepared according to the following steps (see also Table 9): First, 60 grams of water and 19.2 grams of polyethylene glycol were added to a 5-liter vessel and stirred until the solution was clear. 60 grams of methanol and 0.504 grams of BHA were added to the solution and stirred until clear. 1031.496 grams of acetone and 28.8 grams of cellulose acetate were added to the mixture. The contents of the container were mixed for 3 hours. This procedure created a 4% solids (w/w) solution.

TABLE 9

| # | Material | Composition (%) | Grams |
|---|---|---|---|
| 1 | Cellulose Acetate (Type 398-10) | 2.400% | 28.8 |
| 2 | Polyethylene Glycol (PEG 3350) | 1.600% | 19.2 |
| 3 | Butylated Hydroxyanisole (BHA) | 0.042% | 0.504 |
| 4 | Purified Water | 5.000% | 60.0 |
| 5 | Methanol | 5.000% | 60.0 |
| 6 | Acetone | 85.958% | 1031.496 |
|   |   | 100% |   |

240 grams of the 200 mg weight oval tablets were coated in a Vector LDCS-5 operating at 30 rpm and an airflow of 40 CFM having an exhaust temperature of 28 deg C. The 3% solids (w/w) solution was applied until the wet weight gain reached a level of 9.2%. The tablets were then removed from the coating pan and dried at 40 C for 16 hours.

A single hole (600 micron) was drilled in the end of the band of the oval tablet. The hole can be drilled either by mechanical means or via laser ablation. A coating of 9% provides the following release in pH 6.8 media, paddles at 50 rpm based on Dissolution test 1 (Table 10):

TABLE 10

| Time (hr) | 11 mg tablet % Drug Dissolved | 22 mg tablet % Drug Dissolved |
|---|---|---|
| 1 | 28 | 30 |
| 2.5 | 72 | 70 |
| 5 | 92 | 90 |

Example 4. Hydrophilic Matrix Controlled Release Tablet

The metal surfaces of a 10 L bin were pre-coated by adding the batch quantity (also see Table 11 below) 1484.85 g of Lactose Fast Flo 316 and blending for 2 minutes at 12+/−1 RPM. The batch quantity of Tofacitinib, 171.15 g, was added to the 10 L bin and folded into the lactose monohydrate. The Tofacitinib container was rinsed with some of the lactose monohydrate from the 10 L bin. The batch quantity of Hypromellose, 720 g, was added to the 10 L bin. All of the components were blended in the bin for 10 minutes at 12+/−1 RPM.

The blend was passed through a Comil rotary mill equipped with a 0.032" screen and a round edge impeller running at approximately 1400 RPM. The blend was collected in a second 10 L bin. The bin contents were blended for 10 minutes at 12+/−1 RPM.

Intragranular magnesium stearate, 6 g, was added to the bin and blended for 3 minutes at 12+/−1 RPM. The lubricated blend was processed through a Gerteis roller compactor equipped with knurled rollers, side rims, and an inline oscillating mill containing a pocket rotor and a 1-mm rasping plate. The target ribbon solid fraction was 0.7 (0.67-0.73) and granules were collected in the initial 10 L bin.

Extragranular magnesium stearate, 18 g, was added to the bin and contents were blended for 3 minutes at 12+/−1 RPM. Final blend was affixed above a Kilian T-100 rotary tablet press. Tablets were compressed using $^{13}/_{32}$" SRC tooling, to an average target weight of 500 mg+/−5% and a target hardness of 15 kP. Tablets were passed through a deduster and a metal detector.

TABLE 11

22 mg Tofacitinib hydrophilic matrix tablet composition; Total tablet weight 500 mg

| Ingredient | Function | % Composition | Grams |
|---|---|---|---|
| Tofacitinib Citrate | Active ingredient | 7.1% | 171.15 |
| Methocel K100LV CR Premium Grade | Polymer, gel former providing controlled release | 30% | 720.00 |
| Lactose Monohydrate, Fast Flo 316 | Filler | 61.9% | 1484.85 |

TABLE 11-continued 22 mg Tofacitinib hydrophilic matrix tablet composition; Total tablet weight 500 mg

| Ingredient | Function | % Composition | Grams |
|---|---|---|---|
| Magnesium stearate, vegetable grade (IG) | Lubricant | 0.25% | 6.00 |
| Magnesium stearate, vegetable grade (EG) | Lubricant | 0.75% | 18.00 |
| Total | | 100% | 2400.00 |

The compressed tablets provide the following release in pH 6.8 media, paddles at 50 rpm based on Dissolution test 1 (Table 12).

TABLE 12

| Time (hr) | % Drug Dissolved |
|---|---|
| 1 | 24 |
| 2.5 | 47 |
| 5 | 76 |

Example 5. 20 mg Bilayer Osmotic Tablet

The batch quantities of Tofacitinib and Polyethylene Oxide N80 (see also Table 13) were passed through a 30 mesh screen and added to a 500 cc amber bottle. The blend was mixed for 10 minutes with a Turbula bottle blender. 0.2 grams of magnesium stearate was passed through a 30 mesh screen and added to the bottle of active blend and mixed for 3 minutes.

The batch quantities of polyethylene oxide (coagulant grade), blue lake dye, and sodium chloride were passed through a 20 or 30 mesh screen and added in that order to a 500 cc bottle. The blend was mixed for 10 minutes with a Turbula bottle blender. 0.5 grams of magnesium stearate was passed through a 30 mesh screen and added to the bottle of sweller layer and mixed for 3 minutes.

Tablets were compressed using 9-mm standard round convex tooling, to an average target weight of 400 mg+/−5%, average target thickness of 7 mm+/−0.05 mm, and a target hardness of 15 kP.

TABLE 13

| | Grade: | Quantity (mg)/unit: | % | Batch Quantity (grams) |
|---|---|---|---|---|
| Active Layer Components: | | | | |
| Tofacitinib Citrate | | 33.333 | 12.5% | 5.0 |
| Polyethylene Oxide WSR N80 Grade | NF | 232 | 87.0% | 34.8 |
| Magnesium Stearate[e] | NF/EP | 1.333 | 0.5% | 0.2 |
| | | 266.667 | 100.0% | 40 |
| Sweller Layer Components: | | | | |
| Polyethylene Oxide Coagulant Grade[a] | NF | 86 | 64.5% | 64.5 |

TABLE 13-continued

| | Grade: | Quantity (mg)/unit: | % | Batch Quantity (grams) |
|---|---|---|---|---|
| Sodium Chloride[b] | USP/EP | 46.4 | 34.8% | 34.8 |
| FD&C Blue No2 Lake Dye[d] | Food | 0.267 | 0.2% | 0.2 |
| Magnesium Stearate[e] | NF/EP | 0.667 | 0.5% | 0.5 |
| | | 133.333 | 100.0% | 100.0 |

The coating solution was prepared according to the following steps (see also Table 14 below): First, the entire 194.6 grams of water and 800 grams of acetone were added to a 5-Liter vessel and mixed for 5 minutes. 24 grams of hydroxypropyl cellulose were added to the mixture and mixed for 5 minutes. 36 grams of cellulose acetate were added to the mixture and mixed for 5 minutes. The remaining 946.3 grams of acetone were added to the mixture and mixed for 3 hours. This procedure created a 3% solids (w/w) solution.

TABLE 14

| Composition of coated tablet | % in coating | mg/tablet 6% wt gain | coat w/w (%) | Batch Quantity (grams) |
|---|---|---|---|---|
| 1. Tofacitinib Citrate Bilayer Core Tablet Core | — | 400 | — | — |
| 2. Cellulose Acetate (Type 398-10) | 1.8% | 14.4 | 3.6% | 36.0 |
| 3. Hydroxypropyl Cellulose (Klucel EF) | 1.2% | 9.6 | 2.4% | 24.0 |
| 4. Acetone | 87.3% | (698.4) | — | 1746.3 |
| 5. Purified water | 9.7% | (77.6) | — | 194.6 |
| Total Weight | 100% | 424 | 6% | 2000.9 |

250 grams of the 400 mg weight SRC tablets were coated in a Vector LDCS-5 with a 0.5-Liter semi-perforated pan operating at 30 rpm and an airflow of 30 CFM having an exhaust temperature of 40 deg C. The 3% solids (w/w) solution was applied until the wet weight gain reached a level of 6.2%. The tablets were then removed from coating pan and dried at 40 C for 16 hours.

A single hole (1000 micron) was drilled in the end of the band of the oval tablet. The hole can be drilled either by mechanical means or via laser ablation. The target coating of 6% provided the following release in pH 6.8 media, paddles at 50 rpm based on Dissolution test 1 (Table 15):

TABLE 15

| Time (hr) | 6% Weight Gain (% Drug Dissolved) |
|---|---|
| 1 | 6 |
| 2.5 | 42 |
| 5 | 95 |

Example 6. 11 mg Bilayer Osmotic Tablet

The batch quantity of Polyethylene Oxide N80 (active layer) (see also Table 16) was passed through a 30 mesh screen. The large particles that remained on the screen were discarded. Polyethylene Oxide was added to a 500 cc amber bottle and hand blended to coat the inside of the bottle. The batch quantity of Tofacitinib was added and mixed for 10 minutes with a Turbula bottle blender. 1.0 gram of magnesium stearate was added to the bottle of active blend and mixed for 3 minutes.

The batch quantity of Polyethylene oxide Coagulant grade (sweller layer) and sodium chloride were passed through 30 mesh screen. Polyethylene oxide, the batch quantity of microcrystalline cellulose, the batch quantity of blue lake dye and sodium chloride powder were added in that order to a 950 cc bottle. The blend was mixed for 10 minutes with a Turbula bottle blender. 1.0 gram of magnesium stearate was added to the bottle of sweller layer and mixed for 3 minutes.

Bilayer tablets are compressed using 9/32 inch standard round convex tooling, to an average target weight of 180.0 mg+/−5% and an average target thickness of 5.0 mm+/−0.1 mm.

TABLE 16

| | Grade: | Quantity (mg)/unit: | % | Batch Quantity (grams) |
|---|---|---|---|---|
| Active Layer Components: | | | | |
| Tofacitinib Citrate | | 17.76 | 14.80 | 14.80 |
| Polyethylene Oxide WSR N80 Grade[a] | NF | 101.04 | 84.20 | 84.20 |
| Magnesium Stearate[e] | NF/EP | 1.20 | 1.00 | 1.00 |
| | | 120.00 | 100.00 | 100.00 |
| Sweller Layer Components: | | | | |
| Polyethylene Oxide Coagulant Grade[a] | NF | 32.52 | 54.20 | 108.40 |
| Microcrystalline Cellulose | PhEur/NF | 12.00 | 20.00 | 40.00 |
| Sodium Chloride[b] | USP/EP | 15.00 | 25.00 | 50.00 |
| FD&C Blue No2 Lake Dye[d] | Food | 0.18 | 0.30 | 0.60 |
| Magnesium Stearate[e] | NF/EP | 0.30 | 0.50 | 1.00 |
| | | 60.00 | 100.0% | 200.00 |

The coating solution was prepared according to the following steps (see also Table 17): First, 180.0 grams of water was added to 48.6 grams of PEG 3350 in 4 L mixing vessel and mixed or swirled by hand until the PEG was entirely dissolved. Secondly, 131.4 g of cellulose acetate was added to the 4 L mixing vessel containing the PEG-water solution. The CA was disbursed as a slurry or wet cake. While using the 4 L mixing vessel equipped with a rotating impeller, 2,640.0 grams of acetone was added to the PEG-water-CA mixture. The contents of the mixing vessel were agitated until all solids were dissolved.

TABLE 17

| # | Material | Composition (%) | Grams |
|---|---|---|---|
| 1 | Cellulose Acetate | 4.38% | 131.4 |
| 2 | Polyethylene Glycol 3350 with 100 ppm BHT (PEG 3350) | 1.62% | 48.6 |
| 3 | Acetone [(1)] | 88.00% | 2640.0 |
| 4 | Purified Water [(1)] | 6.00% | 180.0 |
| | Total | 100.00% | 3000.0 |

TABLE 17-continued

| Component | Coating Solution % Wt | mg/tablet |
|---|---|---|
| Tofacitinib Citrate Bilayer Core Tablet Core | — | 180.00 |
| Coating Composition | | |
| Cellulose Acetate | 4.38% | 17.08 |
| Polyethylene Glycol 3350 with 100 ppm BHT (PEG 3350) | 1.62% | 6.32 |
| Acetone [1] | 88.00% | 343.20 |
| Purified Water [1] | 6.00% | 23.40 |
| Total | 100.00% | 203.40 |

[1] Included for Coating Compositional Purposes, Not Present in Final Dosage Form 250 grams of the 180 mg bilayer tablet cores were coated in a Vector LDCS-5 with a 0.5 liter fully perforated coating pan operating at 30 rpm and an airflow of 35 CFM having an exhaust temperature of 32 deg C. The 6% solids (w/w) solution was applied until an in-process coating weight gain of 25.2 mg per tablets was achieved. The tablets were then removed from coating pan and dried at 40 C for 16 hours.

A single delivery port with a diameter of 1.0 mm was formed through the coating membrane centered on the face of the drug layer side of the bilayer tablet. The delivery port can be formed either by mechanical means or via laser ablation. The target coating level of 23.4 mg or 13% of the target bilayer core weight provided a controlled release drug delivery exhibiting 80% of the drug delivered at 3.5 hours in pH 6.8 media, paddles at 50 rpm based on Dissolution test 1. Additional dissolution data is given in Table 18.

TABLE 18

| Time (hours) | % Release |
|---|---|
| 1.0 | 13 |
| 2.5 | 55 |
| 5.0 | 96 |

Example 7. 11 mgA Bilayer Osmotic Tablet with Antioxidants

The formulation of Example 7 was made as follows (see also Table 19): Polyethylene oxide N80 was passed through a 30 mesh screen. The large particles of polyethylene oxide N80 that remain on the screen were discarded. Separately, the primary particle size of the sodium metabisulfite and butylated hydroxyanisole was reduced using a mortar and pestle. One-fourth the batch amount of polyethylene oxide was combined with the batch amounts of sodium metabisulfite and butylated hydroxyanisole and added to a 950 cc amber glass bottle and mixed for 5 minutes in a Turbula bottle blender. The remaining polyethylene oxide N80 and batch amount of tofacitinib citrate was added to the 950 cc amber glass bottle and mixed in a Turbula bottle blender for 10 minutes. The blend was passed through a mini Co-mil using a 0.8 mm screen size to enhance mixing and distribution of components. The blend was then mixed for an additional 10 minutes in a Turbula bottle blender. The batch amount of magnesium stearate was then added to the previous mixture in the 950 cc amber glass bottle and was mixed for 3 minutes in a Turbula bottle blender.

Polyethylene oxide Coagulant grade and sodium chloride were passed through 30 mesh screen and the large particles that remained on the screen were discarded. Separately, the primary particle size of the sodium metabisulfite and butylated hydroxyanisole was reduced using a mortar and pestle. One-half the batch amount of polyethylene oxide was combined with the batch amounts of sodium metabisulfite and butylated hydroxyanisole and added to a 950 cc amber glass bottle and mixed for 5 minutes in a Turbula bottle blender. The remaining amount of polyethylene oxide Coagulant grade, microcrystalline cellulose, blue lake dye and sodium chloride powder were added in that order to a 950 cc amber glass bottle and mixed for 10 minutes with a Turbula bottle blender. The blend was passed through a mini Co-mil using a 0.8 mm screen size to enhance mixing and distribution of components. 1.0 gram of magnesium stearate was added to the bottle and mixed for 3 minutes.

Bilayer tablets were compressed using 9/32 inch standard round convex tooling, to an average target weight of 180.0 mg+/−5% and an average target thickness of 5.0 mm+/−0.1 mm.

TABLE 19

| | % Weight | Unit Quantity (mg/tablet) | Batch Quantity (grams) |
|---|---|---|---|
| Active Layer Components | | | |
| Tofacitinib Citrate | 14.80 | 17.76 | 29.61 |
| Polyethylene Oxide (Polyox WSR N80) | 79.30 | 95.16 | 158.59 |
| Sodium Metabisulfite | 4.67 | 5.60 | 9.33 |
| Butylated Hydroxyanisole | 0.23 | 0.28 | 0.47 |
| Magnesium Stearate | 1.00 | 1.20 | 2.00 |
| Total | 100.00 | 120.00 | 200.00 |
| Sweller Layer Components: | | | |
| Polyethylene Oxide (Polyox WSR Coagulant) | 51.67 | 31.00 | 103.33 |
| Microcrystalline Cellulose | 20.00 | 12.00 | 40.00 |
| Sodium Chloride | 25.00 | 15.00 | 50.00 |
| Sodium Metabisulfite | 2.41 | 1.45 | 4.82 |
| Butylated Hydroxyanisole | 0.12 | 0.07 | 0.24 |
| FD&C Blue No2 Lake | 0.30 | 0.18 | 0.60 |
| Magnesium Stearate | 0.50 | 0.30 | 1.00 |
| Total | 100.00 | 60.00 | 200.00 |

The coating solution was prepared according to the following steps (see also Table 20): First, 150.0 grams of water was added to 40.5 grams of PEG 3350 in 4 L mixing vessel and mixed or swirled by hand until the PEG was entirely dissolved. Secondly, 109.5 g of cellulose acetate was added to the 4 L mixing vessel containing the PEG-water solution. The CA was disbursed as a slurry or wet cake. While using the 4 L mixing vessel equipped with a rotating impeller, 2198.1 grams of acetone was added to the PEG-water-CA mixture. The contents of the mixing vessel were agitated until all solids are dissolved.

TABLE 20

| # | Material | Composition (%) | Grams |
|---|---|---|---|
| 1 | Cellulose Acetate | 4.38% | 109.5 |
| 2 | Polyethylene Glycol 3350 with 100 ppm BHT (PEG 3350) | 1.62% | 40.50 |
| 3 | Sodium Metabisulfite | 0.064% | 1.60 |
| 4 | Butylated Hydroxyanisole | 0.012% | 0.31 |

TABLE 20-continued

| # | Material | Composition (%) | Grams |
|---|---|---|---|
| 5 | Acetone [1] | 87.92% | 2198.1 |
| 6 | Purified Water [1] | 6.00% | 150.0 |
| | Total | 100.00% | 2500.0 |

250 grams of the tofacitinib bilayer tablet cores were coated in a Vector LDCS-5 with a 0.5 liter fully perforated coating pan operating at 30 rpm and an airflow of 35 CFM having an exhaust temperature of 32 deg C. The 6% solids (w/w) solution was applied until an in-process coating weight gain of 25.2 mg per tablets was achieved. The tablets were then removed from coating pan and dried at 40 C for 16 hours.

A single delivery port with a diameter of 1.0 mm was formed through the coating membrane centered on the face of the drug layer side of the bilayer tablet. The delivery port was formed either by mechanical means or via laser ablation. The target coating level of 23.7 mg or 13% of the target bilayer core weight provides a controlled release drug delivery corresponding to 80% of the drug delivered at 2.8 hours in pH 6.8 media, paddles at 50 rpm based on Dissolution test 1. Additional dissolution data is given in Table 21.

TABLE 21

| Time (hours) | % Release |
|---|---|
| 1.0 | 17 |
| 2.5 | 73 |
| 5.0 | 98 |

Example 8. 22 mg Bilayer Osmotic Tablet

The formulation of Example 8 was made as follows (see also Table 22): The batch quantity of Polyethylene Oxide N80 was passed through a 30 mesh screen. The large particles that remained on the screen were discarded. Polyethylene Oxide N80 was added to a 500 cc amber bottle and hand blended to coat the inside of the bottle. The batch quantity of Tofacitinib was added and mixed for 10 minutes with a Turbula bottle blender. 1.0 gram of magnesium stearate was added to the bottle of active blend and mixed for 3 minutes.

The batch quantity of Polyethylene oxide Coagulant grade and sodium chloride were passed through 30 mesh screen. Polyethylene oxide, the batch quantity of microcrystalline cellulose, the batch quantity of blue lake dye and sodium chloride powder were added in that order to a 950 cc bottle. The blend was mixed for 10 minutes with a Turbula bottle blender. 1.0 gram of magnesium stearate was added to the bottle of sweller layer and mixed for 3 minutes.

Tablets were compressed using 5/16 inch standard round convex tooling, to an average target weight of 250.0 mg+/−5% and an average target thickness of 5.6 mm+/−0.1 mm.

TABLE 22

| | Grade: | Quantity (mg)/unit: | % | Batch Quantity (grams) |
|---|---|---|---|---|
| Active Layer Components: | | | | |
| Tofacitinib Citrate | | 35.53 | 21.28% | 21.28 |
| Polyethylene Oxide WSR N80 Grade[a] | NF | 129.80 | 77.72% | 77.72 |
| Magnesium Stearate[e] | NF/EP | 1.67 | 1.0% | 1.00 |
| | | 167.00 | 100.0% | 100.00 |
| Sweller Layer Components: | | | | |
| Polyethylene Oxide Coagulant Grade[a] | NF | 44.99 | 54.20 | 108.40 |
| Microcrystalline Cellulose | PhEur/NF | 16.60 | 20.00 | 40.00 |
| Sodium Chloride[b] | USP/EP | 20.75 | 25.00 | 50.00 |
| FD&C Blue No2 Lake Dye[d] | Food | 0.25 | 0.30 | 0.60 |
| Magnesium Stearate[e] | NF/EP | 0.42 | 0.50 | 1.00 |
| | | 83.00 | 100.0% | 200.00 |

The coating solution was prepared according to the following steps (see also Table 23): First, 180.0 grams of water was added to 48.6 grams of PEG 3350 in 4 L mixing vessel and mixed or swirled by hand until the PEG was entirely dissolved. Secondly, 131.4 g of cellulose acetate was added to the 4 L mixing vessel containing the PEG-water solution. The CA was dispersed as a slurry or wet cake. While using the 4 L mixing vessel equipped with a rotating impeller, 2,640.0 grams of acetone was added to the PEG-water-CA mixture. The contents of the mixing vessel were agitated until all solids were dissolved.

TABLE 23

| # | Material | Composition (%) | Grams |
|---|---|---|---|
| 1 | Cellulose Acetate | 4.38% | 131.4 |
| 2 | Polyethylene Glycol 3350 with 100 ppm BHT (PEG 3350) | 1.62% | 48.6 |
| 3 | Acetone | 88.00% | 2640.0 |
| 4 | Purified Water | 6.00% | 180.0 |
| | Total | 100.00% | 3000.0 |

| Component | Coating Solution % Wt | mg/tablet |
|---|---|---|
| Tofacitinib Citrate Bilayer Core Tablet Core | — | 250.00 |
| Cellulose Acetate | 4.38% | 20.08 |
| Polyethylene Glycol 3350 with 100 ppm BHT (PEG 3350) | 1.62% | 7.43 |
| Acetone [1] | 88.00% | 403.33 |
| Purified Water [1] | 6.00% | 27.5 |
| Total | 100.00% | 277.50 |

[1] Included for Coating Compositional Purposes, Not Present in Final Dosage Form 250 grams of the bilayer tablet cores were coated in a Vector LDCS-5 with a 0.5-Liter fully perforated coating pan or drum operating at 30 rpm and an airflow of 35 CFM having an exhaust temperature of 32 deg C. The 6% solids (w/w) solution was applied until an in-process coating weight gain of 30.0 mg per tablets was achieved. The tablets were then removed from coating pan and dried at 40 C for 16 hours.

A single delivery port with a diameter of 1.0 mm was formed through the coating membrane centered on the face of the drug layer side of the bilayer tablet. The delivery port can be formed either by mechanical means or via laser ablation. The target coating level of 27.5 mg or 11% of the target bilayer core weight provided a controlled release drug delivery exhibiting 80% of the drug delivered at 3.7 hours in pH 6.8 media, paddles at 50 rpm based on Dissolution test 1. Additional dissolution data is given in Table 24.

TABLE 24

| Time (hours) | % Release |
| --- | --- |
| 1.0 | 11 |
| 2.5 | 53 |
| 5.0 | 90 |

Example 9. 20 mg AMT Formulation

Formulate Example 9—as follows (see also Table 25). Pass the batch quantities of Tofacitinib, Mannitol, Microcrystalline Cellulose, and Dibasic Calcium Phosphate through a 30 mesh screen and add to a 500 cc amber bottle. Mix the blend for 10 minutes with a Turbula bottle blender. Pass 0.3 grams of magnesium stearate through a 30 mesh screen and add to the bottle of active blend and mix for 3 minutes.

Compress the blend into compacts having a solid fraction of ~0.70. Mill the compacts to form a granulation. Pass 0.2 grams of magnesium stearate through a 30 mesh screen and add to the bottle of active granulation and mix for 3 minutes.

Compress tablets using 9-mm standard round convex tooling, to an average target weight of 400 mg+/−5%, average target thickness of 7 mm+/−0.05 mm, and a target hardness of 15 kP.

TABLE 25

| Sweller Layer Components: | Grade: | Quantity (mg)/unit: | % | Batch Quantity (grams) |
| --- | --- | --- | --- | --- |
| Tofacitinib Citrate |  | 33.33 | 8.33% | 3.33 |
| Mannitol 2080 | NF/EP | 140.00 | 35% | 14 |
| Microcrystalline Cellulose | NF/EP | 60.00 | 15% | 6 |
| Dibasic Calcium Phosphate | NF/EP | 161.67 | 40.42% | 16.17 |
| Magnesium Stearate[e] | NF/EP | 3.00 | 0.75% | 0.3 |
| Magnesium Stearate[e] | NF/EP | 2.00 | 0.50% | 0.2 |
|  |  | 400.00 | 100.0% | 40 |

Prepare the coating solution according to the following steps (see also Table 26): First, add 115 grams of water and 150 grams of acetone to a 2-Liter vessel and mix for 5 minutes. Add 12 grams of hydroxypropyl cellulose to the mixture and mix for 5 minutes. Add 28 grams of cellulose acetate to the mixture and mix for 5 minutes. Add the remaining 195 grams of cellulose acetate to the mixture and mixed for 3 hours. This procedure creates a 8% solids (w/w) solution.

TABLE 26

| Composition of duration 1 coated tablet | % in coating | mg/tablet 7.5% wt gain |
| --- | --- | --- |
| 1. Tofacitinib Citrate Tablet Core | — | 400 |
| 2. Cellulose Acetate (Type 398-10) | 5.6% | 21.0 |
| 3. Hydroxypropyl Cellulose (Klucel EF) | 2.4% | 9.0 |
| 4. Acetone | 69.0% | (258.8) |
| 5. Purified water | 23.0% | (86.2) |
| Total Weight | 100% | 430 |

Coat 250 grams of the 400 mg weight SRC tablets in a Vector LDCS-5 with a 0.5-Liter semi-perforated pan operating at 30 rpm and an airflow of 30 CFM having an exhaust temperature of 40 deg C. Spray the 8% solids (w/w) solution until the wet weight gain reached a level of 7.5%. Remove the tablets from the coating pan and dry at 40 C for 16 hours.

Example 10. 20 mg Bilayer Osmotic Capsule

Pre-Mix 98.94 grams of polyethylene oxide (Polyox WSR N80 LEO) and 1.06 grams of magnesium stearate were passed through a 30-mesh sieve and added to a 250 ml amber bottle. The blend was mixed using a Turbula mixer (Model T2F) operating at 49 cycles/min for 2 minutes.

Active Layer—600 mg Weight 283.71 mg of the Pre-mix was added to a 1 dram glass vial and shaken by hand to pre-coat the inside of the glass vial. 32.57 mg of tofacitinib citrate was passed through a 20 or 30 mesh sieve and added to the 1 dram glass vial. An additional 283.71 mg of the Pre-mix was then added to the 1 dram glass vial. The contents of the glass vial were then blended using a Turbula mixer (Model T2F) operating at 49 cycles/min for 5 minutes. The blend was then transferred to a Natoli single-station hydraulic tablet press and compressed to a target thickness of 15.6 mm using 5.500" B-type 0.3051" Modified Ball Upper Punch and a 4.755" B-type 0.3051" Flat Face Bevel Edge Lower Punch.

Sweller Layer—300 mg Weight

The sweller layer for the formulation of Example 10 was made as follows (see also Table 27): The batch quantities of polyethylene oxide Coagulant grade, blue lake dye, sodium chloride and microcrystalline cellulose were passed through a 20 or 30 mesh screen added in that order to a 10-Liter Bin blender. The contents of the blender were mixed for 10 minutes of 12 rpm. The blend was then passed blend through a Comil 197S with a round impeller and 0.055" round screen operating at 1000 rpm. The batch quantity of magnesium stearate was added to the middle of the de-lumped blend in the bin blender. The contents of the blender were mixed for 5 minutes of 12 rpm. The blend was then transferred to a Kilian T-100 rotary tablet press and compressed to a target weight of 300 mg and a target thickness of 6.65 mm using 5.500" B-type 0.3051" Modified Ball Upper Punch and a 4.755" B-type 0.3051" Flat Face Bevel Edge Lower Punch.

TABLE 27

| Component: | Grade: | Quantity (mg)/unit | % | Batch Quantity (grams) |
| --- | --- | --- | --- | --- |
| Polyethylene Oxide Coagulant Grade[a] | NF | 154.50 | 51.5% | 2060.00 |
| Sodium Chloride[b] | USP/EP | 104.40 | 34.8% | 1392.00 |
| Microcrystalline Cellulose[c] | NF/EP | 39.00 | 13.0% | 520.00 |

TABLE 27-continued

| Component: | Grade: | Quantity (mg)/unit | % | Batch Quantity (grams) |
|---|---|---|---|---|
| FD&C Blue No2 Lake Dye[d] | Food | 0.60 | 0.2% | 8.00 |
| Magnesium Stearate[e] | NF/EP | 1.50 | 0.5% | 20.00 |
| | | 300.00 | 100.0% | 4000.00 |

Capsule Shell 2.5 kg of pre-coating solution was prepared by combining 25 grams of polysorbate 80 with 2475 grams of acetone and mixing for 10 minutes or until dissolved to yield a 1% (w/w) solution.

15 kg of functional coating solution was prepared according to the following steps (see also Table 28): First, the entire 375 grams of water and 120 grams of PEG 3350 were added to a suitable vessel and mixed. 14,325 grams of acetone were added to the mixture and mixed. 180 grams of cellulose acetate were added to the mixture and mixed until a uniform solution was obtained. This procedure created a 2% solids (w/w) solution.

TABLE 28

| Composition of capsule shells | % in coating | mg in cap | mg in body | Batch Quantity (grams) |
|---|---|---|---|---|
| 1. Cellulose Acetate (Type 398-10) | 1.2% | 58.5 | 55.5 | 180 |
| 2. Polyethylene Glycol 3350 | 0.8% | 39.0 | 37.0 | 120 |
| 3. Acetone | 95.5% | (4655.6) | (4416.9) | (14,325) |
| 4. Purified water | 2.5% | (121.9) | (115.6) | (375) |
| Total Weight | 100% | 97.5 | 92.5 | 15,000 |

1 kg of HDPE capsule molds (either caps or bodies) were coated in a Vector LDCS-5 with a 1.5-Liter semi-perforated pan operating at 18 rpm and an airflow of 40 CFM having an exhaust temperature of 40 deg C. After briefly coating the molds with the 1% w/w pre-coating solution, the functional 2% solids (w/w) coating solution was sprayed at a rate of 20 grams/min with atomizing air pressure of 10 psi and a gun-to-bed distance of 3 inches until the wet weight gain reached a level of 12.5%. The capsule molds were then removed from coating pan and dried at 40 C for 24 hours. The capsule shells were then removed from the molds and trimmed.

A single hole (2000 microns) was drilled in the end of the capsule bodies. The hole can be drilled either by mechanical means or via laser ablation Assembly The Active Layer was inserted into the half of the capsule shell with the pre-drilled hole. The Sweller Layer was inserted into the same half of the capsule shell, flat side first, to be flush against the active layer. These components were inserted into the other half of the capsule shell to close the capsule. When prepared and combined in this manner, these components provided the following release in pH 6.8 media, paddles at 50 rpm based on Dissolution test 1 (Table 29)

TABLE 29

| Time (hr) | % Drug Dissolved |
|---|---|
| 1 | 4 |
| 2.5 | 25 |
| 5 | 65 |

80% of tofacitinib was dissolved in about 6 hours in Dissolution test 1.

Example 11. 20 mg Bilayer Osmotic Capsule

Pre-Mix 98.94 grams of polyethylene oxide (Polyox WSR N80 LEO) and 1.06 grams of magnesium stearate were passed through a 30-mesh sieve and added to a 250 ml amber bottle. The blend was mixed using a Turbula mixer (Model T2F) operating at 49 cycles/min for 2 minutes.

Active Layer—600 mg Weight 283.71 mg of the Pre-mix was added to a 1 dram glass vial and shaken by hand to pre-coat the inside of the glass vial. 32.57 mg of tofacitinib citrate was passed through a 20 or 30 mesh sieve and added to the 1 dram glass vial. 283.71 mg of the Pre-mix was then added to the 1 dram glass vial. The contents of the glass vial were then blended using a Turbula mixer (Model T2F) operating at 49 cycles/min for 5 minutes. The blend was then transferred to a Natoli single-station hydraulic tablet press and compressed to a target thickness of 15.6 mm using a 5.500" B-type 0.3051" Modified Ball Upper Punch and a 4.755" B-type 0.3051" Flat Face Bevel Edge Lower Punch.

Sweller Layer

The sweller layer for the formulation of Example 11 was made as follows (see also Table 30). The batch quantities of polyethylene oxide Coagulant grade, blue lake dye, sodium chloride and microcrystalline cellulose were passed through a 20 or 30 mesh screen added in that order to a 10-Liter Bin blender. The contents of the blender were mixed for 10 minutes of 12 rpm. The blend was then passed blend through a Comil 197S with a round impeller and 0.055" round screen operating at 1000 rpm. The batch quantity of magnesium stearate was added to the middle of the de-lumped blend in the bin blender. The contents of the blender were mixed for 5 minutes of 12 rpm. The blend was then transferred to a Kilian T-100 rotary tablet press and compressed to a target weight of 300 mg and a target thickness of 6.65 mm using 5.500" B-type 0.3051" Modified Ball Upper Punch and a 4.755" B-type 0.3051" Flat Face Bevel Edge Lower Punch.

TABLE 30

| Component: | Grade: | Quantity (mg)/unit: | % | Batch Quantity (grams) |
|---|---|---|---|---|
| Polyethylene Oxide Coagulant Grade[a] | NF | 154.50 | 51.5% | 2060.00 |
| Sodium Chloride[b] | USP/EP | 104.40 | 34.8% | 1392.00 |
| Microcrystalline Cellulose[c] | NF/EP | 39.00 | 13.0% | 520.00 |
| FD&C Blue No2 Lake Dye[d] | Food | 0.60 | 0.2% | 8.00 |
| Magnesium Stearate[e] | NF/EP | 1.50 | 0.5% | 20.00 |
| | | 300.00 | 100.0% | 4000.00 |

Capsule Shell 2.5 kg of pre-coating solution was prepared by combining 25 grams of polysorbate 80 with 2475 grams of acetone and mixing for 10 minutes or until dissolved to yield a 1% (w/w) solution.

15 kg of functional coating solution was prepared according to the following steps (see also Table 31): First, the 375 grams of water and 61.5 grams of PEG 3350 were added to a suitable vessel and mixed. 14,325 grams of acetone were added to the mixture and mixed. 225 grams of cellulose acetate were added to the mixture and mixed. 13.5 Grams of TEC were added to the mixture and mixed until a uniform solution was obtained. This procedure creates a 2% solids (w/w) solution.

TABLE 31

| Composition of capsule shells | % in coating | mg in cap | mg in body | Batch Quantity (grams) |
|---|---|---|---|---|
| 1. Cellulose Acetate (Type 398-10) | 1.50% | 73.1 | 69.38 | 225 |
| 2. Polyethylene Glycol 3350 | 0.41% | 20.0 | 18.69 | 61.5 |
| 3. Triethyl Citrate (TEC) | 0.09% | 4.4 | 4.16 | 13.5 |
| 4. Acetone | 95.5% | (4655.6) | (4416.9) | (14,325) |
| 5. Purified water | 2.5% | (121.9) | (115.6) | (375) |
| Total Weight | 100% | 97.5 | 92.5 | 15,000 |

1 kg of HDPE capsule molds (either caps or bodies) were coated in a Vector LDCS-5 with a 1.5-Liter semi-perforated pan operating at 18 rpm and an airflow of 40 CFM having an exhaust temperature of 40 deg C. After briefly coating the molds with the 1% w/w pre-coating solution, the functional 2% solids (w/w) coating solution was sprayed at a rate of 20 grams/min with atomizing air pressure of 10 psi and a gun-to-bed distance of 3 inches until the wet weight gain reached a level of 12.5%. The capsule molds were then removed from coating pan and dried at 40 C for 24 hours. The capsule shells were then removed from the molds and trimmed.

A single hole (2000 microns) was drilled in the end of the capsule bodies. The hole can be drilled either by mechanical means or via laser ablation.

Assembly

The Active Layer is inserted into the half of the capsule shell with the pre-drilled hole. The Sweller Layer is inserted into the same half of the capsule shell, flat side first, to be flush against the active layer. These components are inserted into the other half of the capsule shell until the capsule is closed. When prepared and combined in this manner, these components provide the following release in pH 6.8 media, paddles at 50 rpm based on Dissolution test 1 (Table 32).

TABLE 32

| Time (hr) | % Drug Dissolved |
|---|---|
| 1 | 1 |
| 2.5 | 4 |
| 5 | 21 |

80% of tofacitinib is dissolved in about 14 hours in dissolution method 1.

Example 12. Hydrophilic Matrix Controlled Release Tablet

The metal surfaces of a 10 L bin were pre-coated by adding the batch quantity (also see Table 33 below), 963 g of Lactose Fast Flo 316 and blending for 2 minute at 12+/−1 RPM. The batch quantity of Tofacitinib, 164 g was added to the 10 L bin and folded into the lactose monohydrate. The Tofacitinib container was rinsed with some of the lactose monohydrate from the 10 L bin. The batch quantity of Hypromellose, 1150 g, was added to the 10 L bin. All of the components were blended in the bin for 10 minutes at 12+/−1 RPM.

The blend was passed through a Comil rotary mill equipped with a 0.032" screen and a round edge impeller running at approximately 1400 RPM. The blend was collected in a second 10 L bin. The bin contents were blended for 10 minutes at 12+/−1 RPM.

Intragranular magnesium stearate, 5.75 g, was added to the bin and blended for 3 minutes at 12+/−1 RPM. The lubricated blend was processed through a Gerteis roller compactor equipped with knurled rollers, side rims, and an inline oscillating mill containing a pocket rotor and a 1-mm rasping plate. The target ribbon solid fraction is 0.7 (0.67-0.73) and granules were collected in the initial 10 L bin.

Extragranular magnesium stearate, 17.25 g, was added to the bin and contents were blended for 3 minutes at 12+/−1 RPM. Final blend was affixed above a Kilian T-100 rotary tablet press. Tablets were compressed using ¹³⁄₃₂" SRC tooling, to an average target weight of 500 mg+/−5% and a target hardness of 15 kP. Tablets were passed through a deduster and a metal detector.

TABLE 33

22 mg Tofacitinib hydrophilic matrix tablet composition; Total tablet weight 500 mg

| Ingredient | Function | % Composition | Grams |
|---|---|---|---|
| Tofacitinib Citrate | Active ingredient | 7.1% | 164.00 |
| Methocel K100LV CR Premium Grade | Polymer, gel former providing controlled release | 50% | 1150.00 |
| Lactose Monohydrate, Fast Flo 316 | Filler | 41.9% | 963 |
| Magnesium stearate, vegetable grade (IG) | Lubricant | 0.25% | 5.75 |
| Magnesium stearate, vegetable grade (EG) | Lubricant | 0.75% | 17.25 |
| Total | | 100% | 2300.00 |

The compressed tablets provide the following release in pH 6.8 media, paddles at 50 rpm based on Dissolution test 1 (Table 34).

TABLE 34

| Time (hr) | % Drug Dissolved |
|---|---|
| 1 | 16 |
| 2.5 | 32 |
| 5 | 54 |

Example 13. 10 mg Immediate Release Tablet

TABLE 35

Composition of the formulation of Example 13

| Component Name | Grade | Unit Composition (mg) |
|---|---|---|
| 1. Tofacitinib Citrate | Pharm | 16.155 |
| 2. Microcrystalline Cellulose | Ph. Eur/NF | 245.23 |

TABLE 35-continued

Composition of the formulation of Example 13

| Component Name | Grade | Unit Composition (mg) |
|---|---|---|
| 3. Lactose Monohydrate | Ph. Eur/NF | 122.615 |
| 4. Croscarmellose Sodium | Ph. Eur/NF | 12.000 |
| 5. Magnesium Stearate | Ph. Eur/NF | 1.000 |
| 6. Magnesium Stearate | Ph. Eur/NF | 3.000 |
| TABLET CORE WEIGHT: | | 400.000 |
| 7. Opadry II White (HPMC based) | Pharm | 12.000 |
| 8. Purified Water | Ph. Eur/USP | (68.000) |
| Total: | | 412.000 mg |

The tablet formulation of Example 13 is manufactured according to the following process. Components 1-4 are combined and processed using a blend-mill-blend procedure. Component 5 is then added to the blend contents and combined using a blending procedure. This lubricated blend is than dry granulated. Component 6 is then added to the dry granulation and combined using a blending procedure. The lubricated granulation is compressed into 400 mg weight tablets using a rotary tablet press. The tablets are then coated using a film coater which sprays a solution containing Components 7 and 8 until 12 mg of coating has been applied to the tablets.

Example 14. 5 mg Immediate Release Tablet

TABLE 36

Composition of the formulation of Example 14

| Component Name | Grade | Unit Composition (mg) |
|---|---|---|
| 1. Tofacitinib Citrate | Pharm | 8.078 |
| 2. Microcrystalline Cellulose | Ph. Eur/NF | 314.615 |
| 3. Lactose Monohydrate | Ph. Eur/NF | 157.307 |
| 4. Croscarmellose Sodium | Ph. Eur/NF | 15.000 |
| 5. Magnesium Stearate | Ph. Eur/NF | 2.500 |
| 6. Magnesium Stearate | Ph. Eur/NF | 2.500 |
| TABLET CORE WEIGHT: | | 500.000 |
| 7. Opadry II White (HPMC based) | Pharm | 20.000 |
| 8. Purified Water | Ph. Eur/USP | (113.333) |
| Total: | | 520.000 mg |

The tablet is manufactured according to the following process. Components 1-4 are combined and processed using a blend-mill-blend procedure. Component 5 is then added to the blend contents and combined using a blending procedure. This lubricated blend is than dry granulated. Component 6 is then added to the dry granulation and combined using a blending procedure. The lubricated granulation is compressed into 500 mg weight tablets using a rotary tablet press. The tablets are then coated using a film coater which sprays a solution containing Components 7 and 8 until 20 mg of coating has been applied to the tablets.

Example 15. Study A

The relative bioavailability of a single dose of 2 different oral sustained release formulations of 20 mg tofacitinib relative to a single dose of 10 mg tofacitinib immediate release (IR) tablets were performed and the following endpoints for tofacitinib were determined: $C_{max}$, $T_{max}$, $AUC_{inf}$, $AUC_{last}$. An additional endpoint was determined for the relative bioavailability (% RBA) of tofacitinib for each sustained release formulations relative to the IR formulation.

The study was a randomized, open-label, single dose, 3-period, 3-treatment, 6-sequence crossover study in 12 healthy male subjects (See Table 37). Subjects received two different sustained release formulations of tofacitinib and the immediate release tablet formulation with a washout period of 3 days between doses. The sustained release formulations were given as a 20 mg single dose and the immediate release formulation was given as two 5 mg tablets in a single dose.

TABLE 37

| | Period | | |
|---|---|---|---|
| Sequence | 1 | 2 | 3 |
| ABC (n = 2) | A | B | C |
| BCA (n = 2) | B | C | A |
| CAB (n = 2) | C | A | B |
| ACB (n = 2) | D | E | C |
| BAC (n = 2) | E | A | D |
| CBA (n = 2) | A | E | B |

A: Immediate Release Tablet, 10 mg;
B: Example 10 bilayer osmotic capsule, 20 mg;
C: Example 11 bilayer osmotic capsule, 20 mg;

Subjects were fasted overnight for at least 8 hours prior to administration of the study drug. On the morning of Day 1 of each period, all subjects received a single oral dose of study drug with 240 mL of water. Subjects were allowed a standardized lunch 4 hours after dose administration.

Dosage Forms Administered:

Tofacitinib 10 mg Immediate Release Control Tablet (reference): prepared in Example 13.

Tofacitinib 20 mg bilayer osmotic capsule: prepared in Example 10.

Tofacitinib 20 mg bilayer osmotic capsule: prepared in Example 11.

During all study periods, blood samples to provide plasma for pharmacokinetic analysis was collected at periodic time points. PK samples were analyzed using standard validated analytical methods. Dose normalized natural log transformed $AUC_{inf}$, $AUC_{last}$ and $C_{max}$ are analyzed for tofacitinib using a mixed effect model with sequence, period and treatment as fixed effects and subject within sequence as a random effect. Estimates of the adjusted mean differences (Test-Reference) and corresponding 90% confidence intervals were obtained from the model. The adjusted mean differences and 90% confidence intervals for the differences was exponentiated to provide estimates of the ratio of adjusted geometric means (Test/Reference) and 90% confidence intervals for the ratios. The immediate release control tablet formulation was the Reference treatment and the sustained release formulations were the Test treatments.

The relative bioavailability of tofacitinib was estimated as the ratio of dose-normalized adjusted geometric means for Test and Reference for $AUC_{inf}$.

The PK parameters $AUC_{inf}$, $AUC_{last}$, $C_{max}$, $T_{max}$, and $t_{1/2}$ were summarized descriptively by treatment and analyte (when applicable). For $AUC_{inf}$ and $C_{max}$, individual subject parameters were plotted by treatment for each analyte separately (when applicable). Concentrations were listed and summarized descriptively by PK sampling time, treatment and analyte (when applicable). Individual subject, mean and median profiles of the concentration-time data were plotted by treatment and analyte (when applicable). For summary statistics, and mean and median plots by sampling time, the nominal PK sampling time were used, for individual subject plots by time, the actual PK sampling time were used.

Predicted steady-state values were obtained via the superposition method using the software package WinNonLin (Pharsight Corp). Superposition was used on each individual's pharmacokinetic profile to generate the steady-state pharmacokinetic profile of each individual. The definitions and method of determination of PK parameters are given in Table 38. The results of the study are shown in Table 39.

TABLE 38

| Parameter | Definition | Method of Determination |
|---|---|---|
| $AUC_{last}$ | Area under the plasma concentration-time profile from time zero to the time of the last quantifiable concentration ($C_{last}$) | Log-linear trapezoidal method |
| $AUC_{inf}$ | Area under the plasma concentration-time profile from time zero extrapolated to infinite time | $AUC_{last} + (C_{last}*/k_{el})$, where $C_{last}*$ is the predicted plasma concentration at the last quantifiable time point estimated from the log-linear regression analysis. |
| $AUC_{inf, dn}$ | Area under the plasma concentration-time profile from time zero extrapolated to infinite time divided by the dose administered | $AUC_{inf}$/dose |
| $C_{max}$ | Maximum plasma concentration | Observed directly from data |
| $C_{max, dn}$ | Maximum plasma divided by the dose administered concentration | $C_{max}$/dose |
| $T_{max}$ | Time for $C_{max}$ | Observed directly from data as time of first occurrence |
| $t_{1/2}$ | Terminal elimination half-life | $Log_e(2)/k_{el}$, where $k_{el}$ is the terminal phase rate constant calculated by a linear regression of the log-linear concentration-time curve. Only those data points judged to describe the terminal log-linear decline will be used in the regression. |
| $C_{min, ss}$ | Minimum plasma concentration during the course of one, 24 hour interval once steady-state has been achieved | Observed from steady-state pharmacokinetic profile data, which is calculated from single dose data using the superposition method |
| $C_{min, dn, ss}$ | Minimum plasma concentration during the course of one, 24 hour interval once steady-state has been achieved | $C_{min, ss}$/dose |
| $C_{max, ss}$ | Maximum plasma concentration during the course of one, 24 hour interval once steady-state has been achieved | Observed from steady-state pharmacokinetic profile data, which is calculated from single dose data using the superposition method |
| $C_{max, ss}/C_{min, ss}$ | Ratio of maximum and minimum plasma concentrations during the course of one, 24 hour interval once steady-state has been achieved | $C_{max, ss}/C_{min, ss}$ |
| Time above 17 ng/ml | Period of time during the course of one, 24 hour interval of steady-state dosing that the plasma concentration is 17 ng/ml | Observed from steady-state pharmacokinetic profile data, which is calculated from single dose data using the superposition method |
| Drug holiday (Time below 17 ng/ml) | Period of time during the course of one, 24 hour interval of steady-state dosing that the plasma concentration is below 17 ng/ml | Observed from steady-state pharmacokinetic profile data, which is calculated from single dose data using the superposition method |

TABLE 39

| | Single Dose PK Parameters | | |
|---|---|---|---|
| | 10 mg IR Tablet (Reference) | 20 mg Example 10 Osmotic Capsule (Test) | 20 mg Example 11 Osmotic Capsule (Test) |
| $C_{max}$ (ng/ml) | 121.5 (30%) | 41.8 (24%) | 18.2 (16%) |
| $C_{max, dn}$ (ng/ml/mg) | 12.1 (30%) | 2.1 (24%) | 0.9 (16%) |
| $AUC_{inf}$ (ng*hr/ml) | 339.5 (17%) | 543.6 (23%) | 390.2 (38%) |
| $AUC_{inf, dn}$ (ng*hr/ml/mg) | 34.0 (17%) | 27.2 (23%) | 18.8 (38%) |
| $t_{1/2}$ (hr) | 3.35 (13%) | 5.84 (23%) | 6.07 (53%) |
| $T_{max}$ (hr) | 0.5 (0.25-2) | 5 (4-10) | 13 (4-24) |
| Dose Normalized $C_{max}$ Ratio (%) | 100% | 17% (14-20%) | 7.5% (6-9%) |
| Dose Normalized RBA (%) | 100% | 80% (65-99%) | 55% (45-69%) |

The above values are reported as Geometric mean (% coefficient of variation (CV)) for all except: median (range) for Tmax; arithmetic mean (% CV) for t½. The above ratios are presented as geometric mean ratio (90% Confidence Intervals).

| | Predicted Steady-State PK | | | |
|---|---|---|---|---|
| | 10 mg IR BID (Reference) | 20 mg Example 10 Osmotic Capsule QD (Test) | 25 mg Example 10 Osmotic Capsule QD* (Test) | 20 mg Example 11 Osmotic Capsule QD (Test) | 33 mg Example 11 Osmotic Capsule QD* (Test) |
|---|---|---|---|---|---|
| $C_{max, ss}$ (ng/ml) | 125.4 (30%) | 46.0 (24%) | 57.5 (24%) | 23.7 (30%) | 39.1 (30%) |
| $C_{min, ss}$ (ng/ml) | 3.7 (39%) | 6.1 (37%) | 7.7 (37%) | 9.9 (76%) | 16.3 (76%) |
| $C_{min, dn, ss}$ (ng/ml/mg) | 0.19 (39%) | 0.31 (37%) | 0.31 (37%) | 0.50 (76%) | 0.50 (76%) |
| $C_{min, ss}$ Ratio (%) | 100% | 166% (128-215%) | 207% (160-268%) | 267% (123-581%) | 441% (203-958%) |
| $C_{max, ss}/C_{min, ss}$ | 34 | 7.5 | 7.5 | 2.4 | 2.4 |

TABLE 39-continued

| Time above 17 ng/ml (hrs) | 12.6 (2 × 6.3 hrs) | 13.1 | 15.1 | 16.9 | 18.6 |
|---|---|---|---|---|---|
| Drug holiday (Time below 17 ng/ml) (hrs) | 11.4 | 10.9 | 8.9 | 7.1 | 5.4 |

The above parameters are presented as geometric mean (% CV). The above ratios are presented as geometric mean ratio (90% Confidence Intervals).
*necessary dose adjustment to achieve 100% RBA with those durations of modified release The results of this study show that sustained release dosage forms which require 6 hours or longer to release and dissolve 80% of tofacitinib do not meet the desired pharmacokinetic attributes for tofacitinib sustained release dosage forms. Specifically, a sustained release dosage form which requires 6 hours or longer to release and dissolve 80% of tofacitinib, and has the required amount of tofacitinib to provide an equivalent AUC value to the immediate release dosage form, provides a time above 17 ng/ml (the JAK 1/3 receptor $IC_{50}$ value) which is greater than the time above 17 ng/ml for the immediate release dosage form. Further, a sustained release dosage form which requires 14 hours to release and dissolve 80% of tofacitinib has a higher dose-normalized $C_{min,ss}$, a lower dose-normalized AUC, and a low relative bioavailability to the immediate release dosage form, which requires an increase in the drug loading of tofacitinib to have equivalent AUC to the immediate release dosage form. These results support the requirement of a sustained release dosage form of tofacitinib requiring less than 6 hours to release and dissolve 80% of tofacitinib.

Example 16. Study B

The relative bioavailability of 3 different oral sustained release formulations of 22 mg tofacitinib relative to a single dose of 10 mg tofacitinib immediate release (IR) tablets were performed and the following endpoints for tofacitinib were determined: $C_{max}$, $T_{max}$, $AUC_{inf}$, $AUC_{last}$. An additional endpoint was determined for the relative bioavailability (% RBA) of tofacitinib for each sustained release formulations relative to the IR formulation.

The study was a randomized, open-label, single dose, 4-period, 6-treatment, 6-sequence partial crossover study in 30 healthy male subjects (See 40). In the first period, subjects received one of two different sustained release formulations of tofacitinib in the fed state. In the second and third periods, subjects received 2 of three sustained release formulations. In the fourth period, subjects received the immediate release tablet formulation. A washout period of 3 days was used between doses. The three sustained release formulations are given as a 22 mg single dose and the immediate release formulation is given as two 5 mg tablets in a single dose.

TABLE 40

| | Period | | | |
|---|---|---|---|---|
| Sequence | 1 (fed) | 2 (fasted) | 3 (fasted) | 4 (fasted) |
| 1 (n = 5) | A | C | D | F |
| 2 (n = 5) | A | C | E | F |
| 3 (n = 5) | B | D | E | F |
| 4 (n = 5) | B | D | C | F |
| 5 (n = 5) | A | E | C | F |
| 6 (n = 5) | B | E | D | F |

A: 4-hr Extrudable Core System Tablet, 22 mg, fed state;
B: Example 4 Matrix Tablet, 22 mg, fed state;
C: 4-hr Extrudable Core System Tablet, 22 mg, fasted state;
D: Example 4 Matrix Tablet, 22 mg, fasted state;
E: Example 12 Matrix Tablet, 22 mg, fasted state;
F: Immediate Release Tablet, 2 × 5 mg, fasted state;

In Period 1, after an overnight fast of at least 8 hours, subjects were administered the standard high-fat FDA breakfast 30 minutes prior to administration of the study drug. Breakfast was consumed within 30 minutes or less. Subjects received either Treatment A or Treatment B administrations 30 minutes (+/−5 minutes) after the initiation of breakfast. No additional food was allowed for at least 4 hours post-dose. Water was withheld for 1 hour pre-dose and 1 hour after the study drug administration. Dosing in Periods 1, 2, and 3 was followed by a minimum washout of 72 hours. The next period of the study (Periods 2, 3, and 4) started immediately following completion of the 72-hour PK sample procedures on Day 4 of the preceding period (Periods 1, 2, and 3 respectively). In Periods 2, 3, and 4, study drug was administered after an overnight fast of at least 8 hours. Food was only allowed after 4 hours post-dose. Water was withheld for 1 hour pre-dose and 1 hour after study drug administration.

Dosage Forms Administered:
Tofacitinib 5 mg Immediate Release Tablet (reference): prepared in Example 14 above.
Tofacitinib 22 mg Extrudable Core System Tablet: prepared in Example 1 above.
Tofacitinib 22 mg Matrix Tablets: prepared in Example 4 and 12 above.

During all study periods, blood samples to provide plasma for pharmacokinetic analysis was collected at periodic time points. The study results are provided in Table 41. PK samples were analyzed using standard validated analytical methods. Dose normalized natural log transformed $AUC_{inf}$, $AUC_{last}$ and $C_{max}$ was analyzed for tofacitinib using a mixed effect model with sequence, period and treatment as fixed effects and subject within sequence as a random effect. Estimates of the adjusted mean differences (Test-Reference) and corresponding 90% confidence intervals were obtained from the model. The adjusted mean differences and 90% confidence intervals for the differences was exponentiated to provide estimates of the ratio of adjusted geometric means (Test/Reference) and 90% confidence intervals for the ratios. The immediate release control tablet formulation was the Reference treatment and the sustained release formulations were the Test treatments.

The relative bioavailability of tofacitinib was estimated as the ratio of dose-normalized adjusted geometric means for Test and Reference for $AUC_{inf}$.

The PK parameters $AUC_{inf}$, $AUC_{last}$, $C_{max}$, $T_{max}$, and $t_{1/2}$ are summarized descriptively by treatment and analyte (when applicable). For $AUC_{inf}$ and $C_{max}$, individual subject parameters were plotted by treatment for each analyte separately (when applicable). Concentrations are listed and summarized descriptively by PK sampling time, treatment and analyte (when applicable). Individual subject, mean and median profiles of the concentration-time data were plotted by treatment and analyte (when applicable). For summary statistics, and mean and median plots by sampling time, the nominal PK sampling time were used, for individual subject plots by time, the actual PK sampling time were used.

Predicted steady-state values were obtained via the superposition method using the software package WinNonLin (Pharsight Corp). Superposition was used on each individual's pharmacokinetic profile to generate the steady-state pharmacokinetic profile of each individual.

Sustained-release dosage forms containing 22 mg of tofacitinib which release and dissolve 80% of tofacitinib in 4-5 hours provide dose-proportional pharmacokinetic performance and meet the desired pharmacokinetic claims when dosed in the fasted state. Sustained-release dosage forms containing 22 mg of tofacitinib which release and dissolve 80% of tofacitinib by osmotic pressure in 4 hours provide similar pharmacokinetic performance when administered in both the fed and fasted states. Sustained-release dosage forms containing 22 mg of tofacitinib which release and dissolve 80% of tofacitinib by matrix diffusion and erosion in 5 hours do not provide similar $C_{max}$ performance when administered in both the fed and fasted states.

Example 17. Study C

The relative bioavailability of a single dose of an oral sustained release formulation of 11 mg tofacitinib relative to a single dose of 22 mg tofacitinib sustained release tablets

TABLE 41

| | Single dose, Bioavailability Evaluation | | | |
|---|---|---|---|---|
| | 10 mg IR Tablet (Reference) | 22 mg ECS (Test) | 22 mg Matrix (Example 4) (Test) | 22 mg Matrix (Example 12) (Test) |
| $C_{max}$ (ng/ml) | 108 (28%) | 101 (28%) | 89 (29%) | 59 (29%) |
| $C_{max, dn}$ (ng/ml/mg) | 10.8 (28%) | 4.6 (28%) | 4.0 (29%) | 2.7 (29%) |
| $AUC_{inf}$ (ng*hr/ml) | 367 (24%) | 757 (23%) | 781 (27%) | 702 (23%) |
| $AUC_{inf, dn}$ (ng*hr/ml/mg) | 36.7 (24%) | 34.4 (23%) | 35.5 (27%) | 31.9 (23%) |
| $T_{max}$ (hr) | 0.5 (0.5-4.0) | 4.0 (2.0-6.0) | 2.5 (1.0-6.0) | 3.0 (2.0-4.0) |
| t½ (hr) | 3.7 (13%) | 5.6 (60%) | 5.3 (51%) | 6.0 (46%) |
| $C_{max}$ Ratio (%) | 100% | 92% (82%-104%) | 84% (75%-94%) | 56% (50%-62%) |
| Dose Normalized RBA (%) | 100% | 91% (87%-96%) | 97% (92%-101%) | 89% (85%-94%) |

The above values are reported as Geometric mean (% CV) for all except: median (range) for Tmax; arithmetic mean (% CV) for t½ The above ratios are presented as geometric mean ratio (90% Confidence Intervals).

| | Single Dose, Food Effect | | | |
|---|---|---|---|---|
| | 22 mg ECS | | 22 mg Matrix (Example 4) | |
| Evaluation | Fasted (Reference) | Fed (Test) | Fasted (Reference) | Fed (Test) |
| $C_{max}$ (ng/ml) | 101 (28%) | 113 (20%) | 89 (29%) | 136 (25%) |
| $AUC_{inf}$ (ng*hr/ml) | 757 (23%) | 732 (21%) | 781 (27%) | 823 (24%) |
| $T_{max}$ (hr) | 4.0 (2.0-6.0) | 4.0 (3.0-6.0) | 2.5 (1.0-6.0) | 3.0 (2.0-6.0) |
| t½ (hr) | 5.6 (60%) | 4.9 (31%) | 5.3 (51%) | 4.8 (56%) |
| $C_{max}$ Ratio (%) | 100% | 113% (100-128%) | 100% | 153% (135-174%) |
| RBA (%) | 100% | 100% (95-106%) | 100% | 105% (99-110%) |

The above values are reported as Geometric mean (% CV) for all except: median (range) for Tmax; arithmetic mean (% CV) for t½. The above ratios are presented as geometric mean ratio (90% Confidence Intervals).

| | Predicted Steady-State PK | | | |
|---|---|---|---|---|
| | 10 mg IR BID Fasted (Reference) | 22 mg ECS QD Fasted (Test) | 22 mg Matrix QD (Example 4) Fasted (Test) | 22 mg Matrix QD (Example 12) Fasted (Test) |
| $C_{max, ss}$ (ng/ml) | 112.7 (30%) | 104.5 (30%) | 92.6 (32%) | 66.2 (27%) |
| $C_{min, ss}$ (ng/ml) | 5.0 (66%) | 3.80 (92%) | 3.31 (89%) | 7.36 (60%) |
| $C_{min, dn, ss}$ (ng/ml/mg) | 0.25 (66%) | 0.17 (92%) | 0.15 (89%) | 0.33 (60%) |
| $C_{min, ss}$ Ratio (%) | 100% | 74% (59-92%) | 64% (51-81%) | 159% (134-190%) |
| $C_{max, ss}/C_{min, ss}$ | 23 | 28 | 28 | 9 |
| Time above 17 ng/ml (hrs) | 13.4 (2 × 6.7 hrs) | 13.2 | 14.1 | 17.6 |
| Drug holiday (time below 17 ng/ml) (hrs) | 10.6 | 10.8 | 9.9 | 6.4 |

The above parameters are presented as geometric mean (% CV). The above ratios are presented as geometric mean ratio (90% Confidence Intervals).

was performed and the following endpoints for tofacitinib are determined: $C_{max}$, $T_{max}$, $AUC_{inf}$, $AUC_{last}$. An additional endpoint was determined for the dose normalized relative bioavailability (% RBA) of tofacitinib for the 11 mg sustained release formulations relative to the 22 mg sustained release formulation.

The study was a randomized, open-label, single dose, 2-period, 2-treatment, 2-sequence crossover study in 20 healthy male subjects (See Table 42). Subjects received two different sustained release formulations of tofacitinib with a washout period of 3 days between doses. The sustained release formulations were given as an 11 or 22 mg single dose.

TABLE 42

| Sequence | Period 1 | Period 2 |
|---|---|---|
| AB (n = 10) | A | B |
| BA (n = 10) | B | A |

A: Extrudable Core System Tablet, 11 mg; prepared in Example 1 above.
B: Extrudable Core System Tablet, 22 mg; prepared in Example 1 above.

Subjects were fasted overnight for at least 8 hours prior to administration of the study drug. On the morning of Day 1 of each period, all subjects received a single oral dose of study drug with 240 mL of water. Subjects were allowed a standardized lunch 4 hours after dose administration.

Dosage Forms Administered:

Tofacitinib 22 mg Sustained Release dosage forms: prepared in Example 1 above.

Tofacitinib 11 mg Sustained Release dosage forms: prepared in Example 1 above.

During all study periods, blood samples to provide plasma for pharmacokinetic analysis was collected at periodic time points. The study results are provided in Table 43. PK samples were analyzed using standard validated analytical methods. Dose normalized natural log transformed $AUC_{inf}$, $AUC_{last}$ and $C_{max}$ were analyzed for tofacitinib using a mixed effect model with sequence, period and treatment as fixed effects and subject within sequence as a random effect. Estimates of the adjusted mean differences (Test-Reference) and corresponding 90% confidence intervals were obtained from the model. The adjusted mean differences and 90% confidence intervals for the differences was exponentiated to provide estimates of the ratio of adjusted geometric means (Test/Reference) and 90% confidence intervals for the ratios. The 22 mg sustained release formulation was the Reference treatment and the 11 mg sustained release formulation was the Test treatments.

The relative bioavailability of tofacitinib was estimated as the ratio of dose-normalized adjusted geometric means for Test and Reference for $AUC_{inf}$.

The PK parameters $AUC_{inf}$, $AUC_{last}$, $C_{max}$, $T_{max}$, and $t_{1/2}$ were summarized descriptively by treatment and analyte (when applicable). For $AUC_{inf}$ and $C_{max}$, individual subject parameters are plotted by treatment for each analyte separately (when applicable). Concentrations were listed and summarized descriptively by PK sampling time, treatment and analyte (when applicable). Individual subject, mean and median profiles of the concentration-time data were plotted by treatment and analyte (when applicable). For summary statistics, and mean and median plots by sampling time, the nominal PK sampling time were used, for individual subject plots by time, the actual PK sampling time were used.

Predicted steady-state values were obtained via the superposition method using the software package WinNonLin (Pharsight Corp). Superposition was used on each individual's pharmacokinetic profile to generate the steady-state pharmacokinetic profile of each individual.

TABLE 43

| | Single Dose PK Parameters | |
|---|---|---|
| | 11 mg (Test) | 22 mg (Reference) |
| $C_{max}$ (ng/ml) | 42.2 (32%) | 84.4 (22%) |
| $C_{max, dn}$ (ng/ml/mg) | 3.84 (32%) | 3.84 (22%) |
| $AUC_{inf}$ (ng*hr/ml) | 315.6 (21%) | 645.8 (23%) |
| $AUC_{inf, dn}$ (ng*hr/ml/mg) | 28.7 (21%) | 29.4 (23%) |
| $T_{max}$ (hr) | 3.0 (2.0-4.0) | 3.0 (2.0-4.0) |
| t½ (hr) | 6.25 (36%) | 7.3 (46%) |
| $C_{max, dn}$ Ratio (%) | 100% (91-110%) | 100% |
| $AUC_{inf, dn}$ Ratio (%) | 98% (95-101%) | 100% |

The above values are reported as Geometric mean (% CV) for all except: median (range) for Tmax; arithmetic mean (% CV) for t½. The above ratios are presented as geometric mean ratio (90% Confidence Intervals).

| | Predicted Steady-State PK | |
|---|---|---|
| | 11 mg QD (Test) | 22 mg QD (Reference) |
| $C_{max, ss}$ (ng/ml) | 43.6 (35%) | 87.6 (25%) |
| $C_{min, ss}$ (ng/ml) | 1.7 (53%) | 3.5 (75%) |
| $C_{min, dn, ss}$ (ng/ml/mg) | 0.15 (53%) | 0.16 (75%) |
| $C_{min, dn, ss}$ Ratio (%) | 95% (72-125%) | 100% |
| $C_{max, ss}/C_{min, ss}$ | 26 | 25 |
| Time above 17 ng/ml (hrs) | 6.6 | 11.1 |
| Drug holiday (Time below 17 ng/ml) (hrs) | 17.4 | 12.9 |

The above parameters are presented as geometric mean (% CV). The above ratios are presented as geometric mean ratio (90% Confidence Intervals).

Sustained-release dosage forms containing 11 mg and 22 mg of tofacitinib which release and dissolve tofacitinib according to the claims (based on dissolution test 1) provide dose-proportional pharmacokinetic performance and meet the desired pharmacokinetic claims.

Example 18 Study D

The relative bioavailability of 11 mg tofacitinib sustained release tablets relative to a single dose of two, 5 mg tofacitinib immediate release (IR) tablets were performed and the following endpoints for tofacitinib were determined: $C_{max}$, $T_{max}$, $AUC_{inf}$, $AUC_{last}$. An additional endpoint was determined for the relative bioavailability (% RBA) of tofacitinib for each sustained release formulations relative to the IR formulation.

The study was a randomized, open-label, single dose, 2-period, 2-treatment, 2-sequence crossover study in 26 healthy subjects (See Table 44). Subjects received either the 11 mg sustained release formulations of tofacitinib citrate or two, 5 mg immediate release formulation of tofacitinib citrate with a washout period of 3 days between doses.

TABLE 44

| Sequence | Period 1 | Period 2 |
|---|---|---|
| AB (n = 13) | A | B |
| BA (n = 13) | B | A |

A: Extrudable Core System Tablet, 11 mg; prepared as follows:

TABLE 45

| # | Material | Function | Composition (%) | 300 kg Batch |
|---|---|---|---|---|
| 1 | Tofacitinib Citrate | Active | 8.885 | 26.656 |
| 2 | Sorbitol | Osmagen | 76.115 | 228.344 |
| 3 | Hydroxyethylcellulose | Viscosifying Agent | 8.000 | 24.000 |
| 4 | Copovidone | Binder | 6.000 | 18.000 |
| 5 | Magnesium Stearate | Lubricant | 1.000 | 3.000 |
|  | Core Tablet Weight | — | 100% | 300.000 kg |

One-half of the batch quantity of sorbitol, 114.172 kilograms, was added to an 800 L bin. The batch quantity of Copovidone, 18.000 kilograms, was then added to the 800 L bin. The batch quantity of Tofacitinib, 26.656 kilograms, was then added to the 800 L bin. The batch quantity of Hydroxycellulose, 24.000 kilograms, was then added to the 800 L bin. The remaining one-half of the batch quantity of sorbitol, 114.172 grams was added to the 800 L bin. All materials were added via a vacuum transfer system and passed through a Comil rotary mill equipped with a 0.032" screen and a round edge impeller running at approximately 1400 RPM. All of the components are blended in the bin for 20 minutes at 12+/−1 RPM.

The blend was passed through a Comil rotary mill equipped with a 0.032" screen and a round edge impeller running at approximately 1400 RPM. The blend was collected in a second 800 L bin. The bin contents were blended for 20 minutes at 12+/−1 RPM.

Magnesium stearate, 3.000 kilograms, was passed through an 850-micron mesh screen and was added to the bin and contents are blended for 5 minutes at 12+/−1 RPM. Tablets were compressed using 0.2080"×0.4160" modified oval tooling on a Manesty Mark IV rotary tablet press, to an average target weight of 200 mg+/−5%, average target thickness of 4.17 mm+/−0.05 mm, and a target hardness of 11 kp. Tablets were passed through a deduster and a metal detector.

TABLE 46

| Composition of coated 200 mgW tablet | % in coating | mg/ tablet | coat w/w (%) | Batch Quantity (kilograms) |
|---|---|---|---|---|
| 1. Tofacitinib Citrate Tablet Core | — | 200 | — | — |
| 2. Cellulose Acetate (Type 398-10) | 1.8% | 8.4 | 4.2 | 13.5 |
| 3. Hydroxypropyl Cellulose (Klucel EF) | 1.2% | 5.6 | 2.8 | 9.0 |
| 4. Methanol | 19.6% | (91.5) | — | 147.0 |
| 5. Acetone | 77.4% | (361.2) | — | 580.5 |
| Total Weight | 100% | 214.0 | 7.0 | 750.0 |

The 750-kilogram coating solution was prepared according to the following steps. First, the entire 147.0 kilograms of methanol and 580.5 grams of acetone were added to a 250-gallon vessel. 13.5 kilograms of cellulose acetate were added to the mixture. 9.0 kilogram of hydroxypropyl cellulose were added to the mixture. The contents of the container were mixed for 1 hour. This procedure created a 3% solids (w/w) solution.

250 kilograms of the 200 mg weight oval tablets were coated in a Vector HC-130 operating at 8 rpm and an airflow of 1500 CFM having an exhaust temperature of 28 deg C. The 3% solids (w/w) solution was applied until the wet weight gain reached a level of 7%. The tablets were then removed from the coating pan and dried at 45 C for 24 hours.

A single hole (600 micron) was drilled in the end of the band of the oval tablet. The hole can be drilled either by mechanical means or via laser ablation. A coating of 7% provided the following release in pH 6.8 media, paddles at 50 rpm based on Dissolution test 1 (Table 47):

TABLE 47

| Time (hr) | 11 mg tablet % Drug Dissolved |
|---|---|
| 1 | 8 |
| 2.5 | 49 |
| 6 | 89 |

B: Tofacitinib 2×5 mg Immediate Release Tablet (reference) prepared as follows:

TABLE 48

Composition of the 5 mg Immediate Release Tablet

| Component Name | Grade | Unit Composition (mg) |
|---|---|---|
| 1. Tofacitinib Citrate | Pharm | 8.078 |
| 2. Microcrystalline Cellulose | Ph. Eur/NF/JP | 122.615 |
| 3. Lactose Monohydrate | Ph. Eur/NF/JP | 61.307 |
| 4. Croscarmellose Sodium | Ph. Eur/NF/JP | 6.000 |
| 5. Magnesium Stearate | Ph. Eur/NF/JP | 0.500 |
| 6. Magnesium Stearate | Ph. Eur/NF/JP | 1.500 |
| TABLET CORE WEIGHT: | | 200.000 |
| 7. Opadry II White (HPMC based) | Pharm | 6.000 |
| 8. Purified Water | Ph. Eur/USP/JP | (34.000) |
| Total: | | 206.000 mg |

The tablet is manufactured according to the following process. Components 1-4 are combined and processed using a blend-mill-blend procedure. Component 5 is then added to the blend contents and combined using a blending procedure. This lubricated blend is than dry granulated. Component 6 is then added to the dry granulation and combined using a blending procedure. The lubricated granulation is compressed into 200 mg weight tablets using a rotary tablet press. The tablets are then coated using a film coater which sprays a solution containing Components 7 and 8 until 6 mg of coating has been applied to the tablets.

Subjects were fasted overnight for at least 8 hours prior to administration of the study drug. On the morning of Day 1 of each period, all subjects received a single oral dose of study drug with 240 mL of water. Subjects were allowed a standardized lunch 4 hours after dose administration.

Dosage Forms Administered:

Tofacitinib 5 mg Immediate Release Tablet (reference): prepared as describe above.

Tofacitinib 11 mg Sustained Release dosage forms: prepared as described above.

During all study periods, blood samples to provide plasma for pharmacokinetic analysis was collected at periodic time points. The study results are provided in Table 49. PK samples were analyzed using standard validated analytical methods. Dose normalized natural log transformed $AUC_{inf}$, $AUC_{last}$ and $C_{max}$ were analyzed for tofacitinib using a mixed effect model with sequence, period and treatment as fixed effects and subject within sequence as a random effect. Estimates of the adjusted mean differences (Test-Reference) and corresponding 90% confidence intervals were obtained from the model. The adjusted mean differences and 90% confidence intervals for the differences was exponentiated to provide estimates of the ratio of adjusted geometric means (Test/Reference) and 90% confidence intervals for the ratios. The 2×5 mg immediate release formulation was the Reference treatment and the 11 mg sustained release formulation was the Test treatment.

The relative bioavailability of tofacitinib was estimated as the ratio of geometric means for Test and Reference for $AUC_{inf}$.

The PK parameters $AUC_{inf}$, $AUC_{last}$, $C_{max}$, $T_{max}$, and $t_{1/2}$ were summarized descriptively by treatment and analyte (when applicable). For $AUC_{inf}$ and $C_{max}$, individual subject parameters are plotted by treatment for each analyte separately (when applicable). Concentrations were listed and summarized descriptively by PK sampling time, treatment and analyte (when applicable). Individual subject, mean and median profiles of the concentration-time data were plotted by treatment and analyte (when applicable). For summary statistics, and mean and median plots by sampling time, the nominal PK sampling time were used, for individual subject plots by time, the actual PK sampling time were used.

Predicted steady-state values were obtained via the superposition method using the software package WinNonLin (Pharsight Corp). Superposition was used on each individual's pharmacokinetic profile to generate the steady-state pharmacokinetic profile of each individual.

TABLE 49

| | Single Dose PK Parameters | |
|---|---|---|
| | 11 mg modified release (Test) | 2 × 5 mg immediate release (Reference) |
| $C_{max}$ (ng/ml) | 40.8 (29%) | 88.2 (29%) |
| $C_{max, dn}$ (ng/ml/mg) | 3.70 (29%) | 8.82 (29%) |
| $AUC_{inf}$ (ng*hr/ml) | 297.5 (23%) | 286.3 (20%) |
| $AUC_{inf, dn}$ (ng*hr/ml/mg) | 27.0 (23%) | 28.6 (20%) |
| $T_{max}$ (hr) | 3.54 (3.00-6.00) | 0.50 (0.50-2.00) |
| $t_{1/2}$ (hr) | 5.705 (41%) | 3.413 (18%) |
| $C_{max(adj)}$ Ratio (%) | 92% (85-100%) | 100% |
| $AUC_{inf}$ Ratio (%) | 104% (100%-107%) | 100% |

The above values are reported as Geometric mean (% CV) for all except: median (range) for Tmax; arithmetic mean (% CV) for t½. The above ratios are presented as geometric mean ratio (90% Confidence Intervals).

| | Predicted Steady-State PK | |
|---|---|---|
| | 11 mg modified release QD (Test) | 2 × 5 mg immediate release BID (Reference) |
| $C_{max, ss}$ (ng/ml) | 41.6 (31%) | 45.0 (28%) |
| $C_{min, ss}$ (ng/ml) | 1.3 (60%) | 1.5 (53%) |
| $C_{min, dn, ss}$ (ng/ml/mg) | 0.12 (60%) | 0.15 (53%) |
| $C_{min, dn, ss}$ Ratio (%) | 88% (73%-106%) | 100% |
| $C_{max, ss}/C_{min, ss}$ | 32 | 30 |

TABLE 49-continued

| | | |
|---|---|---|
| Time above 17 ng/ml (hrs) | 6.3 | 5.6 |
| Drug holiday (Time below 17 ng/ml) (hrs) | 17.7 | 18.4 |

The above parameters are presented as geometric mean (% CV). The above ratios are presented as geometric mean ratio (90% Confidence Intervals).

Sustained-release dosage forms containing 11 mg of tofacitinib which release and dissolve 80% of tofacitinib in 4-5 hours provide pharmacokinetic performance similar to immediate release dosage forms containing 10 mg of tofacitinib and meet the desired pharmacokinetic claims when dosed in the fasted state.

We claim:

1. A method of treating an immunological disorder in a subject comprising administering to the subject in need thereof a once daily pharmaceutical dosage form comprising
   a core comprising 11 mg of tofacitinib, or an equivalent amount of tofacitinib in the form of a pharmaceutically acceptable salt thereof, and an osmagen, and
   a semi-permeable membrane coating surrounding the core wherein said coating comprises a water-insoluble polymer,
   wherein said dosage form is a sustained release dosage form, and when added to a test medium comprising 900 mL of 0.05M pH 6.8 potassium phosphate buffer at 37° C. in a standard USP rotating paddle apparatus and the paddles are rotated at 50 rpm, dissolves not more than 30% of the tofacitinib, or pharmaceutically acceptable salt thereof, in 1 hour, and not less than 35% and not more than 75% of the tofacitinib, or pharmaceutically acceptable salt thereof, in 2.5 hours and not less than 75% of the tofacitinib, or pharmaceutically acceptable salt thereof, in 5 hours and wherein said dosage form delivers the tofacitinib, or pharmaceutically acceptable salt thereof, to a subject primarily by osmotic pressure and wherein the water-insoluble polymer is a cellulose derivative that sustains release of the tofacitinib, or pharmaceutically acceptable salt thereof, wherein the immunological disorder is selected from the group consisting of rheumatoid arthritis, psoriasis, psoriatic arthritis, ulcerative colitis, ankylosing spondylitis, and juvenile idiopathic arthritis.

2. The method of claim 1, wherein the immunological disorder is rheumatoid arthritis.

3. The method of claim 1, wherein the immunological disorder is ulcerative colitis.

4. The method of claim 1, further comprising one or more additional agents which modulate a mammalian immune system or anti-inflammatory agents.

5. The method of claim 4, wherein the additional agent is selected from the group consisting of a nonbiologic disease-modifying antirheumatic drug (DMARD), methotrexate, glucocorticoid, glucocorticoid receptor agonist, leflunomide, nonsteroidal anti-inflammatory drugs, 6-mercaptopurine, azathioprine, sulfasalazine, and 5-aminosalicylate drugs.

6. The method of claim 5, wherein the additional agent is selected from the group consisting of a nonbiologic DMARD and glucocorticoid receptor agonist.

7. The method of claim 5, wherein the additional agent is methotrexate.

8. A method of treating an immunological disorder in a subject comprising administering to the subject in need thereof a once daily pharmaceutical dosage form comprising
a core comprising 11 mg of tofacitinib, or an equivalent amount of tofacitinib in the form of a pharmaceutically acceptable salt thereof, and an osmagen,
and a semi-permeable membrane coating surrounding the core wherein said coating comprises a water-insoluble polymer,
wherein the dosage form is a sustained release dosage form and when administered orally to the subject provides an AUC in the range of 80% to 125% of the AUC of 10 mg of tofacitinib or an equivalent amount of tofacitinib in the form of a pharmaceutically acceptable salt thereof administered as an immediate release formulation BID and provides a ratio of geometric mean plasma $C_{max}$ to $C_{min}$ from about 10 to about 100 and wherein the dosage form delivers the tofacitinib, or pharmaceutically acceptable salt thereof, to the subject primarily by osmotic pressure and wherein the water-insoluble polymer is a cellulose derivative that sustains release of the tofacitinib or pharmaceutically acceptable salt thereof, wherein the immunological disorder is selected from the group consisting of rheumatoid arthritis, psoriasis, psoriatic arthritis, ulcerative colitis, ankylosing spondylitis, and juvenile idiopathic arthritis.

9. The method of claim 8, wherein the immunological disorder is rheumatoid arthritis.

10. The method of claim 9, wherein the immunological disorder is ulcerative colitis.

11. The method of claim 8, further comprising one or more additional agents which modulate a mammalian immune system or anti-inflammatory agents.

12. The method of claim 11, wherein the additional agent is selected from the group consisting of a nonbiologic disease-modifying antirheumatic drug (DMARD), methotrexate, glucocorticoid, glucocorticoid receptor agonist, leflunomide, nonsteroidal anti-inflammatory drugs, 6-mercaptopurine, azathioprine, sulfasalazine, and 5-aminosalicylate drugs.

13. The method of claim 12, wherein the additional agent is selected from the group consisting of a nonbiologic DMARD and a glucocorticoid receptor agonist.

14. The method of claim 12, wherein the additional agent is methotrexate.

15. The method of claim 8, wherein the AUC range is 90% to 110% and the geometric mean plasma concentration $C_{max}$ to $C_{min}$ from about 20 to about 40.

16. The method of claim 15, wherein the geometric mean plasma concentration $C_{max}$ to $C_{min}$ from about 20 to about 30.

17. The method of claim 8, wherein when the dosage form is administered orally to the subject and provides a mean plasma $C_{max}$ in the range of 70% to 125% of the mean plasma $C_{max}$ of tofacitinib administered as the immediate release formulation BID at steady state.

18. The method of claim 8, wherein when the dosage form is administered orally to the subject and provides a drug holiday in the range of 80% to 110% of the drug holiday of tofacitinib administered as the immediate release formulation BID over a 24 hour period.

19. The method of claim 8, having a drug holiday from about 15 to about 18 hours over the 24 hour period.

20. A method of treating an immunological disorder in a subject comprising administering to the subject in need thereof a once daily pharmaceutical dosage form comprising
a core comprising 11 mg of tofacitinib, or an equivalent amount of tofacitinib in the form of a pharmaceutically acceptable salt thereof, and an osmagen,
and a semi-permeable membrane coating surrounding the core wherein said coating comprises a water-insoluble polymer,
wherein said dosage form is a sustained release dosage form, and when administered to a subject has a mean area under the plasma concentration versus time curve following administration from about 17 ng-hr/mL per mg of tofacitinib dosed to about 42 ng-hr/mL per mg of tofacitinib dosed and a ratio of geometric mean plasma $C_{max}$ to $C_{min}$ from about 10 to about 100 and wherein said dosage form delivers the tofacitinib, or pharmaceutically acceptable salt thereof, to the subject primarily by osmotic pressure and wherein the water-insoluble polymer is a cellulose derivative that sustains release of the tofacitinib, or pharmaceutically acceptable salt thereof, wherein the immunological disorder is selected from the group consisting of rheumatoid arthritis, psoriasis, psoriatic arthritis, ulcerative colitis, ankylosing spondylitis, and juvenile idiopathic arthritis.

21. The method of claim 20, wherein the immunological disorder is rheumatoid arthritis.

22. The method of claim 20, wherein the immunological disorder ulcerative colitis.

23. The method of claim 20, further comprising one or more additional agents which modulate a mammalian immune system or anti-inflammatory agents.

24. The method of claim 23, wherein the additional agent is selected from the group consisting of a nonbiologic disease-modifying antirheumatic drug (DMARD), methotrexate, glucocorticoid, glucocorticoid receptor agonist, leflunomide, nonsteroidal anti-inflammatory drugs, 6-mercaptopurine, azathioprine, sulfasalazine, and 5-aminosalicylate drugs.

25. The method of claim 24, wherein the additional agent is selected from the group consisting of a nonbiologic DMARD and a glucocorticoid receptor agonist.

26. The method of claim 24, wherein the additional agent is methotrexate.

27. The method of claim 20, wherein the ratio of geometric mean plasma $C_{max}$ to $C_{min}$ from about 20 to about 40.

28. The method of claim 27, wherein the ratio of geometric mean plasma $C_{max}$ to $C_{min}$ from about 20 to about 30.

29. The method of claim 20, wherein the subject has a single, continuous time above about 17 ng/ml from about 6 to about 15 hours and a single, continuous time below about 17 ng/ml from about 9 to about 18 hours over a dosing 24 hours interval.

30. The method of claim 29, wherein the subject has a single, continuous time above about 17 ng/ml from about 6 to about 9 hours.

31. The method of claim 29, wherein the subject has a single, continuous time below about 17 ng/ml from about 15 to about 18 hours.

32. The method of claim 29, wherein the subject has a single, continuous time above about 17 ng/ml from about 11 to about 15 hours.

33. The method of claim 29, wherein the subject has a single, continuous time below about 17 ng/ml from about 9 to about 13 hours.

34. The method of claim 20, wherein the subject has a mean maximum plasma concentration ($C_{max}$) from about 3 ng/mL per mg to about 6 ng/mL per mg of tofacitinib dosed.

35. The method of claim 20, wherein said dosage form delivers the tofacitinib, or pharmaceutically acceptable salt thereof, by a system selected from the group consisting of an extrudable core system, a swellable core system, and an asymmetric membrane technology.

36. The method of claim 20, wherein said cellulose derivative is cellulose acetate.

37. The method of claim 20, wherein said coating further comprising a water soluble polymer having an average molecular weight between 2000 and 100,000 daltons.

38. The method of claim 20, wherein said water soluble polymer is selected from the group consisting of water soluble cellulose derivatives, acacia, dextrin, guar gum, maltodextrin, sodium alginate, starch, polyacrylates, and polyvinyl alcohols.

39. The method of claim 38, wherein said water soluble cellulose derivatives comprises hydroxypropylcellulose, hydroxypropylmethylcellulose or hydroxyethylcellulose.

40. The method of claim 20, wherein the osmagen is a sugar.

41. The method of claim 40, wherein the sugar is sorbitol.

42. The method of claim 20, wherein the subject has a mean steady-state minimum plasma concentration ($C_{min}$) less than about 0.3 ng/mL per mg of tofacitinib dosed.

43. The method of claim 20, wherein the subject has a mean fed/fasted ratio of the area under the plasma concentration versus time curve from about 0.7 to about 1.4 and a mean fed/fasted ratio of the maximum plasma concentration ($C_{max}$) from about 0.7 to about 1.4.

44. The method of claim 1, wherein the immunological disorder is psoriatic arthritis.

45. The method of claim 1, wherein the immunological disorder is ankylosing spondylitis.

46. The method of claim 8, wherein the immunological disorder is psoriatic arthritis.

47. The method of claim 8, wherein the immunological disorder is ankylosing spondylitis.

48. The method of claim 20, wherein the immunological disorder is psoriatic arthritis.

49. The method of claim 20, wherein the immunological disorder is ankylosing spondylitis.

50. A method of treating an immunological disorder in a subject comprising administering to the subject in need thereof a once daily pharmaceutical dosage form comprising
a core comprising 22 mg of tofacitinib, or an equivalent amount of tofacitinib in the form of a pharmaceutically acceptable salt thereof, and an osmagen, and
a semi-permeable membrane coating surrounding the core wherein said coating comprises a water-insoluble polymer,
wherein said dosage form is a sustained release dosage form, and when added to a test medium comprising 900 mL of 0.05M pH 6.8 potassium phosphate buffer at 37° C. in a standard USP rotating paddle apparatus and the paddles are rotated at 50 rpm, dissolves not more than 30% of the tofacitinib, or pharmaceutically acceptable salt thereof, in 1 hour, and not less than 35% and not more than 75% of the tofacitinib, or pharmaceutically acceptable salt thereof, in 2.5 hours and not less than 75% of the tofacitinib, or pharmaceutically acceptable salt thereof, in 5 hours and wherein said dosage form delivers the tofacitinib, or pharmaceutically acceptable salt thereof, to a subject primarily by osmotic pressure and wherein the water-insoluble polymer is a cellulose derivative that sustains release of the tofacitinib, or pharmaceutically acceptable salt thereof, wherein the immunological disorder is selected from the group consisting of rheumatoid arthritis, psoriasis, psoriatic arthritis, ulcerative colitis, ankylosing spondylitis, and juvenile idiopathic arthritis.

51. The method of claim 50, wherein the immunological disorder is rheumatoid arthritis.

52. The method of claim 50, wherein the immunological disorder is ulcerative colitis.

53. The method of claim 50, wherein the immunological disorder is psoriatic arthritis.

54. The method of claim 50, wherein the immunological disorder is ankylosing spondylitis.

55. The method of claim 50, further comprising one or more additional agents which modulate a mammalian immune system or anti-inflammatory agents.

56. The method of claim 55, wherein the additional agent is selected from the group consisting of a nonbiologic disease-modifying antirheumatic drug (DMARD), methotrexate, glucocorticoid, glucocorticoid receptor agonist, leflunomide, nonsteroidal anti-inflammatory drugs, 6-mercaptopurine, azathioprine, sulfasalazine, and 5-aminosalicylate drugs.

57. The method of claim 56, wherein the additional agent is selected from the group consisting of a nonbiologic DMARD and glucocorticoid receptor agonist.

58. The method of claim 56, wherein the additional agent is methotrexate.

59. A method of treating an immunological disorder in a subject comprising administering to the subject in need thereof a once daily pharmaceutical dosage form comprising
a core comprising 22 mg of tofacitinib, or an equivalent amount of tofacitinib in the form of a pharmaceutically acceptable salt thereof, and an osmagen,
and a semi-permeable membrane coating surrounding the core wherein said coating comprises a water-insoluble polymer,
wherein the dosage form is a sustained release dosage form and when administered orally to the subject provides an AUC in the range of 80% to 125% of the AUC of 10 mg of tofacitinib or an equivalent amount of tofacitinib in the form of a pharmaceutically acceptable salt thereof administered as an immediate release formulation BID and provides a ratio of geometric mean plasma $C_{max}$ to $C_{min}$ from about 10 to about 100 and wherein the dosage form delivers the tofacitinib, or pharmaceutically acceptable salt thereof, to the subject primarily by osmotic pressure and wherein the water-insoluble polymer is a cellulose derivative that sustains release of the tofacitinib or pharmaceutically acceptable salt thereof, wherein the immunological disorder is selected from the group consisting of rheumatoid arthritis, psoriasis, psoriatic arthritis, ulcerative colitis, ankylosing spondylitis, and juvenile idiopathic arthritis.

60. The method of claim 59, wherein the immunological disorder is rheumatoid arthritis.

61. The method of claim 59, wherein the immunological disorder is ulcerative colitis.

62. The method of claim 59, wherein the immunological disorder is psoriatic arthritis.

63. The method of claim 59, wherein the immunological disorder is ankylosing spondylitis.

64. The method of claim 59, further comprising one or more additional agents which modulate a mammalian immune system or anti-inflammatory agents.

65. The method of claim 64, wherein the additional agent is selected from the group consisting of a nonbiologic disease-modifying antirheumatic drug (DMARD), methotrexate, glucocorticoid, glucocorticoid receptor agonist, leflunomide, nonsteroidal anti-inflammatory drugs, 6-mercaptopurine, azathioprine, sulfasalazine, and 5-aminosalicylate drugs.

66. The method of claim 65, wherein the additional agent is selected from the group consisting of a nonbiologic DMARD and glucocorticoid receptor agonist.

67. The method of claim 65, wherein the additional agent is methotrexate.

68. The method of claim 59, wherein the AUC range is 90% to 110% and the geometric mean plasma concentration $C_{max}$ to $C_{min}$ from about 20 to about 40.

69. The method of claim 68, wherein the geometric mean plasma concentration $C_{max}$ to $C_{min}$ from about 20 to about 30.

70. The method of claim 59, wherein when the dosage form is administered orally to the subject provides a mean plasma $C_{max}$ in the range of 70% to 125% of the mean plasma $C_{max}$ of tofacitinib administered as the immediate release formulation BID at steady state.

71. The method of claim 59, wherein when the dosage form is administered orally to the subject provides a drug holiday in the range of 80% to 110% of the drug holiday of tofacitinib administered as the immediate release formulation BID over a 24 hour period.

72. The method of claim 59, having a drug holiday from about 15 to about 18 hours over the 24 hour period.

73. A method of treating an immunological disorder in a subject comprising administering to the subject in need thereof a once daily pharmaceutical dosage form comprising
   a core comprising 22 mg of tofacitinib, or an equivalent amount of tofacitinib in the form of a pharmaceutically acceptable salt thereof, and an osmagen,
   and a semi-permeable membrane coating surrounding the core wherein said coating comprises a water-insoluble polymer,
   wherein said dosage form is a sustained release dosage form, and when administered to a subject has a mean area under the plasma concentration versus time curve following administration from about 17 ng-hr/mL per mg of tofacitinib dosed to about 42 ng-hr/mL per mg of tofacitinib dosed and a ratio of geometric mean plasma $C_{max}$ to $C_{min}$ from about 10 to about 100 and wherein said dosage form delivers the tofacitinib, or pharmaceutically acceptable salt thereof, to the subject primarily by osmotic pressure and wherein the water-insoluble polymer is a cellulose derivative that sustains release of the tofacitinib, or pharmaceutically acceptable salt thereof, wherein the immunological disorder is selected from the group consisting of rheumatoid arthritis, psoriasis, psoriatic arthritis, ulcerative colitis, ankylosing spondylitis, and juvenile idiopathic arthritis.

74. The method of claim 73, wherein the immunological disorder is rheumatoid arthritis.

75. The method of claim 73, wherein the immunological disorder is ulcerative colitis.

76. The method of claim 73, wherein the immunological disorder is psoriatic arthritis.

77. The method of claim 73, wherein the immunological disorder is ankylosing spondylitis.

78. The method of claim 73, further comprising one or more additional agents which modulate a mammalian immune system or anti-inflammatory agents.

79. The method of claim 78, wherein the additional agent is selected from the group consisting of a nonbiologic disease-modifying antirheumatic drug (DMARD), methotrexate, glucocorticoid, glucocorticoid receptor agonist, leflunomide, nonsteroidal anti-inflammatory drugs, 6-mercaptopurine, azathioprine, sulfasalazine, and 5-aminosalicylate drugs.

80. The method of claim 79, wherein the additional agent is selected from the group consisting of a nonbiologic DMARD and glucocorticoid receptor agonist.

81. The method of claim 79, wherein the additional agent is methotrexate.

82. The method of claim 73, wherein the ratio of geometric mean plasma $C_{max}$ to $C_{min}$ from about 20 to about 40.

83. The method of claim 82, wherein the ratio of geometric mean plasma $C_{max}$ to $C_{min}$ from about 20 to about 30.

84. The method of claim 73, wherein the subject has a single, continuous time above about 17 ng/ml from about 6 to about 15 hours and a single, continuous time below about 17 ng/ml from about 9 to about 18 hours over a dosing 24 hours interval.

85. The method of claim 84, wherein the subject has a single, continuous time above about 17 ng/ml from about 6 to about 9 hours.

86. The method of claim 84, wherein the subject has a single, continuous time below about 17 ng/ml from about 15 to about 18 hours.

87. The method of claim 84, wherein the subject has a single, continuous time above about 17 ng/ml from about 11 to about 15 hours.

88. The method of claim 84, wherein the subject has a single, continuous time below about 17 ng/ml from about 9 to about 13 hours.

89. The method of claim 73, wherein the subject has a mean maximum plasma concentration ($C_{max}$) from about 3 ng/mL per mg to about 6 ng/mL per mg of tofacitinib dosed.

90. The method of claim 73, wherein said dosage form delivers the tofacitinib, or pharmaceutically acceptable salt thereof, by a system selected from the group consisting of an extrudable core system, a swellable core system, and an asymmetric membrane technology.

91. The method of claim 73, wherein said cellulose derivative is cellulose acetate.

92. The method of claim 73, wherein said coating further comprising a water soluble polymer having an average molecular weight between 2000 and 100,000 daltons.

93. The method of claim 73, wherein said water soluble polymer is selected from the group consisting of water soluble cellulose derivatives, acacia, dextrin, guar gum, maltodextrin, sodium alginate, starch, polyacrylates, and polyvinyl alcohols.

94. The method of claim 93, wherein said water soluble cellulose derivatives comprises hydroxypropylcellulose, hydroxypropylmethylcellulose or hydroxyethylcellulose.

95. The method of claim 73, wherein the osmagen is a sugar.

96. The method of claim 95, wherein the sugar is sorbitol.

97. The method of claim 73, wherein the subject has a mean steady-state minimum plasma concentration ($C_{min}$) less than about 0.3 ng/mL per mg of tofacitinib dosed.

98. The method of claim 73, wherein the subject has a mean fed/fasted ratio of the area under the plasma concentration versus time curve from about 0.7 to about 1.4 and a mean fed/fasted ratio of the maximum plasma concentration ($C_{max}$) from about 0.7 to about 1.4.

* * * * *